United States Patent [19]

Kawabata et al.

[11] Patent Number: 5,422,039
[45] Date of Patent: Jun. 6, 1995

[54] LIQUID CRYSTAL MATERIAL, LIQUID CRYSTAL COMPOSITION AND LIQUID CRYSTAL ELEMENT

[75] Inventors: Junichi Kawabata; Shinichi Nishiyama, both of Sodegaura, Japan

[73] Assignee: Mitsui Petrochemical Industries, Ltd., Tokyo, Japan

[21] Appl. No.: 217,564

[22] Filed: Mar. 25, 1994

[30] Foreign Application Priority Data

Mar. 25, 1993 [JP] Japan ................................ 5-066453

[51] Int. Cl.$^6$ ................ C09K 19/32; C09K 19/34; C07C 69/76
[52] U.S. Cl. .................. 252/299.62; 252/299.61; 560/56; 560/80; 560/127
[58] Field of Search ............. 252/299.62, 299.01, 252/299.61; 560/56, 80, 127; 359/103

[56] References Cited

U.S. PATENT DOCUMENTS

| | | | |
|---|---|---|---|
| 4,367,924 | 1/1983 | Clark | 359/103 |
| 4,576,732 | 3/1986 | Isogai et al. | 252/299.65 |
| 5,322,639 | 6/1994 | Kawabata et al. | 252/299.62 |
| 5,346,646 | 9/1994 | Kawabata et al. | 252/299.62 |
| 5,356,561 | 10/1994 | Shimizu | 252/299.62 |

FOREIGN PATENT DOCUMENTS

| | | |
|---|---|---|
| 0332456 | 10/1989 | European Pat. Off. |
| 0431929 | 6/1991 | European Pat. Off. |
| 0465048 | 1/1992 | European Pat. Off. |
| 0467662 | 1/1992 | European Pat. Off. |
| 0549347 | 6/1993 | European Pat. Off. |

OTHER PUBLICATIONS

R. B. Meyer, et al. "J. de Phys." vol. 36, L, pp. L-69-71.
Masaaki Taguchi, et al. "Proceedings of the 11th Conf. on Liquid Crystal", pp. 168-169 (1985).

*Primary Examiner*—Shean Wu
*Attorney, Agent, or Firm*—Sherman and Shalloway

[57] ABSTRACT

Disclosed is a liquid crystal material represented by the following formula [I]:

$$R-X-A^1-Y^1-A^2-(Y^2-A^3)_n-Z-R^* \qquad [I]$$

wherein R is an alkyl or polyfluoroalkyl group; X is a group such as —COO—, or a single bond; n is 0 or 1; $A^1$, $A^2$ and $A^3$ are each a cyclic group such as tetralin, and at least one of them has an optically active group; $Y^1$ and $Y^2$ are each a group such as —COO—; Z is a group such as —O—, or a single bond; and $R^*$ is an optically active group. Also disclosed are a liquid crystal composition comprising the liquid crystal material represented by the above formula, and a liquid crystal element in which the liquid crystal material is used. The liquid crystal material of the invention shows excellent liquid crystal characteristics because it has at least two optically active groups.

18 Claims, 16 Drawing Sheets

LIQUID CRYSTAL MATERIAL, LIQUID CRYSTAL COMPOSITION AND LIQUID CRYSTAL ELEMENT

FIELD OF THE INVENTION.

The present invention relates to a liquid crystal material having at least two optically active carbon atoms in a tetralin ring and a hydrocarbon chain structure, and to a liquid crystal composition comprising the liquid crystal material and a liquid crystal element in which the liquid crystal material is used.

BACKGROUND OF THE INVENTION.

Currently widely used display devices in which liquid crystal compounds are incorporated are usually driven by TN (twisted nematic) mode.

When driving by TN mode is adopted, however, the positions of liquid crystal compound molecules in an element of the device must be altered in order to change a displayed image. As a result, there are involved such problems that the driving time of the device is prolonged, and the voltage required for altering positions of the liquid crystal compound molecules, i.e., power consumption, becomes large.

Switching elements incorporating ferroelectric liquid crystal compounds, different from those in which TN mode or STN mode is utilized, can function only by altering the molecular orientation direction of the liquid crystal compounds, and hence the switching time is prominently shortened. Further, the value Ps×E obtained from a spontaneous polarization (Ps) of the ferroelectric liquid crystal compound and an intensity of the electric field (E) applied is an effective energy output for altering the molecular orientation direction of the liquid crystal compound, and accordingly the power consumption is also significantly diminished. Such ferroelectric liquid crystal compounds as mentioned above have two stable states, namely, bistability, in accordance with the direction of the applied electric field, and therefore show very excellent switching threshold value characteristics. Accordingly, the ferroelectric liquid crystal compounds are particularly suitable for display devices for animations.

When these ferroelectric liquid crystal compounds are used in optical switching elements, etc., they are required to have various characteristics such as an operating temperature in the vicinity of or not higher than room temperature, a wide operating temperature range, a high switching speed (quick), and a switching threshold value voltage in an appropriate range. Of these characteristics, the operating temperature range is a particularly important property when the ferroelectric liquid crystal compounds are put into practical use.

So far as ferroelectric liquid crystal compounds known hitherto are concerned, however, they have drawbacks such as a generally narrow operating temperature range, and an operating temperature range in a high temperature region not including room temperature even when their operating temperature range is wide, as described, for example, in R. B. Meyer et. al., "J. de Phys." Vol. 36 L, p. 69 (1975) and a paper reported by Masaaki Taguchi and Takamasa Harada, "Proceedings of Eleventh Conference on Liquid Crystal" p. 168 (1985). Thus, there are no available ferroelectric liquid crystal compound that is satisfactory from the standpoint of practical use.

OBJECT OF THE INVENTION

It is an object of the present invention to provide a liquid crystal material comprising a tetralin compound having optically active carbon atoms in the tetralin ring and the hydrocarbon chain structure, a liquid crystal composition containing the liquid crystal material, and a liquid crystal element in which the liquid crystal material is used. In more detail, the object of the invention is to provide a novel Liquid crystal material which can form a liquid crystal element having excellent liquid crystal characteristics such as a wide operating temperature range, a high switching speed, an extremely small amount of power consumption and a stable contrast, and to provide such liquid crystal element.

SUMMARY OF THE INVENTION

The liquid crystal material of the present invention can be represented by the following formula [I]:

$$R-X-A^1-Y^1-A^2-(Y^2-A^3)_n-Z-R^* \qquad [I]$$

wherein R is an alkyl or polyfluoroalkyl group of 3 to 20 carbon atoms in which a part of $-CH_2-$ groups or $-CF_2-$ groups may be substituted with $-O-$ group, said $-CH_2-$ groups or $-CF_2-$ groups being not directly bonded to X and not adjacent to each other, X is a group selected from the group consisting of $-COO-$, $-O\text{---}CO-$, $-CO-$ and $-O-$, or a single bond, n is 0 or 1, at least one group of $A^1$, $A^2$ and $A^3$ existing in the formula [I] is an optically active group selected from the group consisting of

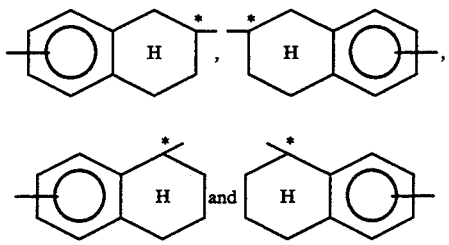

the residual groups of $A^1$, $A^2$ and $A^3$ are each independently a group selected from the group consisting of

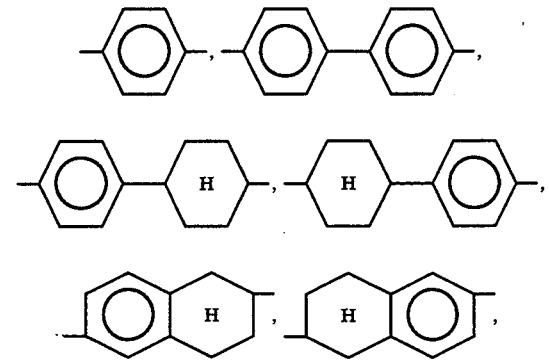

-continued

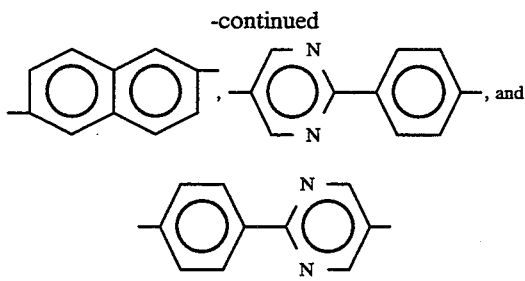

Y¹ and Y² are each independently a group selected from the group consisting of —COO—, —O—CO—, —CH₂CH₂—, —CH₂O—, —O—CH₂—, —CO—CH₂— and —CH₂—CO—, Z is a group selected from the group consisting of —O—, —CO—, —COO— and —O—CO—, or a single bond, and R* is an optically active group of 4 to 20 carbon atoms having at least one asymmetric carbon atom (a hydrogen atom bonded to a carbon atom of said optically active group may being substituted with a halogen atom).

The liquid crystal composition of the present invention contains a liquid crystal material comprising a tetralin compound represented by the above formula [I].

The liquid crystal element of the present invention comprises:
 a cell which includes two substrates facing each other and having a gap defined by the substrates, and
 a liquid crystal material filled in the gap,
 wherein the liquid crystal material comprises a tetralin compound represented by the above formula [I].

The liquid crystal material of the invention has optically active carbon atoms in at least two places of the tetralin ring and the hydrocarbon chain structure, and hence it is very useful as a liquid crystal material. The liquid crystal composition comprising the tetralin compound and the liquid crystal element filled with the material of the compound show excellent liquid crystal characteristics.

By the use of such liquid crystal material, there can be obtained various devices having excellent characteristics such as a wide operating temperature range, a high switching speed, an extremely small amount of power consumption and a stable contrast.

DETAILED DESCRIPTION OF THE INVENTION

Figure 1:
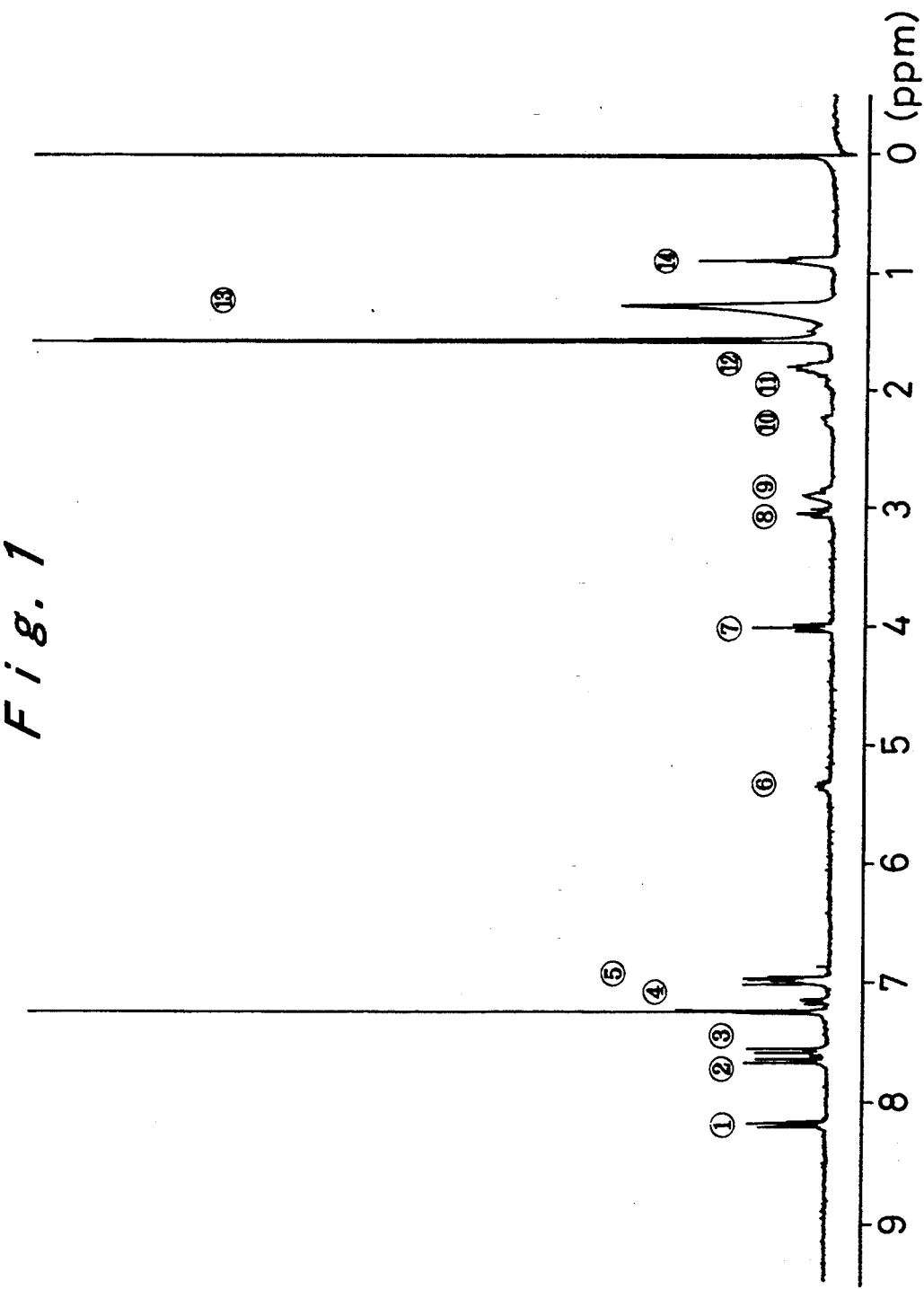
FIG. 1–13 each shows a ¹H-NMR spectrum of the resulting compound prepared in each Examples 1–12 and 14.

The present invention will be described in detail hereinafter.

First, the liquid crystal material of the present invention is described below.

The liquid crystal material of the present invention comprises a tetralin compound represented by the following formula [I]:

$$R—X—A^1—Y^1—A^2—(Y^2—A^3)_n—Z—R^* \quad [I]$$

wherein R is basically an alkyl or polyfluoroalkyl group of 3 to 20 carbon atoms.

The alkyl group may take any of a straight-chain form, a branched form and an alicyclic form. However, a carboxylic acid ester molecule with R being a straight-chain alkyl group exhibits excellent liquid crystal characteristics due to the linearly extended rigid straight structure of the molecule. Examples of such straight-chain alkyl group include hexyl, heptyl, octyl, nonyl, decyl, undecyl, dodecyl, tetradecyl, hexadecyl and octadecyl.

Examples of the polyfluoroalkyl group include groups obtained by substituting hydrogen atoms in the above alkyl groups with fluorine.

In the invention, a part of the —CH₂— groups or the —CF₂— groups which form R and which are not directly bonded to X and not adjacent to each other may be substituted with —O— group. Examples of the alkyl group in which the —CH₂— group is substituted with the —O— group include 2-hexyloxyethoxy, 3,6-dioxa-1-decyloxy and nonyloxymethyl.

In the formula [I], X is a group selected from the group consisting of —COO—, —O—CO—, —CO— and —O—, or a single bond. In the liquid crystal material of the invention, X is preferably —O— or a single bond.

In the formula [I], n is 0 or 1. Therefore, when n is 0, neither Y² nor A³ is present in the above formula.

At least one group of A¹, A² and A³ present in the formula [I] is an optically active group selected from the group consisting of

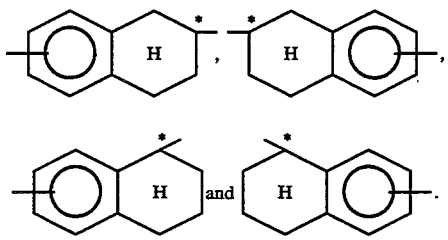

That is, the tetralin ring of the tetralin compound for forming the liquid crystal composition of the invention has an asymmetric carbon atom indicated by the symbol * in the above formulas.

When n is 0 in the above formula [I], at least any one of A¹ and A² is a group represented by any of the above formulas. When n is 1, at least any one of A¹, A² and A³ is a group represented by any of the above formulas, and further two or three of the groups may be those represented by any of the above formulas.

Examples of the 1,2,3,4-tetrahydronaphthyl groups which has optical activity and represented by the above formulas include R-1,2,3,4-tetrahydro-1,5-naphthyl, S-1,2,3,4-tetrahydro-1,5-naphthyl, R-1,2,3,4-tetrahydro-1,6-naphthyl, S-1,2,3,4-tetrahydro-1,6-naphthyl, R-1,2,3,4-tetrahydro-2,6-naphthyl, S-1,2,3,4-tetrahydro-2,6-naphthyl, R-1,2,3,4-tetrahydro-1,7-naphthyl and S-1,2,3,4-tetrahydro-1,7-naphthyl.

In the liquid crystal material of the present invention, the entire structure of the molecules is preferably linear, so that particularly preferred as the 1,2,3,4-tetrahydronaphthyl group having optical activity are R-1,2,3,4-tetrahydro-2,6-naphthyl and S-1,2,3,4-tetrahydro-2,6-naphthyl.

Likewise, particularly preferred as the 5,6,7,8-tetrahydronaphthyl group having optical activity are R-5,6,7,8-tetrahydro-2,6-naphthyl and S-5,6,7,8-tetrahydro-2,6-naphthyl.

The examples described above are those in which one tetralin ring has optical activity. However, when there are two or more tetralin rings in the compound, at least one of them may have optical activity, or all of them may have optical activity.

The groups of $A^1$, $A^2$ and $A^3$ which are not specified depending on the above condition and remains in the formula [I] are each independently a group selected from the group consisting of

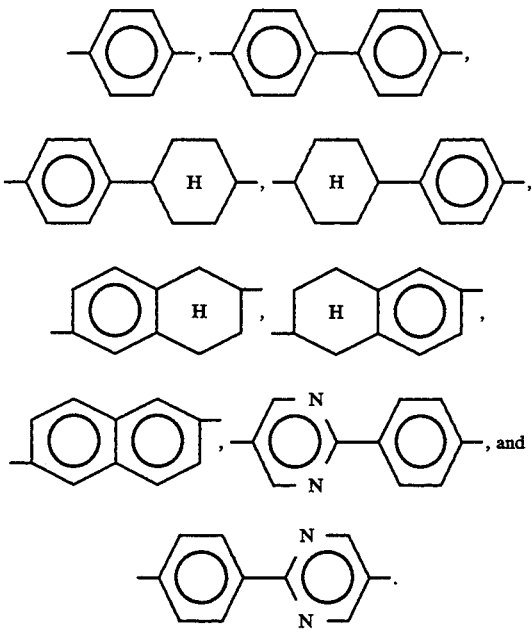

In the liquid crystal material of the present invention, the above groups do not have optical activity.

In the above formula [I], $Y^1$ and $Y^2$ are each independently a group selected from the group consisting of —COO—, —O—CO—, —CH$_2$CH$_2$—, —CH$_2$O—, —O—CH$_2$—, —CO—CH$_2$— and —CH$_2$—CO—. In the liquid crystal material of the invention, each of $Y^1$ and $Y^2$ is preferably —COO— or —O—CO—. Especially when the linearity of the molecule is taken into consideration, it is preferred that at least any one of $Y^1$ and $Y^2$ is —O—CO— or —COO—, and it is more preferred that both of them are —O—CO— or —COO—.

Z in the formula [I] is a group selected from the group consisting of —O—, —CO—, —COO— and —O—CO—, or a single bond. In the liquid crystal material of the present invention, Z is preferably —O— or —COO—.

R* in the formula [I] is an optically active group of 4 to 20 carbon atoms having at least one asymmetric carbon atom. Further, a hydrogen atom bonded to the carbon atom for constituting said optically active group may be substituted with a halogen atom such as F, Cl, Br or I.

Especially, R* is preferably a group represented by the following formula [II]:

wherein $Q^1$ is —(CH$_2$)$_q$— in which q is an integer of from 0 to 6, and one —CH$_2$— group may be substituted with —O— group. $Q^2$ and $Q^3$ are each independently an alkyl group of 1 to 10 carbon atoms, a fluoroalkyl group of 1 to 10 carbon atoms or a halogen atom, and $Q^2$ and $Q^3$ are different from each other. Examples of the alkyl group of 1 to 10 carbon atoms include methyl, ethyl, propyl, butyl, pentyl, hexyl, heptyl, octyl, nonyl and decyl. Examples of the fluoroalkyl group of 1 to 10 carbon atoms include groups obtained by substituting at least a part of hydrogen atoms bonded to the carbon atoms in the above examples of the alkyl group with a fluorine atom. Examples of the halogen atom include F, Cl, Br and I. $Q^2$ and $Q^3$ are groups or atoms different from each other, that is, they are never the same as each other. Further, when one of $Q^2$ and $Q^3$ is a halogen atom, the other is usually an alkyl group or an fluoroalkyl group.

When $Q^1$, $Q^2$ and $Q^3$ in the formula [II] have CH$_2$ group (—CH$_2$— structure) or CF$_2$ group (—CF$_2$— structure) in their structures, at least a part of the CH$_2$ groups or the CF$_2$ groups may be substituted with at least one group selected from the group consisting of —O—, —S—, —CO—, —CHX$^1$— (in which $X^1$ is a halogen atom), —CHCN—, —O—CO—, —O—COO—, —CO—O— and —CH=CH—. In this case, two hetero atoms (N, O, etc.) for forming these groups are not directly bonded to each other. Hence, the substitution with these groups never forms a new bond such as —O—O— or —N—O—.

Further, R* is preferably a group selected from the group consisting of —C*H (CF$_3$)—C$_6$H$_{13}$, —C*H (CF$_3$)—C$_5$H$_{11}$, —C*H (CF$_3$)—C$_4$H$_9$, —C*H (CH$_3$)—C$_8$H$_{17}$, —C*H (CH$_3$)—C$_7$H$_{15}$, —C*H (CH$_3$)—C$_6$H$_{13}$, —C*H (CH$_3$)—C$_5$H$_{11}$, —C*H (C$_2$H$_5$)—C$_5$H$_{11}$, —C*H (C$_2$H$_5$)—C$_6$H$_{13}$, —CH$_2$—C*H (CH$_3$)—C$_2$H$_5$, —(CH$_2$)$_3$—C*H (CH$_3$)—C$_2$H$_5$, —C*H (CF$_3$)—CH$_2$—COO—C$_2$H$_5$, —C*H (CF$_3$)—(CH$_2$)$_2$OCH$_3$, —C*H (CF$_3$)—(CH$_2$)$_3$OC$_2$H$_5$, —C*H (CF$_3$)—(CH$_2$)$_4$OCH$_3$ and —C*H (CF$_3$)—(CH$_2$)$_5$OC$_2$H$_5$. That is, R* is an optically active group having at least one asymmetric carbon atom. As described above, the hydrogen atom bonded to the carbon atom for constituting the optically active group may be substituted by a halogen atom such as fluorine.

Of the above groups, particularly preferred are —C*H (CF$_3$)—C$_6$H$_{13}$ and —C*H (CH$_3$)—C$_6$H$_{13}$, when the characteristics required for liquid crystal materials are taken into account.

Accordingly, examples of the tetralin compound represented by the above formula [I] include compounds set forth in Tables 1 to 15.

In Tables 1 to 15, the tetralin ring of the following formula

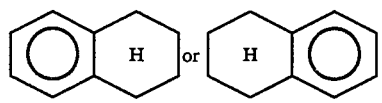

shown without bonding hands means a tetralin ring which has optical activity and represented by the following structure.

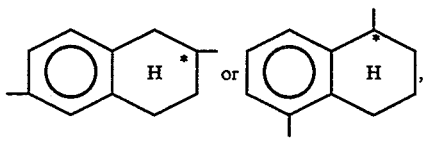

or

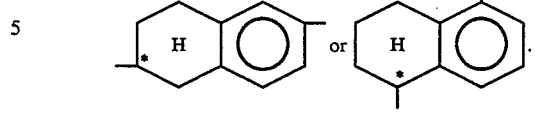

Each of the two asymmetric carbon atoms present in the compound represented by the formula [I] has R-form and S-form, and hence the compound of No. 1 in Tables 1 to 15 includes 16 kinds of compounds in total.

Specifically, examples of the compound represented by the above formula [I] wherein n is 1, namely, the compound represented by the following formula [I-A], include compounds shown in Tables 1 to 3.

$$R-X-A^1-Y^1-A^2-Y^2-A^3-Z-R^* \qquad [I-A]$$

TABLE 1

| [n = 1] Comp. No. | R | X | $A^1$ | $Y^1$ | $A^2$ | $Y^2$ |
|---|---|---|---|---|---|---|
| 1 | $C_{10}H_{21}-$ | $-O-$ | 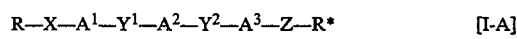 | $-COO-$ | (phenyl) | $-COO-$ |
| 2 | $C_{10}H_{21}-$ | " | (phenyl) | " | (tetralin H) | " |
| 3 | $C_{10}H_{21}-$ | " | (phenyl) | " | (phenyl) | " |
| 4 | $C_{10}H_{21}-$ | " | (tetralin H) | " | (phenyl) | " |
| 5 | $C_{10}H_{21}-$ | $-COO-$ | (tetralin H) | $-COO-$ | (phenyl) | $-COO-$ |
| 6 | $C_{10}H_{21}-$ | " | (phenyl) | " | (tetralin H) | " |
| 7 | $C_{10}H_{21}-$ | " | (phenyl) | " | (phenyl) | " |
| 8 | $C_{10}H_{21}-$ | " | (tetralin H) | " | (phenyl) | " |
| 9 | $C_{10}H_{21}-$ | — | (tetralin H) | $-COO-$ | (phenyl) | $-COO-$ |

TABLE 1-continued
| | | | | | |
|---|---|---|---|---|---|
| 10 | $C_{10}H_{21}-$ | — | 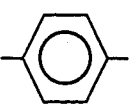 | 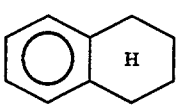 | " |
| 11 | $C_{10}H_{21}-$ | — | 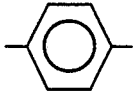 | 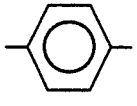 | " |
| 12 | $C_{10}H_{21}-$ | — | 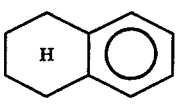 | 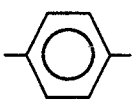 | " |
| Comp. No. | $A^3$ | Z | R* | Ex. No. |
|---|---|---|---|---|
| 1 | 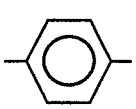 | —COO— | —C*H (CF$_3$) C$_6$H$_{13}$ | |
| 2 | 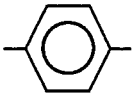 | " | " | |
| 3 | 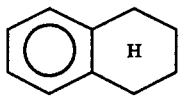 | " | " | |
| 4 | 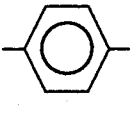 | " | " | |
| 5 | 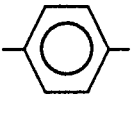 | —COO— | —C*H (CF$_3$) C$_6$H$_{13}$ | |
| 6 | 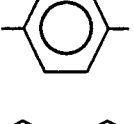 | " | " | |
| 7 | 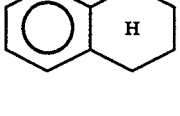 | " | " | |
| 8 |  | " | " | |
| 9 | 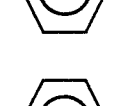 | —COO— | —C*H (CF$_3$) C$_6$H$_{13}$ | |
| 10 |  | " | " | |

TABLE 1-continued

| | | | | |
|---|---|---|---|---|
| 11 | [naphthalene with H] | " | " | |
| 12 | [phenyl] | " | " | |

TABLE 2

| [n = 1] Comp. No. | R | X | A¹ | Y¹ | A² | Y² |
|---|---|---|---|---|---|---|
| 13 | $C_{10}H_{21}-$ | —O— | [phenyl] | —OCO— | [phenyl] | —OCO— |
| 14 | $C_{10}H_{21}-$ | " | [phenyl] | " | [naphthalene H] | " |
| 15 | $C_{10}H_{21}-$ | " | [naphthalene H] | " | [phenyl] | " |
| 16 | $C_{10}H_{21}-$ | " | [phenyl] | " | [phenyl] | " |
| 17 | $C_{10}H_{21}-$ | —OCO— | [phenyl] | —OCO— | [phenyl] | —OCO— |
| 18 | $C_{10}H_{21}-$ | " | [phenyl] | " | [naphthalene H] | " |
| 19 | $C_{10}H_{21}-$ | " | [naphthalene H] | " | [phenyl] | " |
| 20 | $C_{10}H_{21}-$ | " | [phenyl] | " | [phenyl] | " |
| 21 | $C_{10}H_{21}-$ | — | [phenyl] | —OCO— | [phenyl] | —OCO— |
| 22 | $C_{10}H_{21}-$ | — | [phenyl] | " | [naphthalene H] | " |
| 23 | $C_{10}H_{21}-$ | — | [naphthalene H] | " | [phenyl] | " |

TABLE 2-continued
| | | | | | |
|---|---|---|---|---|---|
| 24 | $C_{10}H_{21}$— | — |  | " |  | " |
| Comp. No. | $A^3$ | Z | R* | Ex. No. |
|---|---|---|---|---|
| 13 | 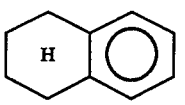 | —O— | —C*H (CF$_3$) C$_6$H$_{13}$ | |
| 14 |  | " | " | |
| 15 |  | " | " | |
| 16 | 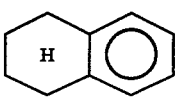 | " | " | |
| 17 | 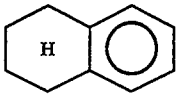 | —O— | —C*H (CF$_3$) C$_6$H$_{13}$ | |
| 18 | 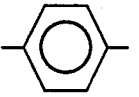 | " | " | |
| 19 |  | " | " | |
| 20 | 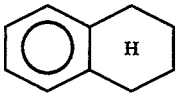 | " | " | |
| 21 | 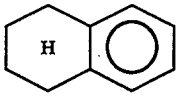 | —O— | —C*H (CF$_3$) C$_6$H$_{13}$ | |
| 22 | 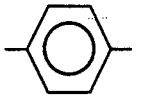 | " | " | |
| 23 |  | " | " | |
| 24 | 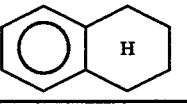 | " | " | |

TABLE 3
| [n = 1] Comp. No. | R | X | A$^1$ | Y$^1$ | A$^2$ | Y$^2$ |
|---|---|---|---|---|---|---|
| 25 | C$_{10}$H$_{21}$— | —O— |  | —OCO— | 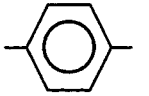 | —OCO— |
| 26 | C$_{10}$H$_{21}$— | " |  | " | 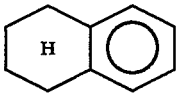 | " |
| 27 | C$_{10}$H$_{21}$— | " | 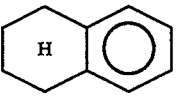 | " | 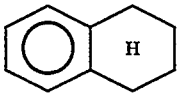 | " |
| 28 | C$_{10}$H$_{21}$— | " | 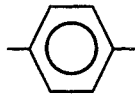 | " | 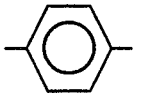 | " |
| 29 | C$_{10}$H$_{21}$— | —OCO— | 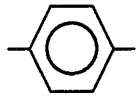 | —OCO— | 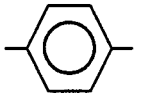 | —OCO— |
| 30 | C$_{10}$H$_{21}$— | " | 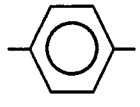 | " | 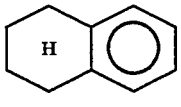 | " |
| 31 | C$_{10}$H$_{21}$— | " | 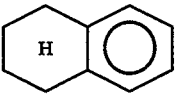 | " | 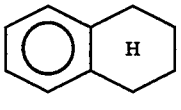 | " |
| 32 | C$_{10}$H$_{21}$— | " | 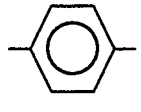 | " | 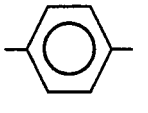 | " |
| 33 | C$_{10}$H$_{21}$— | — | 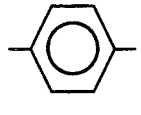 | —OCO— | 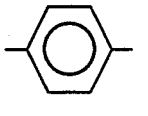 | —OCO— |
| 34 | C$_{10}$H$_{21}$— | — | 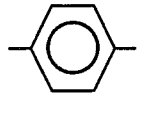 | " | 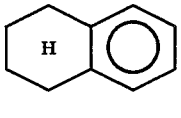 | " |
| 35 | C$_{10}$H$_{21}$— | — | 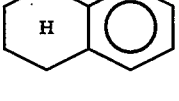 | " | 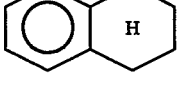 | " |
| 36 | C$_{10}$H$_{21}$— | — | 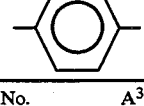 | " | 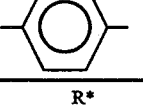 | " |
| Comp. No. | A$^3$ | Z | R* | Ex. No. |
|---|---|---|---|---|
| 25 | 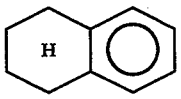 | —O— | —C*H (CF$_3$) C$_6$H$_{13}$ | |

TABLE 3-continued

| No. | Structure | | |
|---|---|---|---|
| 26 | ⌬ | " | " |
| 27 | ⌬ | " | " |
| 28 | ⌬⌬H | " | " |
| 29 | ⌬H⌬ | —O— | —C*H (CF₃) C₆H₁₃ |
| 30 | ⌬ | " | " |
| 31 | ⌬ | " | " |
| 32 | ⌬H⌬ | " | " |
| 33 | ⌬H⌬ | —O— | —C*H (CF₃) C₆H₁₃ |
| 34 | ⌬ | " | " |
| 35 | ⌬ | " | " |
| 36 | ⌬⌬H | " | " |

Examples of the compound represented by the above formula [I] wherein n is 0, namely, the compound represented by the following formula [I-B], include compounds shown in Tables 4 to 15.

$$R-X-A^1-Y^1-A^2-Z-R^* \qquad [\text{I-B}]$$

TABLE 4

| [n = 0] Comp. No. | R | X | A¹ | Y¹ | A² | Z | R* | Ex. No. |
|---|---|---|---|---|---|---|---|---|
| 37 | C₁₀H₂₁— | —O— | ⌬⌬H | —COO— | 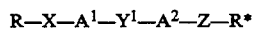 | —COO— | —C*H(CF₃)C₆H₁₃ | |

TABLE 4-continued

| [n = 0] Comp. No. | R | X | A¹ | Y¹ | A² | Z | R* | Ex. No. |
|---|---|---|---|---|---|---|---|---|
| 38 | $C_{10}H_{21}-$ | " | " | " | phenyl-cyclohexyl | " | " | |
| 39 | $C_{10}H_{21}-$ | " | " | " | cyclohexyl-phenyl | " | " | |
| 40 | $C_{10}H_{21}-$ | " | " | " | pyrimidinyl-phenyl | " | " | |
| 41 | $C_{10}H_{21}-$ | " | " | " | phenyl-pyrimidinyl | " | " | |
| 42 | $C_{10}H_{21}-$ | " | " | " | naphthyl | " | " | |
| 43 | $C_{10}H_{21}-$ | " | " | " | phenyl | " | " | |
| 44 | $C_{10}H_{21}-$ | — | tetrahydronaphthyl | $-COO-$ | biphenyl | $-COO-$ | $-C^*H(CF_3)C_6H_{13}$ | |
| 45 | $C_{10}H_{21}-$ | — | " | " | phenyl-cyclohexyl | " | " | |
| 46 | $C_{10}H_{21}-$ | — | " | " | cyclohexyl-phenyl | " | " | |
| 47 | $C_{10}H_{21}-$ | — | " | " | pyrimidinyl-phenyl | " | " | |
| 48 | $C_{10}H_{21}-$ | — | " | " | phenyl-pyrimidinyl | " | " | |
| 49 | $C_{10}H_{21}-$ | — | " | " | naphthyl | " | " | |

TABLE 4-continued
[n = 0]
| Comp. No. | R | X | A¹ | Y¹ | A² | Z | R* | Ex. No. |
|---|---|---|---|---|---|---|---|---|
| 50 | C₁₀H₂₁— | — | " | " | 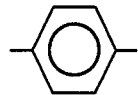 | " | " | |
TABLE 5
[n = 0]
| Comp. No. | R | X | A¹ | Y¹ | A² | Z | R* | Ex. No. |
|---|---|---|---|---|---|---|---|---|
| 51 | C₁₀H₂₁— | —O— | 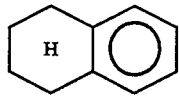 | —COO— | 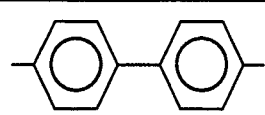 | —COO— | —C*H(CF₃)C₆H₁₃ | |
| 52 | C₁₀H₂₁— | " | " | " | 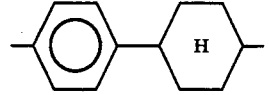 | " | " | |
| 53 | C₁₀H₂₁— | " | " | " | 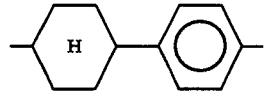 | " | " | |
| 54 | C₁₀H₂₁— | " | " | " | 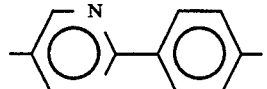 | " | " | |
| 55 | C₁₀H₂₁— | " | " | " | 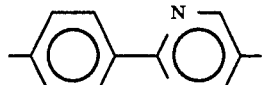 | " | " | |
| 56 | C₁₀H₂₁— | " | " | " | 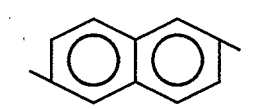 | " | " | |
| 57 | C₁₀H₂₁— | " | " | " | 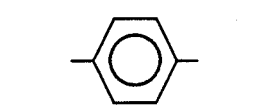 | " | " | |
| 58 | C₁₀H₂₁— | — | 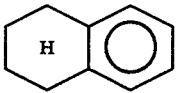 | —COO— | 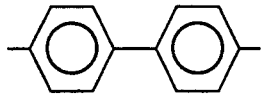 | —COO— | —C*H(CF₃)C₆H₁₃ | |
| 59 | C₁₀H₂₁— | — | " | " | 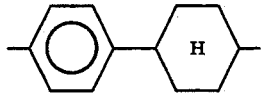 | " | " | |
| 60 | C₁₀H₂₁— | — | " | " | 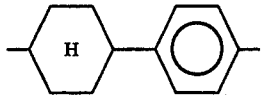 | " | " | |
| 61 | C₁₀H₂₁— | — | " | " | 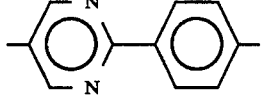 | " | " | |

TABLE 5-continued

[n = 0]

| Comp. No. | R | X | A¹ | Y¹ | A² | Z | R* | Ex. No. |
|---|---|---|---|---|---|---|---|---|
| 62 | C₁₀H₂₁— | — | " | " | (phenyl-pyrimidine) | " | " | |
| 63 | C₁₀H₂₁— | — | " | " | (naphthalene) | " | " | |
| 64 | C₁₀H₂₁— | — | " | " | (phenyl) | " | " | |

TABLE 6

| Comp. No. | R | X | A¹ | Y¹ | A² | Z | R* | Ex. No. |
|---|---|---|---|---|---|---|---|---|
| 65 | C₉H₁₉— | —OCO— | (tetrahydronaphthalene, H) | —OCO— | (biphenyl) | —O— | —C*H(CF₃)C₆H₁₃ | |
| 66 | C₉H₁₉— | " | " | " | (phenyl-cyclohexyl, H) | " | " | |
| 67 | C₉H₁₉— | " | " | " | (cyclohexyl-phenyl, H) | " | " | |
| 68 | C₉H₁₉— | " | " | " | (pyrimidine-phenyl) | " | " | |
| 69 | C₉H₁₉— | " | " | " | (phenyl-pyrimidine) | " | " | |
| 70 | C₉H₁₉— | " | " | " | (naphthalene) | " | " | |
| 71 | C₉H₁₉— | " | " | " | (phenyl) | " | " | |
| 72 | C₉H₁₉— | —OCO— | (tetrahydronaphthalene, H) | —OCO— | (biphenyl) | —O— | —C*H(CF₃)C₆H₁₃ | |
| 73 | C₉H₁₉— | " | " | " | (phenyl-cyclohexyl, H) | " | " | |

TABLE 6-continued

| Comp. No. | R | X | A¹ | Y¹ | A² | Z | R* | Ex. No. |
|---|---|---|---|---|---|---|---|---|
| 74 | C₉H₁₉— | " | " | " | cyclohexane(H)-phenyl | " | " | |
| 75 | C₉H₁₉— | " | " | " | pyrazine-phenyl | " | " | |
| 76 | C₉H₁₉— | " | " | " | phenyl-pyrimidine | " | " | |
| 77 | C₉H₁₉— | " | " | " | naphthalene | " | " | |
| 78 | C₉H₁₉— | " | " | " | phenyl | " | " | |

[n = 0]

TABLE 7

| Comp. No. | R | X | A¹ | Y¹ | A² | Z | R* | Ex. No. |
|---|---|---|---|---|---|---|---|---|
| 79 | C₁₀H₂₁— | —O— | biphenyl | —OCO— | decalin(H) | —O— | —C*H(CF₃)C₆H₁₃ | |
| 80 | C₁₀H₂₁— | " | phenyl-cyclohexane(H) | " | " | " | " | |
| 81 | C₁₀H₂₁— | " | cyclohexane(H)-phenyl | " | " | " | " | |
| 82 | C₁₀H₂₁— | " | pyrazine-phenyl | " | " | " | " | |
| 83 | C₁₀H₂₁— | " | phenyl-pyrimidine | " | " | " | " | |
| 84 | C₁₀H₂₁— | " | decalin(H)-phenyl | " | " | " | " | |
| 85 | C₁₀H₂₁— | " | naphthalene | " | " | " | " | |

TABLE 7-continued
| Comp. No. | R | X | A¹ | Y¹ | A² | Z | R* | Ex. No. |
|---|---|---|---|---|---|---|---|---|
| 86 | C₁₀H₂₁— | " |  | " | " | " | " | |
| 87 | C₁₀H₂₁— | —O— | 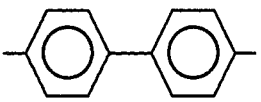 | —OCO— | 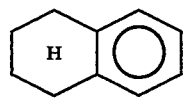 | —O— | —C*H(CF₃)C₆H₁₃ | |
| 88 | C₁₀H₂₁— | " | 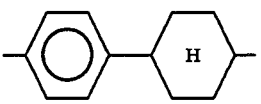 | " | " | " | " | |
| 89 | C₁₀H₂₁— | " | 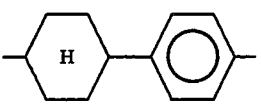 | " | " | " | " | |
| 90 | C₁₀H₂₁— | " | 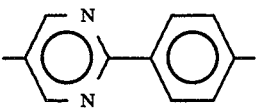 | " | " | " | " | |
| 91 | C₁₀H₂₁— | " | 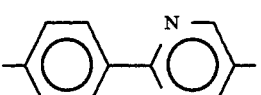 | " | " | " | " | |
| 92 | C₁₀H₂₁— | " | 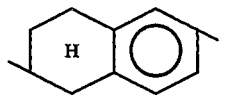 | " | " | " | " | |
| 93 | C₁₀H₂₁— | " | 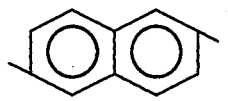 | " | " | " | " | |
| 94 | C₁₀H₂₁— | " | 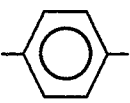 | " | " | " | " | |
[n = 0]
TABLE 8
| Comp. No. | R | X | A¹ | Y¹ | A² | Z | R* | Ex. No. |
|---|---|---|---|---|---|---|---|---|
| 95 | C₇H₁₅— | —O— | 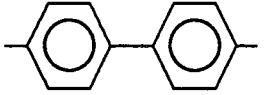 | —COO— | 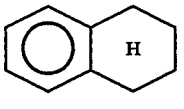 | —COO— | —C*H(CF₃)C₆H₁₃ | |
| 96 | C₈H₁₇— | " | " | " | " | " | " | |
| 97 | C₉H₁₉— | " | " | " | " | " | " | |
| 98 | C₁₀H₂₁— | " | " | " | " | " | " | 1,2 |
| 99 | C₁₁H₂₃— | " | " | " | " | " | " | |
| 100 | C₁₂H₂₅— | " | " | " | " | " | " | |
| 101 | C₁₄H₂₉— | " | " | " | " | " | " | |
| 102 | C₁₆H₃₃— | " | " | " | " | " | " | |
| 103 | C₇H₁₅— | — | 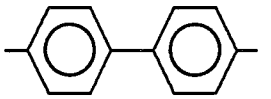 | —COO— | 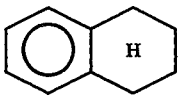 | —COO— | —C*H(CF₃)C₆H₁₃ | |

TABLE 8-continued

| Comp. No. | R | X | A¹ | Y¹ | A² | Z | R* | Ex. No. |
|---|---|---|---|---|---|---|---|---|
| 104 | $C_8H_{17}$— | — | " | " | " | " | " | 3,4 |
| 105 | $C_9H_{19}$— | — | " | " | " | " | " | |
| 106 | $C_{10}H_{21}$— | — | " | " | " | " | " | |
| 107 | $C_{11}H_{23}$— | — | " | " | " | " | " | |
| 108 | $C_{12}H_{25}$— | — | " | " | " | " | " | |
| 109 | $C_{14}H_{29}$— | — | " | " | " | " | " | 7,8 |
| 110 | $C_{16}H_{33}$— | — | " | " | " | " | " | |

[n = 0]

TABLE 9

| Comp. No. | R | X | A¹ | Y¹ | A² | Z | R* | Ex. No. |
|---|---|---|---|---|---|---|---|---|
| 111 | $C_{10}H_{21}$— | —O— | 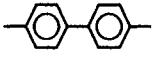 | —OCO— |  | —COO— | —C*H(CF₃)C₆H₁₃ | |
| 112 | $C_{10}H_{21}$— | " | " | —CH₂O— | " | " | " | |
| 113 | $C_{10}H_{21}$— | " | " | —OCH₂— | " | " | " | |
| 114 | $C_{10}H_{21}$— | " | " | —CH₂CH₂— | " | " | " | |
| 115 | $C_{10}H_{21}$— | " | " | —COCH₂— | " | " | " | |
| 116 | $C_{10}H_{21}$— | " | " | —CH₂CO— | " | " | " | |
| 117 | $C_{10}H_{21}$— | — | 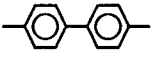 | —OCO— |  | —COO— | —C*H(CF₃)C₆H₁₃ | |
| 118 | $C_{10}H_{21}$— | — | " | —CH₂O— | " | " | " | |
| 119 | $C_{10}H_{21}$— | — | " | —OCH₂— | " | " | " | |
| 120 | $C_{10}H_{21}$— | — | " | —CH₂CH₂— | " | " | " | |
| 121 | $C_{10}H_{21}$— | — | " | —COCH₂— | " | " | " | |
| 122 | $C_{10}H_{21}$— | — | " | —CH₂CO— | " | " | " | |

[n = 0]

TABLE 10

| Comp. No. | R | X | A¹ | Y¹ | A² | Z | R* | Ex. No. |
|---|---|---|---|---|---|---|---|---|
| 123 | $C_{10}H_{21}$— | —O— | 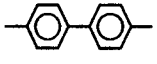 | —OCO— |  | —COO— | —C*H(CF₃)C₆H₁₃ | |
| 124 | $C_{10}H_{21}$— | " | " | —CH₂O— | " | " | " | |
| 125 | $C_{10}H_{21}$— | " | " | —OCH₂— | " | " | " | |
| 126 | $C_{10}H_{21}$— | " | " | —CH₂CH₂— | " | " | " | |
| 127 | $C_{10}H_{21}$— | " | " | —COCH₂— | " | " | " | |
| 128 | $C_{10}H_{21}$— | " | " | —CH₂CO— | " | " | " | |
| 129 | $C_{10}H_{21}$— | — | 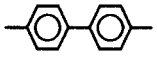 | —OCO— |  | —COO— | —C*H(CF₃)C₆H₁₃ | |
| 130 | $C_{10}H_{21}$— | — | " | —CH₂O— | " | " | " | |
| 131 | $C_{10}H_{21}$— | — | " | —OCH₂— | " | " | " | |
| 132 | $C_{10}H_{21}$— | — | " | —CH₂CH₂— | " | " | " | |
| 133 | $C_{10}H_{21}$— | — | " | —COCH₂— | " | " | " | |
| 134 | $C_{10}H_{21}$— | — | " | —CH₂CO— | " | " | " | |

[n = 0]

TABLE 11

| Comp. No. | R | X | A¹ | Y¹ | A² | Z | R* | Ex. No. |
|---|---|---|---|---|---|---|---|---|
| 135 | $C_{10}H_{21}$— | —O— | 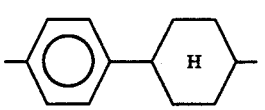 | —COO— | 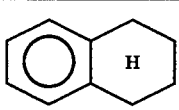 | —COO— | —C*H(CF₃)C₆H₁₃ | |
| 136 | $C_{10}H_{21}$— | " | 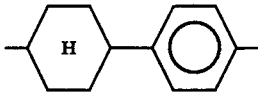 | " | " | " | " | |

TABLE 11-continued
| Comp. No. | R | X | A¹ | Y¹ | A² | Z | R* | Ex. No. |
|---|---|---|---|---|---|---|---|---|
| 137 | C₁₀H₂₁— | " | 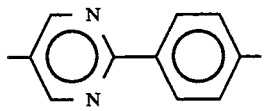 | " | " | " | " | |
| 138 | C₁₀H₂₁— | " | 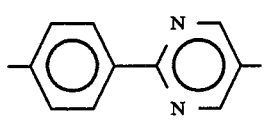 | " | " | " | " | |
| 139 | C₁₀H₂₁— | " | 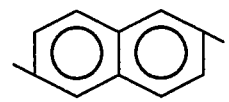 | " | " | " | " | |
| 140 | C₁₀H₂₁— | " | 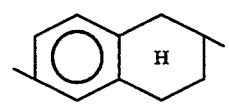 | " | " | " | " | |
| 141 | C₁₀H₂₁— | " | 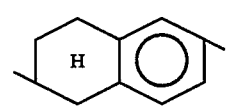 | " | " | " | " | |
| 142 | C₁₀H₂₁— | " | 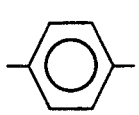 | " | " | " | " | |
| 143 | C₁₀H₂₁— | — | 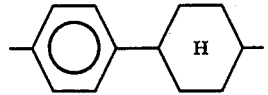 | —COO— | 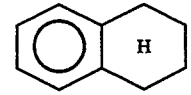 | —COO— | —C*H(CF₃)C₆H₁₃ | |
| 144 | C₁₀H₂₁— | — | 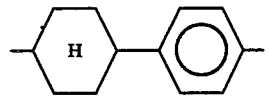 | " | " | " | " | |
| 145 | C₁₀H₂₁— | — | 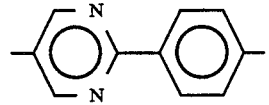 | " | " | " | " | |
| 146 | C₁₀H₂₁— | — | 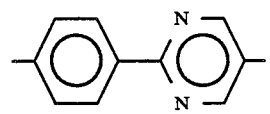 | " | " | " | " | |
| 147 | C₁₀H₂₁— | — | 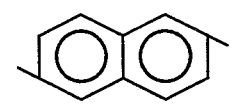 | " | " | " | " | |
| 148 | C₁₀H₂₁— | — | 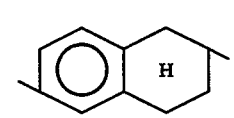 | " | " | " | " | |
| 149 | C₁₀H₂₁— | — | 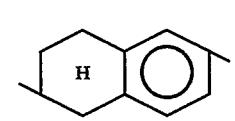 | " | " | " | " | |

TABLE 11-continued

| Comp. No. | R | X | A¹ | Y¹ | A² | Z | R* | Ex. No. |
|---|---|---|---|---|---|---|---|---|
| 150 | $C_{10}H_{21}-$ | — | (phenyl) | " | " | " | " | |

[n = 0]

TABLE 12

| Comp. No. | R | X | A¹ | Y¹ | A² | Z | R* | Ex. No. |
|---|---|---|---|---|---|---|---|---|
| 151 | $C_7H_{15}-$ | $-O-$ | (biphenyl) | $-COO-$ | (tetrahydronaphthyl, H) | $-COO-$ | $-C^*H(CF_3)C_4H_9$ | |
| 152 | $C_8H_{17}-$ | " | " | " | " | " | " | |
| 153 | $C_9H_{19}-$ | " | " | " | " | " | " | |
| 154 | $C_{10}H_{21}-$ | " | " | " | " | " | " | |
| 155 | $C_{11}H_{23}-$ | " | " | " | " | " | " | |
| 156 | $C_{12}H_{25}-$ | " | " | " | " | " | " | |
| 157 | $C_{14}H_{29}-$ | " | " | " | " | " | " | |
| 158 | $C_{16}H_{33}-$ | " | " | " | " | " | " | |
| 159 | $C_7H_{15}-$ | — | (biphenyl) | $-COO-$ | (tetrahydronaphthyl, H) | $-COO-$ | $-C^*H(CF_3)C_4H_9$ | |
| 160 | $C_8H_{17}-$ | — | " | " | " | " | " | |
| 161 | $C_9H_{19}-$ | — | " | " | " | " | " | |
| 162 | $C_{10}H_{21}-$ | — | " | " | " | " | " | |
| 163 | $C_{11}H_{23}-$ | — | " | " | " | " | " | |
| 164 | $C_{12}H_{25}-$ | — | " | " | " | " | " | 9,10 |
| 165 | $C_{14}H_{29}-$ | — | " | " | " | " | " | |
| 166 | $C_{16}H_{33}-$ | — | " | " | " | " | " | |

[n = 0]

TABLE 13

| Comp. No. | R | X | A¹ | Y¹ | A² | Z | R* | Ex. No. |
|---|---|---|---|---|---|---|---|---|
| 167 | $C_7H_{15}-$ | $-O-$ | (biphenyl) | $-COO-$ | (tetrahydronaphthyl, H) | $-COO-$ | $-C^*H(CF_3)CH_2$<br>$-COOC_2H_5$ | |
| 168 | $C_8H_{17}-$ | " | " | " | " | " | $-C^*H(CF_3)CH_2$<br>$-COOC_2H_5$ | |
| 169 | $C_9H_{19}-$ | " | " | " | " | " | $-C^*H(CF_3)CH_2$<br>$-COOC_2H_5$ | |
| 170 | $C_{10}H_{21}-$ | " | " | " | " | " | $-C^*H(CF_3)CH_2$<br>$-COOC_2H_5$ | 13,14 |
| 171 | $C_{11}H_{23}-$ | " | " | " | " | " | $-C^*H(CF_3)CH_2$<br>$-COOC_2H_5$ | |
| 172 | $C_{12}H_{25}-$ | " | " | " | " | " | $-C^*H(CF_3)CH_2$<br>$-COOC_2H_5$ | |
| 173 | $C_{14}H_{29}-$ | " | " | " | " | " | $-C^*H(CF_3)CH_2$<br>$-COOC_2H_5$ | |
| 174 | $C_{16}H_{33}-$ | " | " | " | " | " | $-C^*H(CF_3)CH_2$<br>$-COOC_2H_5$ | |
| 175 | $C_7H_{15}-$ | — | (biphenyl) | $-COO-$ | (tetrahydronaphthyl, H) | $-COO-$ | $-C^*H(CF_3)CH_2$<br>$-COOC_2H_5$ | |
| 176 | $C_8H_{17}-$ | — | " | " | " | " | $-C^*H(CF_3)CH_2$<br>$-COOC_2H_5$ | |
| 177 | $C_9H_{19}-$ | — | " | " | " | " | $-C^*H(CF_3)CH_2$<br>$-COOC_2H_5$ | |
| 178 | $C_{10}H_{21}-$ | — | " | " | " | " | $-C^*H(CF_3)CH_2$<br>$-COOC_2H_5$ | |

TABLE 13-continued

| Comp. No. | R | X | A¹ | Y¹ | A² | Z | R* | Ex. No. |
|---|---|---|---|---|---|---|---|---|
| 179 | $C_{11}H_{23}-$ | — | " | " | " | " | $-C^*H(CF_3)CH_2-COOC_2H_5$ | |
| 180 | $C_{12}H_{25}-$ | — | " | " | " | " | $-C^*H(CF_3)CH_2-COOC_2H_5$ | |
| 181 | $C_{14}H_{29}-$ | — | " | " | " | " | $-C^*H(CF_3)CH_2-COOC_2H_5$ | |
| 182 | $C_{16}H_{33}-$ | — | " | " | " | " | $-C^*H(CF_3)CH_2-COOC_2H_5$ | |

[n = 0]

TABLE 14

| Comp. No. | R | X | A¹ | Y¹ | A² | Z | R* | Ex. No. |
|---|---|---|---|---|---|---|---|---|
| 183 | $C_7H_{15}-$ | $-O-$ | 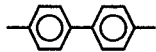 | $-COO-$ |  | $-COO-$ | $-C^*H(CF_3)(CH_2)_4OCH_3$ | |
| 184 | $C_8H_{17}-$ | " | " | " | " | " | " | |
| 185 | $C_9H_{19}-$ | " | " | " | " | " | " | |
| 186 | $C_{10}H_{21}-$ | " | " | " | " | " | " | 11,12 |
| 187 | $C_{11}H_{23}-$ | " | " | " | " | " | " | |
| 188 | $C_{12}H_{25}-$ | " | " | " | " | " | " | |
| 189 | $C_{14}H_{29}-$ | " | " | " | " | " | " | |
| 190 | $C_{16}H_{33}-$ | " | " | " | " | " | " | |
| 191 | $C_7H_{15}-$ | — | 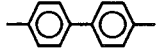 | $-COO-$ |  | $-COO-$ | $-C^*H(CF_3)(CH_2)_4OCH_3$ | |
| 192 | $C_8H_{17}-$ | — | " | " | " | " | " | |
| 193 | $C_9H_{19}-$ | — | " | " | " | " | " | |
| 194 | $C_{10}H_{21}-$ | — | " | " | " | " | " | |
| 195 | $C_{11}H_{23}-$ | — | " | " | " | " | " | |
| 196 | $C_{12}H_{25}-$ | — | " | " | " | " | " | |
| 197 | $C_{14}H_{29}-$ | — | " | " | " | " | " | |
| 198 | $C_{16}H_{33}-$ | — | " | " | " | " | " | |

[n = 0]

TABLE 15

| Comp. No. | R | X | A¹ | Y¹ | A² | Z | R* | Ex. No. |
|---|---|---|---|---|---|---|---|---|
| 199 | $C_7H_{15}-$ | $-O-$ | 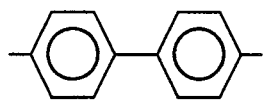 | $-COO-$ | 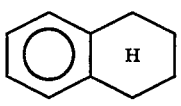 | $-COO-$ | $-C^*H(CH_3)C_6H_{13}$ | |
| 200 | $C_8H_{17}-$ | " | " | " | " | " | " | |
| 201 | $C_9H_{19}-$ | " | " | " | " | " | " | |
| 202 | $C_{10}H_{21}-$ | " | " | " | " | " | " | 5,6 |
| 203 | $C_{11}H_{23}-$ | " | " | " | " | " | " | |
| 204 | $C_{12}H_{25}-$ | " | " | " | " | " | " | |
| 205 | $C_{14}H_{29}-$ | " | " | " | " | " | " | |
| 206 | $C_{16}H_{33}-$ | " | " | " | " | " | " | |
| 207 | $C_7H_{15}-$ | — | 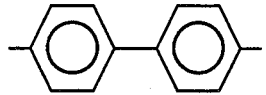 | $-COO-$ | 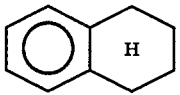 | $-COO-$ | $-C^*H(CH_3)C_6H_{13}$ | |
| 208 | $C_8H_{17}-$ | — | " | " | " | " | " | |
| 209 | $C_9H_{19}-$ | — | " | " | " | " | " | |
| 210 | $C_{10}H_{21}-$ | — | " | " | " | " | " | |
| 211 | $C_{11}H_{23}-$ | — | " | " | " | " | " | |
| 212 | $C_{12}H_{25}-$ | — | " | " | " | " | " | |
| 213 | $C_{14}H_{29}-$ | — | " | " | " | " | " | |
| 214 | $C_{16}H_{33}-$ | — | " | " | " | " | " | |

[n = 0]

In the liquid crystal material of the present invention, as described above, there are involved a compound in which the tetralin ring has S-form or R-form and a compound represented by the formula [I] in which the chain group R* has S-form or R-form.

Accordingly, when the liquid crystal material of the invention has one optically active tetralin ring, the liquid crystal material includes the following four types of compounds in view of optical activity.

Type 1
tetralin ring: S-form, chain group R*: S-form
Type 2
tetralin ring: S-form, chain group R*: R-form
Type 3
tetralin ring: R-form, chain group R*: S-form
Type 4
tetralin ring: R-form, chain group R*: R-form The liquid crystal material of the invention may be any compound of the above four types, and further it may be a mixture of these compounds. Of these compounds, the compound of Type 1 and the compound of Type 4 (Group A), or the compound of Type 2 and the compound of Type 3 (Group B) have molecular configurations which are enantiomers of each other, and they have equivalent performance as a liquid crystal material to each other. Accordingly, if compounds of Group A and compounds of Group B which are diastereomers of each other are compared and a compound of a group having larger spontaneous polarization is used, there can be obtained a liquid crystal element having a higher switching speed than those obtained by using compounds of other group.

Any liquid crystal material having optical activity in both the cyclic structure and the side chain, e.g., the liquid crystal material of the invention, has not been known heretofore.

For example, suppose a compound represented by the following formula [A]:

For example, when liquid crystal elements respectively obtained by using each of the liquid crystal materials (compounds) were measured on the switching speed, there was observed a distinct difference in the switching speed between the element obtained by using the compound represented by the formula [A-1] and the element obtained by using the compound represented by the formula [A-2]. Accordingly, if the compound showing a low switching speed is taken out from the compound (racemic modification) represented by the formula [A] and the diastereomer thereof is used singly, the switching speed is prominently increased as compared with the case where the racemic modification is used.

In other words, so far as at least the switching speed is concerned, when the liquid crystal material has two or more optically active carbon atoms, the compound in which the configuration of each optically active carbon atom increases a dipole moment of the whole molecules also increases the spontaneous polarization as a molecular aggregate, and hence such compound shows a switching speed higher than that of the diastereomer thereof (i.e., compound in which the configuration weakens a dipole moment of the whole molecules).

The compound as described above can be prepared by a specific combination of known synthetic techniques, in which the optical resolution of the starting material having a tetralin ring is carried out.

For example, a carboxylic acid ester compound suitable for the liquid crystal material represented by the above formula [I] may be prepared from an optically resolved compound selected from the group consisting of 1,2,3,4-tetrahydro-6-alkoxynaphthalene-2-carboxylic

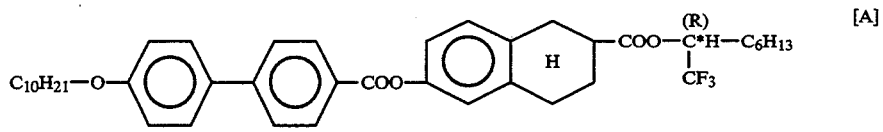

wherein the asymmetric carbon atom of R* is R-form.

When the tetralin ring portion is paid attention, the compound of the above formula [A] is a mixture of R-form represented by the following formula [A-1] and S-form represented by the following formula [A-2] in the same amounts, and hence any optical activity has not been observed in the tetralin ring portion.

acid, 1,2,3,4-tetrahydro-6-hydroxynaphthalene-2-carboxylic acid, 1,2,3,4-tetrahydro-6-benzyloxynaphthalene-2-carboxylic acid and esters derived therefrom, and a monoalchohol having 4–20 carbon atoms. In the optically resolved compound, an angle of rotation caused by an optical active structure having the chiral center which is one of the carbon atoms in the tetralin

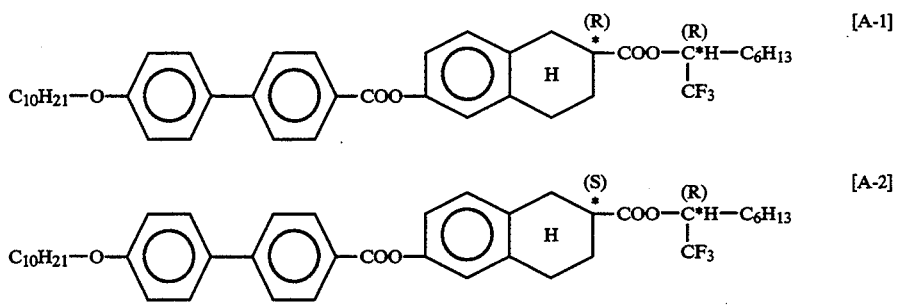

However, when the compound represented by the formula [A] is resolved into a compound represented by the formula [A-1] (R-form) and a compound represented by the formula [A-2] (S-form) and they are examined on their characteristics, it has been found that they are different in the chemical characteristics and moreover in the liquid crystal characteristics.

ring thereof comes to (−) or (+).

In the above method, when the above angle of rotation caused by the optical active structure in the tetralin ring is (+), it is preferred that the monoalchohol having 4–20 carbon atoms be 1-methylalchohol [RCH(CH$_3$)OH:R=C2–C18]. When the above angle of rotation caused by the optical active structure in the tetralin ring is (−), it is preferred that the monoalchohol having 4–20 carbon atoms be 1-trifluoromethylalchohol [RCH(CF₃)OH:R=C2–C18].
The method for preparing the carboxylic acid ester compounds in the present invention will be described in detail referring the following synthetic route.
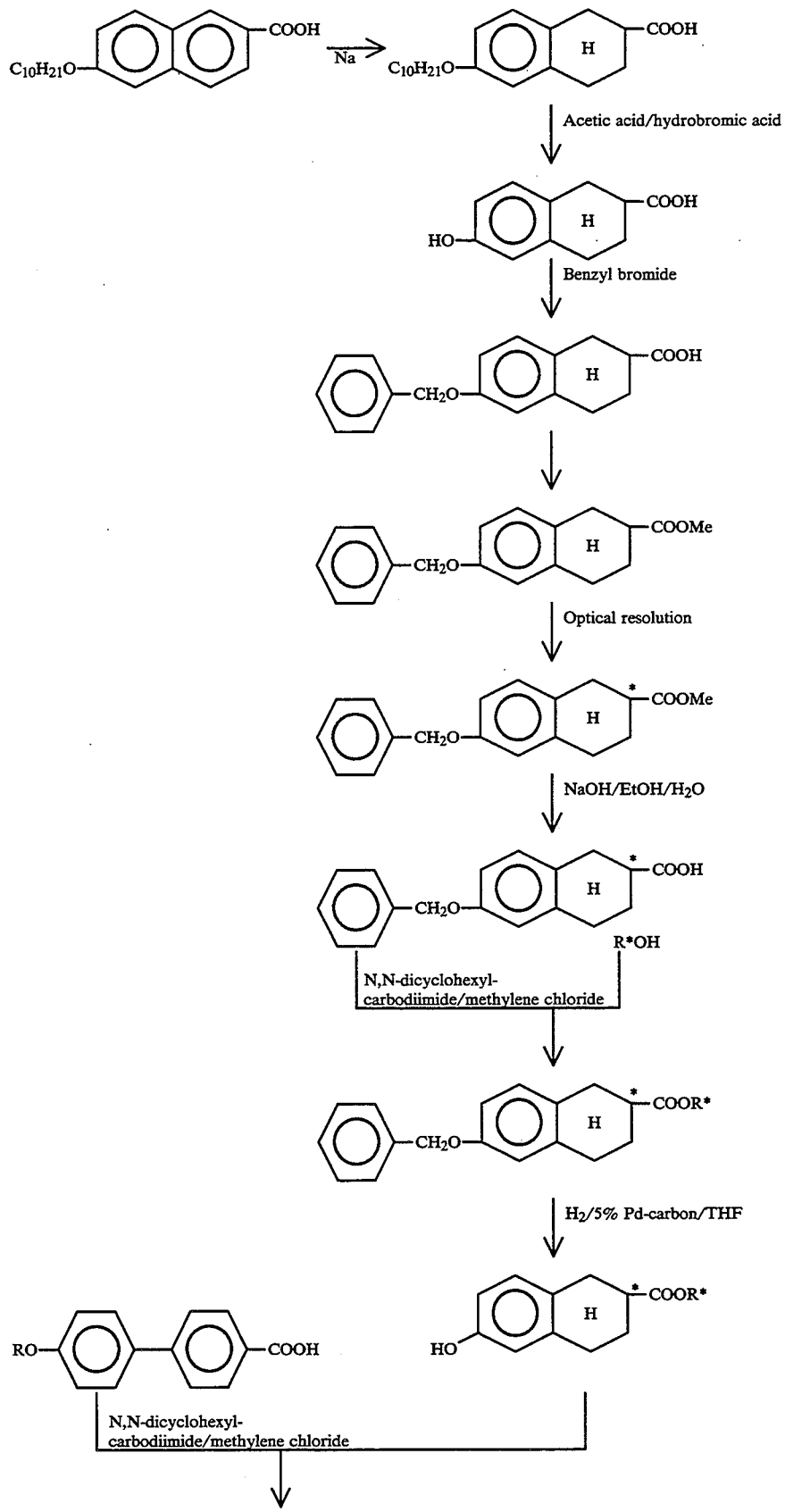

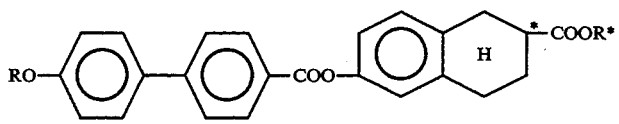

That is, for example, a mixture of 6-alkoxynaphthalene-2-carboxylic acid and 1,2-diethoxyethane is refluxed with dropwise adding thereto isoamyl alcohol in the presence of metallic sodium, to obtain 1,2,3,4-tetrahydro-6-alkoxynaphthalene-2-carboxylic acid that is a racemic modification.

The 1,2,3,4-tetrahydro-6-alkoxynaphthalene-2-carboxylic acid thus obtained is caused to react with acetic acid and hydrobromic acid, to obtain 1,2,3,4-tetrahydro-6-hydroxynaphthalene-2-carboxylic acid.

The 1,2,3,4-tetrahydro-6-hydroxynaphthalene-2-carboxylic acid obtained in the above is caused to react with benzyl bromide in the presence of potassium hydroxide, to obtain 1,2,3,4-tetrahydro-6-benzyloxynaphthalene-2-carboxylic acid. The compound thus obtained is heated under reflux in the presence of an acid catalyst to obtain 1,2,3,4-tetrahydro-6-benzyloxynaphthalene-2-carboxylic acid methyl ester.

The 1,2,3,4-tetrahydro-6-benzyloxynaphthalene-2-carboxylic acid methyl ester thus obtained, which is a racemic modification, is optically resolved into 1,2,3,4-tetrahydro-6-benzyloxynaphthalene-2-carboxylic acid methyl optically active (+) form and 1,2,3,4-tetrahydro-6-benzyloxynaphthalene-2-carboxylic acid methyl ester of optically active (−) form by means of high-speed liquid chromatography using an optical resolution column. Then, each of the optical active methyl esters was hydrolysed to obtain an optical active 1,2,3,4-tetrahydro-6-benzyloxynaphthalene-2-carboxylic acid.

The optical resolution may be carried out after synthesis of the 1,2,3,4-tetrahydro-6-alkoxynaphthalene-2-carboxylic acid methyl ester in the same manner as above instead of carrying it out in the above-mentioned stage.

Then, the optically active 1,2,3,4-tetrahydro-6-benzyloxynaphthalene-2-carboxylic acid thus obtained is caused to react with an optically active alkylalcohol, which is separately synthesized, using methylene chloride as a solvent in the presence of 4-N,N-dimethylaminopyridine while a solution of N,N'-dicyclohexylcarbodiimide is dropwise added, to obtain optically active 1,2,3,4-tetrahydro-6-benzyloxynaphthalene-2-carboxylate.

The optically active 1,2,3,4-tetrahydro-6-benzyloxynaphthalene-2-carboxylate thus obtained is introduced into a solvent such as tetrahydrofuran and reduced with a hydrogen gas in the presence of a reducing catalyst such as palladium/carbon, to obtain optically active 1,2,3,4-tetrahydro-6-hydroxynaphthalene-2-carboxylate.

Then, the optically active 1,2,3,4-tetrahydro-6-hydroxynaphthalene-2-carboxylate thus obtained is caused to react with 4-alkoxybiphenylcarboxylic acid using methylene chloride as a solvent in the presence of 4-N,N-dimethylaminopyridine while a solution of N,N'-dicyclohexylcarbodiimide is dropwise added, to obtain a tetralin compound that is a liquid crystal material having at least two optically active carbon atoms.

The above-mentioned process is given as an example of processes for preparing liquid crystal materials of the invention, and it should be construed that the liquid crystal materials of the invention are in no way limited to those prepared by this process.

For example, in order to resolve the optical isomer, there are other methods than the above-mentioned high-speed liquid chromatography using an optical resolution column, such as a method of preferential crystallization comprising adding crystal (i.e., seed crystal) of an optically active substance to a saturated solution of racemic modification to accelerate crystallization so as to obtain an optically active substance, and a method comprising preparing a diastereomer salt from a racemic modification (acid) and an optically active base, resolving the diastereomer salt into a pure diastereomer salt by recrystallization and decomposing the salt with an acid or an alkali to obtain an optically active substance. Any of these methods can be applied to the present invention.

The tetralin compound of the formula [I] which is obtained as above can be used as a liquid crystal material.

Particularly, the tetralin compound having optical activity can be used as a ferroelectric liquid crystal compound or an antiferroelectric liquid crystal compound.

Of such tetralin compounds which can be prepared by the above method, the following compounds [14] and [15] show markedly excellent liquid crystal characteristics.

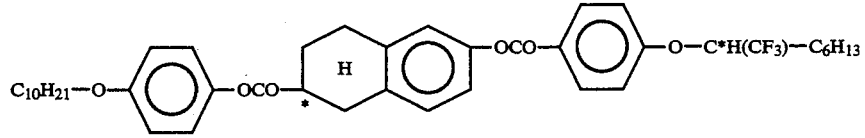

[14−]

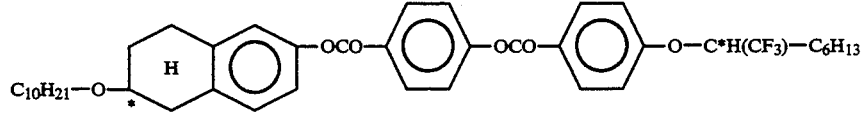

[15−]

Further, one aspect of the present invention is also to provide tetralin compounds, namely carboxylic acid ester compounds represented by the following formulae (L) and (M), which are especially suitable for the liquid crystal material of the present invention.

One carboxylic acid ester compound of the present invention is represented by the following formula (L);

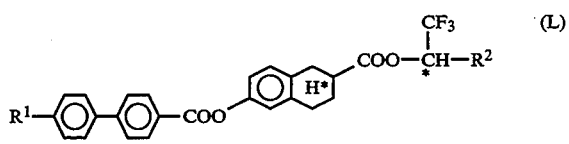

In the above formula (L), $R^1$ is an alkyl or alkoxy group having 8-14 carbon atoms and $R^2$ is an alkyl group in which one of —$CH_2$— group may be substituted with —O— group or —COO— group. Further, in the carboxylic acid compound of the present invention, an angle of rotation caused by an optical active structure having the chiral center which is one of the carbon atoms in the tetralin ring of said material is (−).

The other carboxylic acid ester compound of the present invention is represented by the following formula (M);

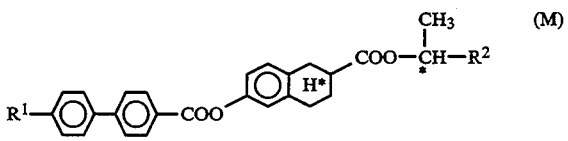

In the above formula (M), $R^1$ and $R^2$ are the same as described above and an angle of rotation caused by an optical active structure having the chiral center which is one of the carbon atoms in the tetralin ring of said material is (+).

Of such carboxylic acid ester compounds, the following compounds [98−], [104−], [109−], [202+], [164−], [170] and [186−] show markedly excellent crystal characteristics.

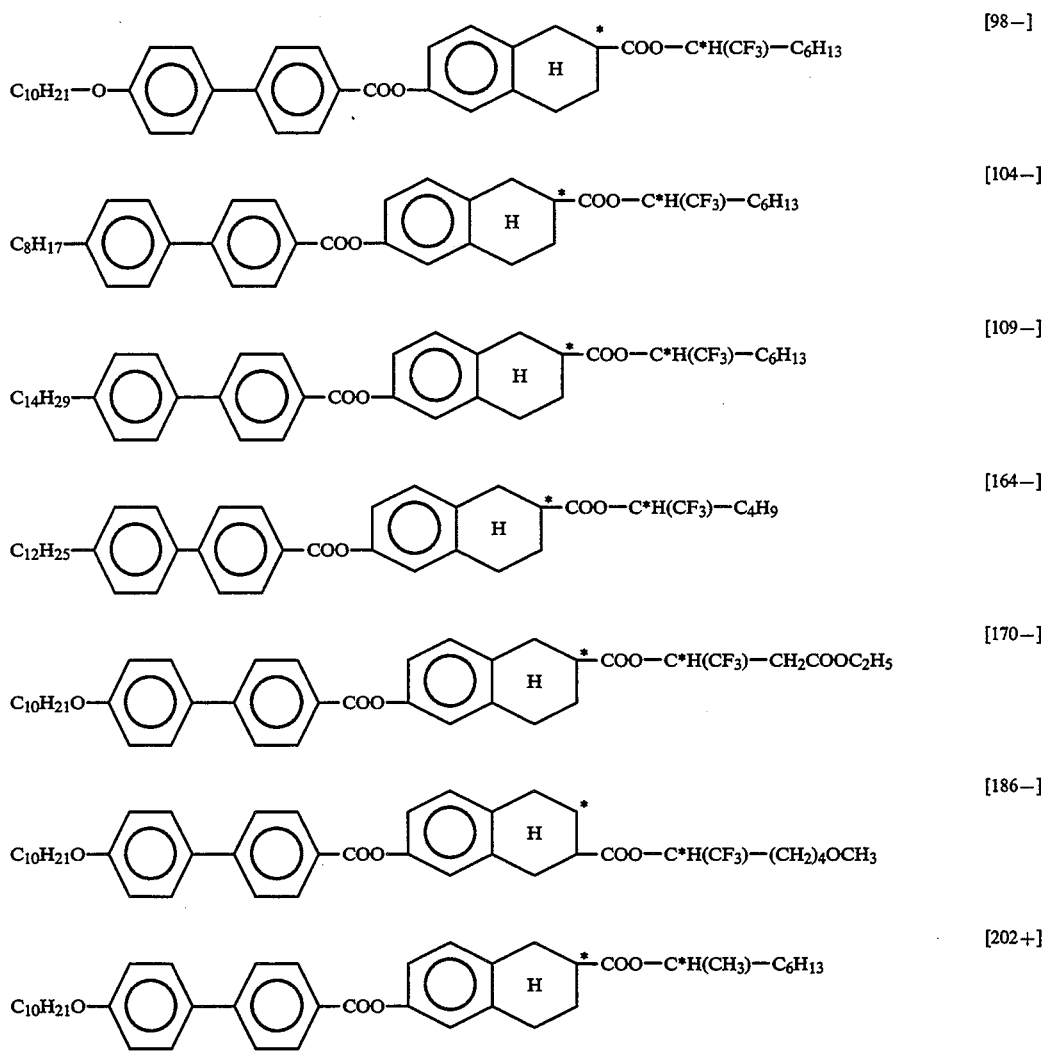

In the liquid crystal materials of the invention, there are many compounds capable of being in a smectic phase within a wide temperature range. However, any liquid crystal material capable of being in a smectic phase within a wide temperature range when a compound showing liquid crystal characteristics is used singly, as in the case of the above-mentioned compound, has been scarcely known so far.

The liquid crystal material of the invention has a wide temperature range where the liquid crystal material is in a smectic phase. Further, a liquid crystal element filled with such liquid crystal material, for example, an optical switching element, is excellent in the high-speed response properties.

The liquid crystal material of the invention may be used singly, or may be mixed with another liquid crystal compound and used as a composition. For example, the liquid crystal material of the invention may be used either as a main ingredient of a ferroelectric liquid crystal composition or an antiferroelectric liquid crystal composition, or as an assistant of a liquid crystal composition containing as a main ingredient another liquid crystal compound capable of being in a smectic phase. That is, the liquid crystal material of the invention capable of being in a smectic phase can be used as a main ingredient of a liquid crystal composition or as an assistant Of a liquid crystal composition containing another liquid crystal compound as a main ingredient. The liquid crystal material not capable of being in a smectic phase can be used as an assistant of a liquid crystal composition containing another liquid crystal material as a main ingredient.

Examples of the liquid crystal compounds which can be used in combination with the liquid crystal material of the invention represented by the formula [I] include:
(+)-4'-(2''-methylbutyloxy)phenyl-6-octyloxynaphthalene-2-carboxylate,
4'-decyloxyphenyl-6-((+)-2''-methylbutyloxy)naphthalene-2-carboxylate,
liquid crystal compounds such as

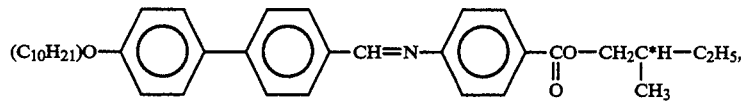

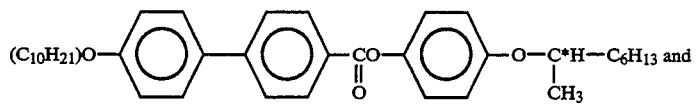

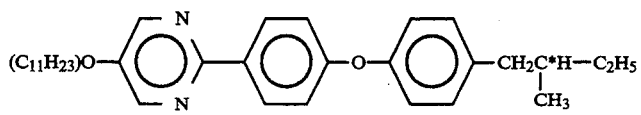

and
such compounds each having a cyclic structure and an optical activity as

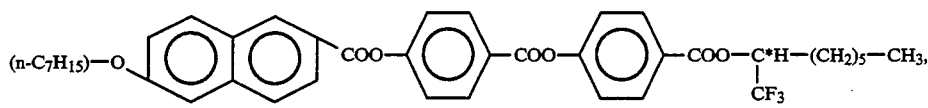

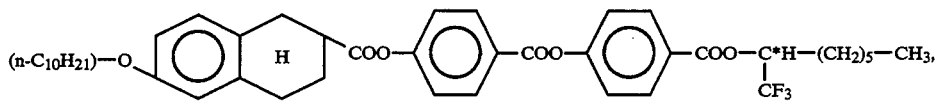

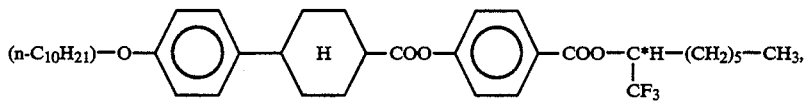

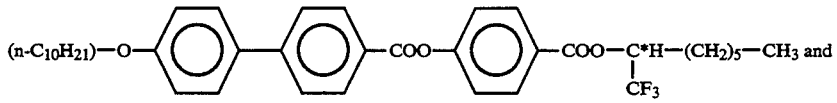

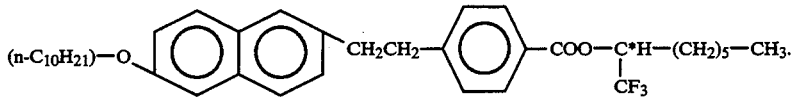

Examples of the liquid crystal compounds may also include:
Shiff base liquid crystal compounds such as

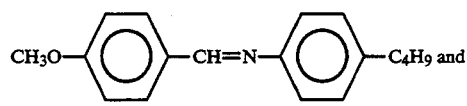

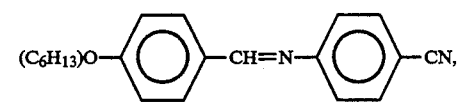

azoxy liquid crystal compounds such as

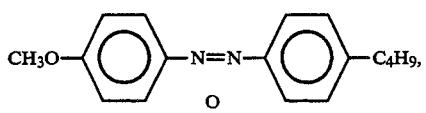

benzoic acid ester liquid crystal compounds such as

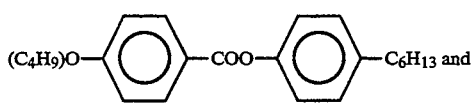

cyclohexylcarboxylic acid ester liquid crystal compounds such as

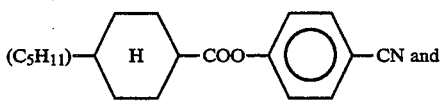

biphenyl liquid crystal compounds such as

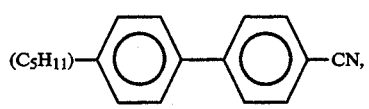

terphenyl liquid crystal compounds such as

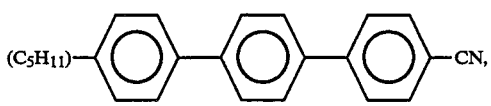

cyclohexyl liquid crystal compounds such as

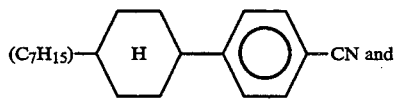

and
pyrimidine liquid crystal compounds such as

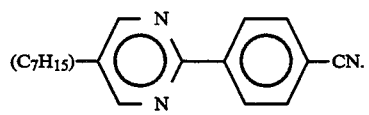

The liquid crystal composition of the present invention contains the liquid crystal material represented by the formula [I] and other compounds such as the above-exemplified compounds. Though the amount of the liquid crystal material represented by the formula [I] to be added can be optionally determined while the characteristics, etc. of the resultant liquid crystal composition are taken into consideration, the liquid crystal material of the formula [I] is used in the composition of the invention in an amount of usually 1 to 99 parts by weight, preferably 5 to 75 parts by weight, based on 100 parts by weight of the total amount of the liquid crystal components in the composition.

The liquid crystal composition may contain additives which are incorporated into conventional liquid crystal compositions, such as a conductivity-imparting agent and a life-extending agent, in addition to the liquid crystal material of the invention.

The liquid crystal composition of the invention can be prepared with the liquid crystal material represented by the formula [I] and, if desired, other liquid crystal materials and additives which are mixed together.

The liquid crystal composition containing the above-mentioned liquid crystal material shows an optical switching phenomenon when a voltage is applied, and hence display devices having a good response can be manufactured by utilizing this phenomenon. Liquid crystal elements in which this phenomenon is utilized and methods for driving the elements utilizing this phenomenon can be referred to, for example, Japanese Patent Laid-Open Publications No. 107216/1981 and 118744/1981.

Although there can be used compounds capable of being in smectic C, F, G, H, I, J and K phases as liquid crystal materials for such display devices, display devices in which liquid crystal compounds other than those in a smectic C phase are incorporated generally show a slow (low) response speed. For this reason, driving of liquid crystal elements in which a liquid crystal material in a smectic C phase is incorporated has been considered to be effective from the viewpoint of practical use.

However, the liquid crystal material of the invention can be used not only in a smectic C phase but also in a smectic A phase by utilizing such a method for driving a display device in which a liquid crystal material in a smectic A phase is incorporated as has been already proposed by the present inventors in Japanese Patent Laid-Open Publication No. 918/1990. That is to say, utilization of the driving method makes it possible to drive the liquid crystal element of the invention in a wide range and to increase the electrooptical response speed of the element.

Figure 14:
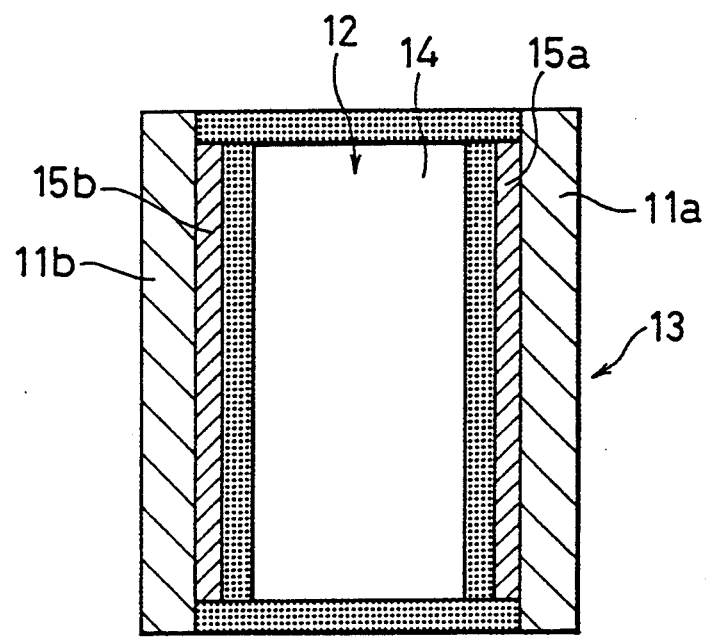
FIG. 14 is a schematic sectional view of an embodiment of a liquid crystal element according to the present invention.

The liquid crystal element of the present invention comprises a cell filled with the liquid crystal material and polarizing plates. In detail, the liquid crystal element of the invention comprises, as shown in FIG. 14, a cell 13 composed of two transparent substrates 11a, 11b so arranged as to form a gap 14 therebetween to be filled with a liquid crystal material 12 and two transparent electrodes 15a, 15b each formed on each of the surfaces of the two transparent substrates 11a, 11b, said surfaces facing the liquid crystal material 12, the liquid crystal material 12 filled in the gap 14 of the cell 13, and two polarizing plates (not shown) arranged on each outer side of the cell 13.

In the present invention, glass plates or transparent polymer plates can be used as the transparent substrates.

The transparent substrate has a thickness of usually 0.01 to 1.0 mm when it is a glass plate.

Further, flexible transparent substrates can be also employed as the transparent substrates in the invention. In this case, at least one of the transparent substrates may be a flexible one, or both of them may be flexible ones. As the flexible transparent substrates, polymer films, etc. can be used.

A transparent electrode is provided on the surface of the transparent substrate. The transparent electrode can be formed by coating the transparent substrate surface with, for example, indium oxide or tin oxide. The thickness of the transparent electrode is usually in the range of 100 to 2,000 angstrom.

On the transparent electrode provided on the transparent substrate may be further provided an orientation control layer or a ferroelectric layer. Examples of the orientation control layer include an organic thin film and an inorganic thin film, formed by chemical adsorption of an organosilane coupling agent or a carboxylic acid multinuclear complex. Examples of the organic thin film include thin films of polymers such as polyethylene, polypropylene, polyester, polyamide, polyvinyl alcohol (Poval) and polyimide.

Examples of the inorganic thin film include thin films of oxides such as silicon oxide, germanium oxide and alumina, thin films of nitrides such as silicon nitride, and other semiconductor thin films.

For imparting orientation properties to such thin films, there can be used a method of imparting anisotropy or shape specificity to the films during the formation of the films and a method of imparting orientation properties from outside after forming the thin films. In more detail, there can be mentioned a method of coating the transparent electrode with a polymer material such as a polyimide resin to form a thin film and then rubbing the thin film in one direction, a method of stretching a polymer film to impart orientation properties, and a method of depositing an oxide by rhombic deposition.

Two of the transparent substrates each having the transparent electrode are arranged in such a manner that the two transparent electrodes face each other and a gap to be filled with a liquid crystal material is formed between the two transparent substrates. The width of the gap thus formed is in the range of usually 1 to 10 μm, preferably 1 to 5 μm. The gap can be formed, for example, by arranging the two substrates in such a manner that they hold a spacer therebetween. As the spacer, there can be used, for example, a polyimide type polymer material obtained by patterning a photosensitive polyimide precursor. By the use of the spacer, a monodomain is formed by interfacial effect between the spacer and the liquid crystal material.

Figure 15:
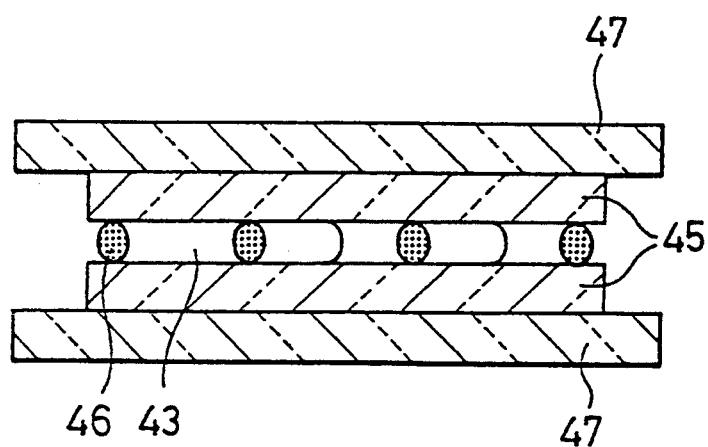
FIG. 15 is a sectional view of another embodiment of a liquid crystal element according to the present invention in which fibers are used as a spacer.

As shown in FIG. 15, fibers 46 are placed in a liquid crystal material 43 and used as a spacer which is different from the above-mentioned spacers. By the use of the fibers 46, transparent substrates 47 each having a transparent electrode 45 can be held to form a gap having a constant width.

In place of or together with the above-mentioned fibers, particulate matters may also be employed. Examples of the particulate matters include particles of melamine resin, urea resin and benzoguanamine resin having a diameter of 1 to 10 μm.

The two transparent substrates so arranged as to form a gap therebetween in the manner as described above are then generally sealed with a sealing material along their peripheries to be bonded. Examples of the sealing material include epoxy resin and silicone resin, and they may be modified with acrylic rubber, silicone rubber, etc.

The gap of the liquid crystal cell having the above-mentioned structure is filled with a liquid crystal material comprising the compound represented by the formula [I].

The liquid crystal material filled in the gap of the liquid crystal cell can be orientated, for example, by a temperature gradient method in which a spacer edge is utilized or a monoaxial orientation control method such as a surface treatment using an orientation film. In the present invention, moreover, an initial orientation of the liquid crystal material can be also conducted by applying an electric field formed as a result of applying a direct current bias voltage to the liquid crystal material while the material is heated.

Figure 16:
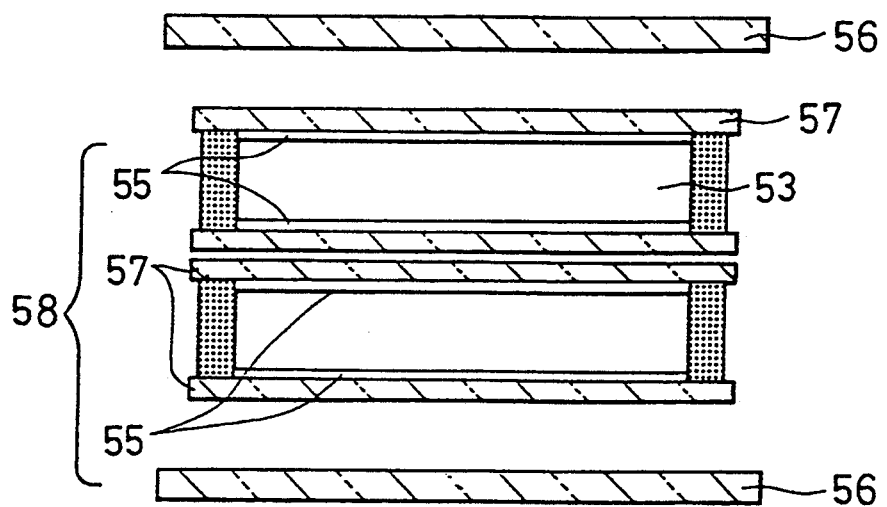
FIG. 16 is a sectional view of another embodiment of a liquid crystal element according to the present invention in which a cell is arranged between two polarizing plates.

The liquid crystal cell filled with the liquid crystal material and initially orientated as described above is placed between two polarizing plates. As shown in FIG. 16, two or more of cells 58 each comprising two transparent substrates 57, transparent electrodes 55 and a liquid crystal material 53 as described above may also be placed between the two polarizing plates 56.

In the liquid crystal element of the invention, the two polarizing plates are arranged in such a manner that two polarizing planes of the polarizing plates makes an angle of 70° to 110° Preferably, these two polarizing plates are arranged so that the polarizing directions of the polarizing plates meet at right angles, that is, the above-mentioned angle becomes 90°.

Examples of such polarizing plates include resin films such as polyvinyl alcohol films and polyvinyl butyral films to which polarizing properties are imparted by stretching these films in the presence of iodine, etc. to allow the films to absorb iodine. These polarizing films may be coated with another resin to form a multi-layer structure.

In the present invention, between the two polarizing plates arranged as above can be placed the liquid crystal cell in such a manner that the cell forms an angle (rotation angle) within the range of ±10° from the state where the transmitted light is minimized in its amount (i.e., the darkest state), preferably the cell produces the darkest state. Alternatively, between the two polarizing plates arranged as above can be placed the liquid crystal cell in such a manner that the cell forms an angle (rotation angle) within the range of ±10° from the state where the transmitted light is maximized in its amount (i.e., the brightest state), preferably the cell produces the brightest state.

As shown in FIG. 14, the liquid crystal element of the invention can be manufactured by filling the gap 14 of the cell 13 with the liquid crystal material 12 and initially orientating the liquid crystal material 12.

The liquid crystal material 12 is usually heated until it becomes molten and filled (poured) into the gap 14 of the cell 13 kept at a reduced pressure while the liquid crystal material 15 is in the molten state. After filling the liquid crystal material, an inlet for the liquid crystal material provided in the cell is sealed.

Then, the cell whose inlet is sealed is heated to a temperature not lower than the temperature at which the liquid crystal material 12 filled in the cell begins to show an isotropic phase, and then cooled to a temperature at which the liquid crystal material 12 begins to show a liquid crystal phase.

In the present invention, the cooling is conducted at a cooling rate of preferably not more than 2° C./min, more preferably 0.1° to 2.0° C./min, particularly preferably 0.1 to 0.5° C./min. As a result of cooling the cell 13 at such cooling rate, the initial orientation condition of the liquid crystal material 12 is improved, and hence a liquid crystal element having a liquid crystal phase which is almost free from orientation defects and is composed of a monodomain can be easily formed. The term "initial orientation" designates a state where the liquid crystal material is arranged before changing the orientation vector of the liquid crystal material by means of, for example, application of an electric voltage to the liquid crystal material.

The liquid crystal element of the invention thus formed is prominently excellent in properties such as contrast as compared with conventional liquid crystal elements, and hence it can be appropriately used as a surface stabilized ferroelectric liquid crystal element, a helically modulated element, an excessively scattered element, a guest-host element, a vertically orientated liquid crystal element, etc.

The liquid crystal element of the invention can be driven, for example, by applying thereto an electric field controlled to have a frequency of usually 1 Hz to 100 kHz, preferably 10 Hz to 10 kHz, and a voltage of usually 0.01 to 60 Vp-p/$\mu m^t$ (voltage per 1 $\mu m$ in thickness), preferably 0.05 to 30 Vp-p/$\mu m^t$.

When the liquid crystal element of the invention in which the liquid crystal material represented by the formula [I] is incorporated is used, the amount of the light transmitted by the liquid crystal element comes to exhibit two kinds of hysteresis curves by changing a width of a wave form (driving wave) of the electric field applied for driving the liquid crystal element. That is, there are two driving methods. One is a driving method utilizing so-called bistability, and the other is a driving method utilizing so-called tristability.

When the liquid crystal element of the invention is prepared by arranging a liquid crystal cell filled with an optically active liquid crystal material between two polarizing plates whose polarizing planes meet at right angles so that the element attains the darkest state without application of an electric field, the liquid crystal element can be driven, for example, by applying a rectangular wave (or pulse wave), a triangular wave, a sinusoidal wave or a wave form in combination of these waves at a frequency of 50 Hz to 100 kHz, preferably 70 Hz to 10 kHz. For example, when a rectangular wave (or pulse wave or both in combination) is applied to the liquid crystal element, the speed for driving the liquid crystal element can be increased by making the width of the electric field hoe more than 10 msec, preferably 0.01 to 10 msec. In this region, the liquid crystal element of the invention can be used as a bistable one. Further, the liquid crystal element of the invention can be used as a tristable one in the region where the driving speed is not required to be so high by making the width of the electric field more than 10 msec, preferably 33 to 1,000 msec. The width of the electric field signifies, for example, in rectangular waves, the length (namely, period) of the electric field maintained at a predetermined voltage.

By the use of the liquid crystal elements of the invention, various liquid crystal display devices and electrooptical display devices can be manufactured. Moreover, of the liquid crystal elements of the invention, those filled with a liquid crystal material capable of being in a smectic phase can be used for manufacturing liquid crystal display devices and electrooptical display devices, such as storage type liquid crystal display devices including thermal write type liquid crystal display elements and laser write type liquid crystal display elements. Furthermore, by the use of the liquid crystal materials showing antiferroelectricity and having optically active carbon atoms in the tetralin ring and the hydrocarbon chain structure portion, optical switching elements such as optical shutters or liquid crystal printers, and liquid crystal display devices or electrooptical display devices such as piezoelectric elements and pyroelectric elements can be manufactured.

That is to say, the liquid crystal material used for the liquid crystal element of the invention exhibits tristability or bistability, and hence the liquid crystal element can be allowed to have an optical switching function or a display function by reversing the electric field so that it attains bistability.

When the liquid crystal material exhibits bistability, it has spontaneous polarization, and hence if once a voltage is applied to the liquid crystal element of the invention, the element keeps memory effect even after application of the electric field is stopped. That is, it is unnecessary to continuously apply the electric field to the liquid crystal element for the purpose of maintaining the memory, and therefore, use of a display device in which the liquid crystal element of the invention is used makes it possible to reduce power consumption. Also a liquid crystal element in which the liquid crystal material exhibiting tristability is incorporated can keep memory effect. Further, a display device in which such liquid crystal element is used shows stable contrast, and hence a displayed image is very sharp.

In the case of using the switching element of the invention incorporating the liquid crystal material represented by the formula [I], a switching operation can be performed by only altering the orientation direction of the molecule. In this case, the first term of an intensity of the electric field applied to the switching element acts on driving of the element, and therefore the element can be driven at a low voltage.

This switching element realizes a high speed response of not longer than several tens of microseconds, thereby to significantly shorten the operation time of the element. Accordingly, use of the liquid crystal element of the invention makes it possible to manufacture a display device (a liquid crystal display device) having a large screen with many scanning lines. The display device can be driven at room temperature or at a temperature not higher than room temperature, and therefore the device can be driven without any auxiliary means for controlling the driving temperature.

The display device in which the liquid crystal element of the invention is used can be driven by various methods, and examples of the driving methods are described below.

A first method is a method in which the liquid crystal element of the invention is placed between two polarizing plates and an external voltage is applied to the liquid crystal element. As a result, the orientation vector of the liquid crystal material is altered, and the alteration of the orientation vector produces birefringence of light in the liquid crystal material. In this method, display is carried out by utilizing polarization of the two polarizing plates and the birefringence.

A second method is a method in which a liquid crystal material added thereto a dichroic dye is used, and which utilizes the dichroism of the dyes. In this method, display is achieved by changing the orientation direction of the liquid crystal compound to change the absorption wavelength of light by the dye. Examples of the dichroic dye include azo dye, naphthoquinone dye, cyanine dye and anthraquinone dye.

The display device manufactured by using the liquid crystal element of the invention can be driven by static driving, simple matrix driving and composite matrix driving, in electric address display system, optical address display system, thermal address display system, or optical beam display system.

Figure 17A:
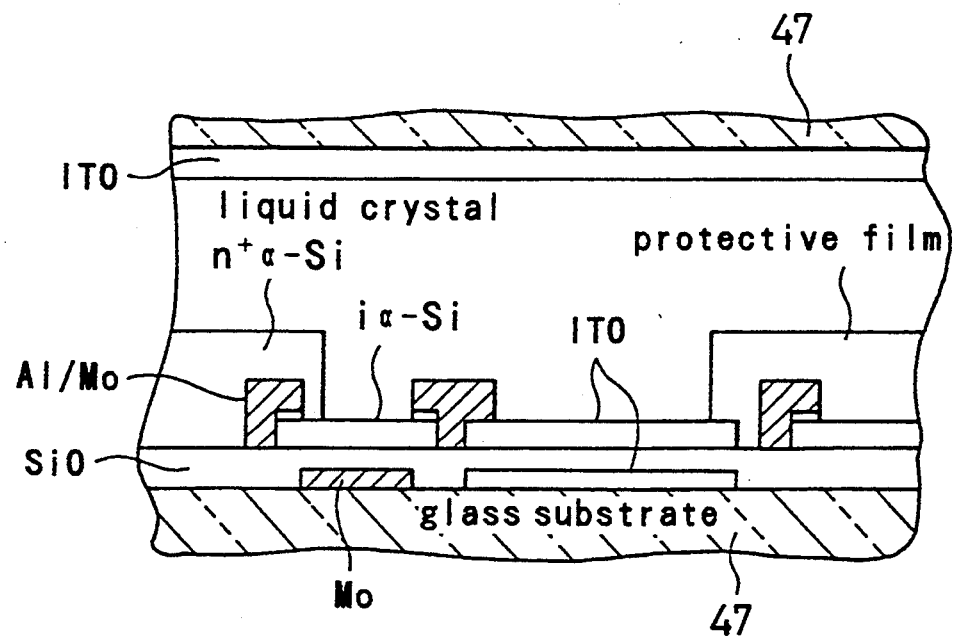
FIG. 17(a) is a schematic view showing one embodiment of a nonlinear element.
Figure 17B:
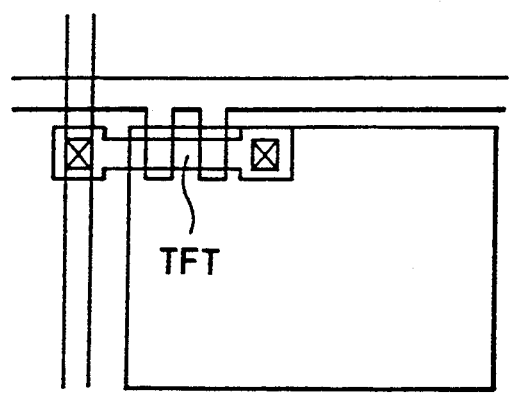
FIG. 17(b) is a schematic view showing one embodiment of a three-terminal element.

When the display device of the invention is driven by application of an electric field, a nonlinear element or an active element can be used as an element for driving each pixel. Examples of two-terminal nonlinear elements include an element having a varistor, a MIM (Metal Insulator Metal), a diode, etc. arranged on one of the transparent substrates and utilizing nonlinearity of these parts, as shown in FIG. 17(a). Examples of three-terminal active elements include an element in which a TFT (thin film transistor), a Si-MOS (Si-metal oxide semiconductor field effect transistor) and a SOS (silicon on Sapphire), etc. are arranged to pixels, as shown in FIG. 17(b).

EFFECT OF THE INVENTION

The liquid crystal materials of the invention have such a structure that dipole moments caused by two chiralities strengthens each other thereby to increase the spontaneous polarization. Hence, liquid crystal elements in which the liquid crystal materials of the invention are incorporated can be made higher in the response speed.

Moreover, the liquid crystal materials of the invention have a good linearity, and hence they are excellent in the liquid crystal characteristics (crystallizability) and can be in a liquid crystal phase even at high temperatures. As a result, the operating temperature range of the liquid crystal can be widened.

Further, since the liquid crystal materials of the invention are excellent in the orientation properties, and in linearity of the molecules, the liquid crystal materials are much more improved in the orientation properties. Accordingly, liquid crystal elements manufactured by using the liquid crystal materials of the invention show a high contrast.

By the use of a compound having a long helical pitch among the liquid crystal materials of the invention, a liquid crystal elements can be easily manufactured because excellent switching performance can be maintained even if the cell gap of the element is widened.

When to the liquid crystal material of the invention is added the same and/or other kinds of liquid crystal materials, the operating temperature range of the liquid crystal can be widened without deteriorating ferroelectricity or antiferroelectricity of the liquid crystal material of the invention.

Accordingly, use of such liquid crystal material makes it possible to obtain a liquid crystal element having a high response speed in a wide temperature range.

Further, when such liquid crystal element is used in a liquid crystal display device, the operating time of the display device can be markedly shortened. By the use of such display device, power consumption can be prominently reduced, a high and stable contrast can be obtained, and driving at a low voltage is available.

In the case where the liquid crystal materials of the invention each having a tetralin ring are used as antiferroelectric liquid crystal compounds, realization of the memory effect can be easily made, and orientation properties, etc. can be improved.

When the liquid crystal material of the invention is used as a ferroelectric liquid crystal compound, it can be realized to obtain high response speed by using an optical active material rather than a racemic material. The high response speed may be obtained by the reason that the specific optical active structure of the molecule in the liquid crystal material makes the spontaneous polarization higher and, therefore, improves the response properties of the molecule to an applied voltage.

By the use of such liquid crystal materials of the invention, there can be obtained various devices having excellent characteristics such as a wide operating temperature range, a high switching speed, a decreased power consumption and a stable contrast.

EXAMPLE

The present invention is further described with reference to examples, but it should be construed that the invention is in no way limited to those examples.

In the examples, R and S denote R-form and S-form of an optically active substance, respectively. Further, (+) or (−) given to the resulting compound does not denote the optical rotatory power thereof, but denotes the optical rotatory power of a tetralin compound having been used as a material for preparing the resulting compound.

EXAMPLE 1

Synthesis of an ester compound of 6-[4'-(4''-decyloxy)-biphenylcarbonyloxy]-(+)-1,2,3,4-tetrahydronaphthalene-2-carboxylic acid (starting material: (+)-1,2,3,4-tetrahydronaphthalene-6-benzyloxy-2-carboxylic acid) and (R)-1-trifluoromethylheptanol

First step

To a mixture of 3.86 g (11.8 mmol) of 6-decyloxynaphthalene-2-carboxylic acid and 130 ml of 1,2-diethoxyethane was added 3.0 g (130 mg atom) of metallic sodium in a nitrogen atmosphere at 120° C. with stirring, and the resulting mixture was heated up to a reflux temperature.

To the mixture was dropwise added 10 g (114 mmol) of isoamyl alcohol over a period of 1 hour, and the resulting mixture was allowed to react under reflux for additional 11 hours. After the reaction mixture was cooled to room temperature, to the mixture was added ethanol to change the remaining metallic sodium into inert alcoholate. Then, the reaction mixture was acidified with 20% hydrochloric acid.

After addition of 100 ml of water to the reaction mixture, the resulting organic phase was separated and washed with water.

The organic phase was concentrated under a reduced pressure to obtain 4.25 g of a solid. The solid was recrystallized with toluene to obtain 2.95 g (8.89 mmol) of 1,2,3,4-tetrahydro-6-decyloxynaphthalene-2-carboxylic acid.

Second step 16.6 g (50 mmol) of the 1,2,3,4-tetrahydro-6-decyloxynaphthalene-2-carboxylic acid obtained in the first step, 250 ml of acetic acid and 86.5 g (0.5 mol) of 47% hydrobromic acid were heated at 130° C. under reflux for 7 hours. After addition of distilled water to the resulting mixture, the mixture was concentrated under a reduced pressure to obtain 10.60 g (50 mmol) of 1,2,3,4-tetrahydro-6-hydroxynaphthalene-2-carboxylic acid. This carboxylic acid compound is a mixture of S-form and R-form (racemic modification).

Third step

A mixture of 10.60 g (50 mmol) of the (+)-1,2,3,4-tetrahydro-6-hydroxynaphthalene-2-carboxylic acid obtained in the second step, 12.85 g (75 mmol) of benzyl bromide, 6.6 g (100 mmol) of 85% potassium hydroxide, 0.525 g (3.5 mmol) of sodium iodide, 200 ml of ethanol and 25 ml of distilled water was heated at 100° C. under reflux for 12 hours. To the mixture was added 50 ml of 10% potassium hydroxide, and the resulting mixture was heated under reflux for another 2 hours. The mixture was allowed to stand for cooling to room temperature and then introduced into cold water. Thereafter, the reaction mixture was acidified with 3.6% hydrochloric acid.

The resulting precipitate was separated by filtration and recrystallized with toluene to obtain 13.08 g (46.4 mmol) of 1,2,3,4-tetrahydro-6-benzyloxynaphthalene-2-carboxylic acid.

Fourth step

To a mixture of 2.82 g (10 mmol) of the 1,2,3,4-tetrahydro-6-benzyloxynaphthalene-2-carboxylic acid obtained in the third step and 50 ml of methanol was added 1 ml (approx. 10 mmol) of hydrochloric acid, and the resulting mixture was refluxed for 4 hours. After the reaction was completed, the mixture was concentrated, and the concentrate was separated and purified by means of column chromatography to obtain 2.90 g (9.8 mmol) of 1,2,3,4-tetrahydronaphthalene-6-benzyloxy-2-carboxylic acid methyl ester.

Fifth Step

The 1,2,3,4-tetrahydronaphthalene-6-benzyloxy-2-carboxylic acid methyl ester obtained in the fourth step was subjected to high-speed liquid chromatography using hexane/isopropanol (8/2) as a developing solvent to obtain two kinds of compounds which had peak areas almost equal to each other and were different in the retention time. When the compounds were examined on the angle of rotation, the angles of rotation of the compounds were (+) and (−), respectively. Hence, each of the compounds was confirmed to be an optically active substance.

Sixth step

To 0.86 g (2.9 mmol) of the optically active (+)-1,2,3,4-tetrahydronaphthalene-6-benzyloxy-2-carboxylic acid methyl ester or the optically active (−)-1,2,3,4-tetrahydronaphthalene-6-benzyloxy-2-carboxylic acid methyl ester obtained in the fifth step were added a mixed solvent of ethanol/water (50 cc/10 cc) and 0.3 g of potassium hydroxide, and the resulting mixture was refluxed for 3 hours. After addition of 300 cc of water, the resulting mixture was acidified with concentrated hydrochloric acid to give a precipitate. The precipitate was filtered to obtain 0.8 g (2.83 mmol) of optically active (+)-1,2,3,4-tetrahydronaphthalene-6-benzyloxy-2-carboxylic acid or optically active (−)-1,2,3,4-tetrahydronaphthalene-6-benzyloxy-2-carboxylic acid.

Seventh step

To a mixture of 5.64 g (20 mmol) of the optically active substance, (+)-1,2,3,4-tetrahydro-6-benzyloxynaphthalene-2-carboxylic acid, obtained in the sixth step, 3.68 g (20 mmol) of (R)-1-trifluoromethylheptanol, 0.244 g (0.2 mmol) of 4-N,N-dimethylaminopyridine and 70 ml of methylene chloride was dropwise added 25 ml of a methylene chloride solution containing 4.53 g (22 mmol) of N,N'-dicyclohexylcarbodiimide over a period of 2 hours at room temperature with stirring.

Further, the resulting mixture was allowed to react for 2 hours at room temperature.

The reaction mixture was filtered, and the filtrate obtained was concentrated. The concentrate was separated by means of column chromatography to obtain 8.19 g (18.3 mmol) of an ester compound of (+)-1,2,3,4-tetrahydro-6-benzyloxynaphthalene-2-carboxylic acid and (R)-1-trifluoromethylheptanol as a white solid.

Eighth step

A hydrogen gas was blown into a mixture of 8.19 g (18.3 mmol) of the ester compound of (+)-1,2,3,4-tetrahydro-6-benzyloxynaphthalene-2-carboxylic acid and (R)-1-trifluoromethylheptanol obtained in the seventh step, 3.6 g of 5% palladium/carbon and 50 ml of tetrahydrofuran at room temperature and normal pressure for 24 hours with stirring.

The reaction mixture was filtered using Celite as a filter aid, and the filtrate obtained was concentrated to obtain 6.78 g (18.3 mmol) of an ester compound of (+)-1,2,3,4-tetrahydro-6-hydroxynaphthalene-2-carboxylic acid and (R)-1-trifluoromethylheptanol as a white solid.

Ninth step

A mixture of 21.4 g (0.1 mol) of 4'-hydroxybiphenyl-4-carboxylic acid, 33.15 g (0.15 mol) of n-decyl bromide, 13.20 g (0.2 tool) of 85% potassium hydroxide, 1.05 g (7 mmol) of sodium iodide, 500 ml of ethanol and 100 ml of distilled water was heated at 100° C. under reflux for 12 hours.

To the mixture was added 40 ml of 25% potassium hydroxide, and the resulting mixture was further heated under reflux for additional 2 hours.

After the reaction mixture was allowed to stand for cooling to room temperature, the mixture was introduced into cold water. Then, the reaction mixture was acidified with 36% hydrochloric acid to precipitate a reaction product.

The precipitate was separated by filtration and dissolved in acetone. The resulting solution was subjected to hot filtration, and the filtrate was concentrated to obtain 1.97 g (6 mmol) of 4'-decyloxybiphenyl-4-carboxylic acid.

Tenth step

To a mixture of 0.35 g (1 mmol) of the 4'-decyloxybiphenyl-4-carboxylic acid obtained in the ninth step, 0.36 g (1 mmol) of the ester compound of (+)-1,2,3,4-tetrahydro-6-hydroxynaphthalene-2-carboxylic acid a 1-trifluoromethylheptanol obtained in the eighth step, 0.012 g (0.1 mmol) of N,N'-dimethylaminopyridine and 10 ml of methylene chloride was dropwise added 5 ml of a methylene chloride solution containing 0.125 g (1.2 mmol) of N,N'-dicyclohexylcarbodiimide over a period of 2 hours at room temperature with stirring. Further, the resulting mixture was allowed to react at room temperature for 48 hours. The reaction mixture was filtered, and the filtrate obtained was concentrated. The concentrate was separated by means of column chromatography to obtain 0.51 g of a colorless semisolid. The M/e value of FD-mass spectrum on the semisolid was 694.

The $^1$H-NMR spectrum of this compound was measured.

FIG. 1 shows the $^1$H-NMR spectrum of the compound.

From the results of the analysis, the compound was identified to be an ester compound of 6-[4'-(4''-decyloxy) biphenylcarbonyloxy]-(+)-1,2,3,4-tetrahydronaphthalene-2-carboxylic acid and (R)-1-trifluoromethylheptanol (exemplified compound [98+]). The structure of this compound is shown below.

terial: (−)-1,2,3,4-tetrahydronaphthalene-2-carboxylic acid and (R)-1-trifluoromethylheptanol.

The M/e value of FD-mass spectrum on the semisolid was 694.

The $^1$H-NMR spectrum of this compound was measured.

Figure 2:
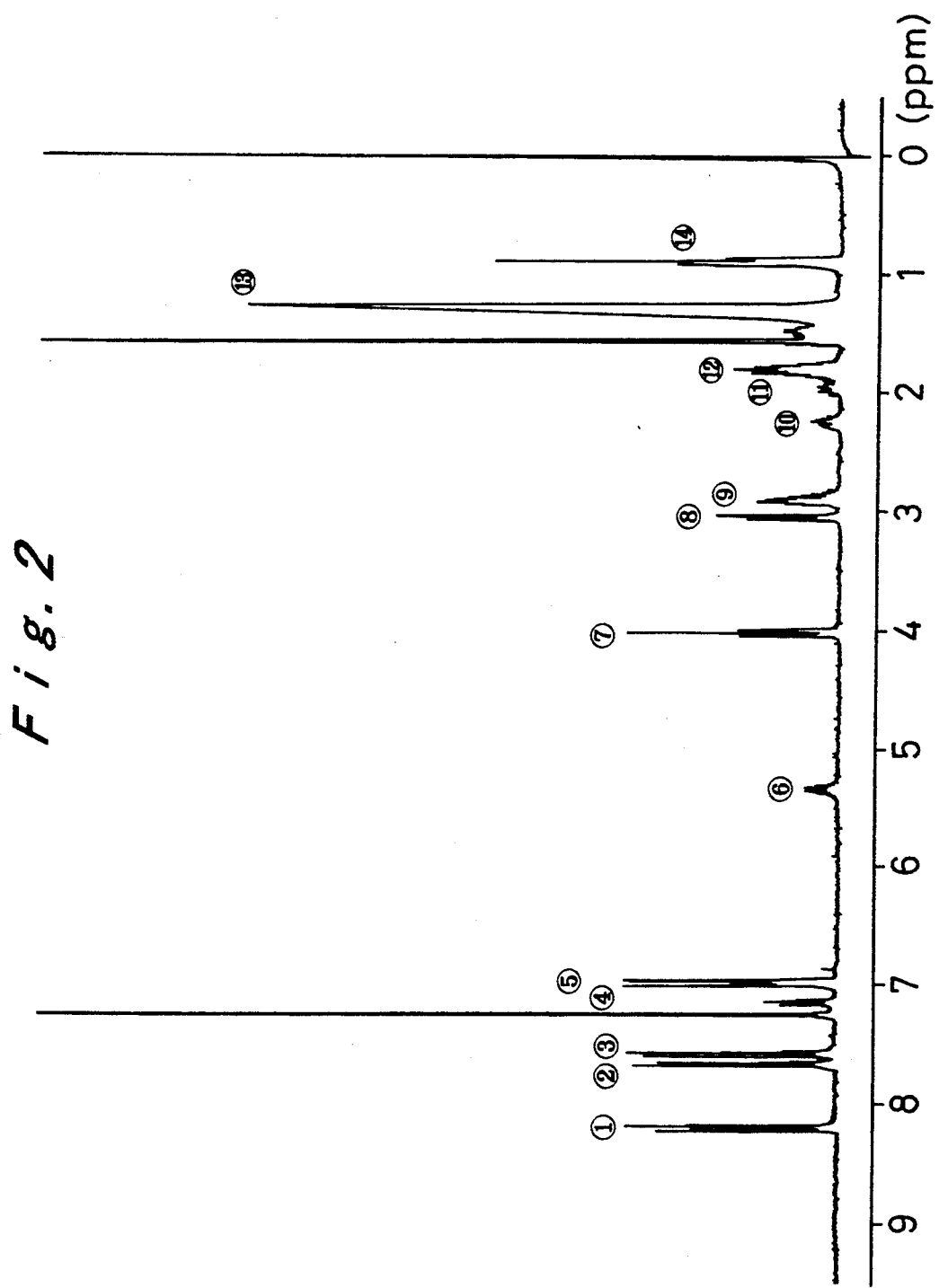

FIG. 2 shows the $^1$H-NMR spectrum of the compound.

From the results of the analysis, the compound was identified to be an ester compound of 6-[4'-(4''-decyloxy) biphenylcarbonyloxy]-(−)-1,2,3,4-tetrahydronaphthalene-2-carboxylic acid and (R)-1-trifluoromethylheptanol (exemplified compound [98-]). The structure of this compound is shown below.

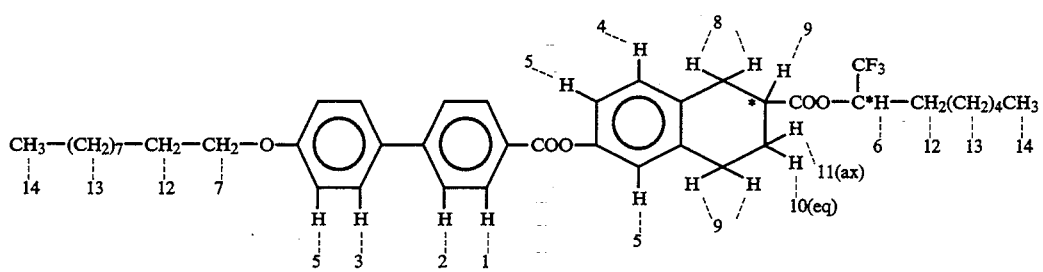

The phase transition temperatures of the above compound are set forth in Table 16.

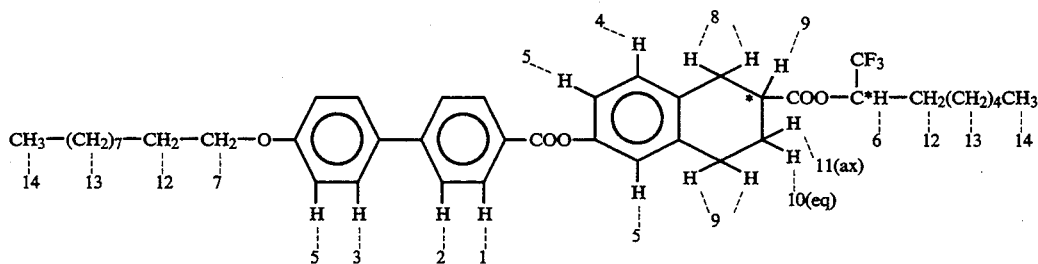

The phase transition temperatures of the above compound are set forth in Table 16.

EXAMPLE 2

Synthesis of an ester compound of 6-[4'-(4''-decyloxy) biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-trifluoromethylheptanol The procedures of Example 1 were repeated except for using (−)-1,2,3,4-tetrahydro-6-benzyloxynaphthalene-2-carboxylic acid in place of the (+)-1,2,3,4-tetrahydro-6-benzyloxynaphthalene-2-carboxylic acid used in the seventh step, to obtain an ester compound of 6-[4'-(4''-decyloxy) biphenylcarbonyloxy]-(−)-1,2,3,4-tetrahydronaphthalene-2-carboxylic acid (starting ma-

Comparative Example 1

Synthesis of an ester compound of 6-[4'-(4''-decyloxy)-biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethylheptanol The procedures of Example 1 were repeated except for using 1,2,3,4-tetrahydro-6-benzyloxynaphthalene-2-carboxylic acid in place of the (+)-1,2,3,4-tetrahydro-6-benzyloxynaphthalene-2-carboxylic acid used, to obtain an ester compound of 6-[4'-(4''-decyloxy) biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethylheptanol (comparative compound [98r]). The structure of this compound is shown below.

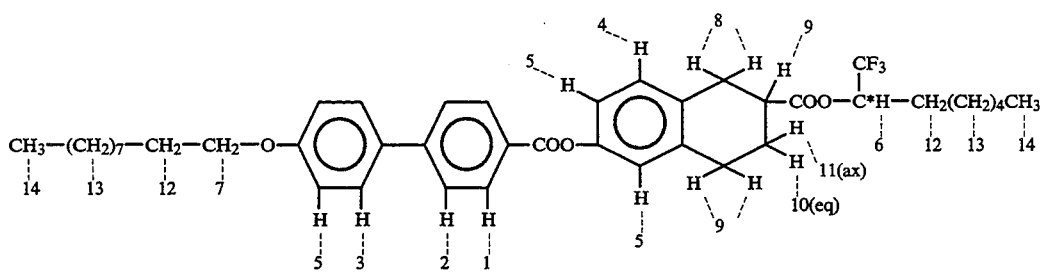

The phase transition temperatures of the above compound are set forth in Table 16.

In each Tables 15–24 in Examples, Cry, SmC$_A$*, SmC*, SmA and Iso denote a crystal phase, an antiferroelectric phase, a ferroelectric phase, a smectic A phase and an isotropic liquid phase, respectively. Further, the symbol . means that the compound can be in the phase, and the symbol — means that the compound cannot be in the phase. Each of the numerals is a phase transition temperature between the phases indicated by the symbol .. The symbol + in a column for Compound No. means that the angle of rotation caused by the chiral molecule of the tetralin ring is +, the symbol − means that the angle of rotation caused by the chiral molecule of the tetralin ring is −, and the character r means a racemic modification. Each of the numerals beneath phase series means a phase transition temperature (° C) between each phases.

The $^1$H-NMR spectrum of this compound was measured.

Figure 3:
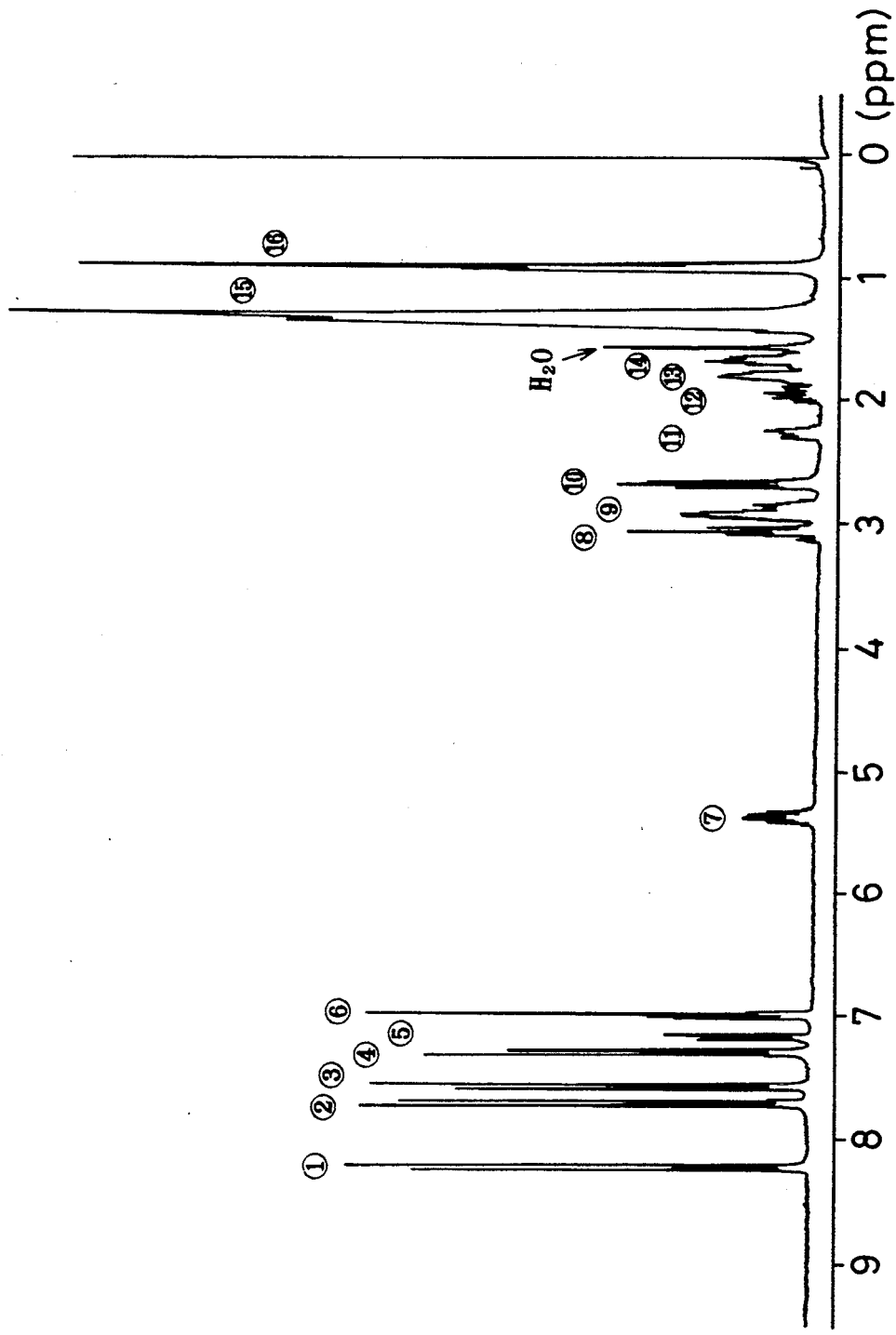

FIG. 3 shows the $^1$H-NMR spectrum of the compound.

From the results of the analysis, the compound was identified to be an ester compound of 6-[4'-(4"-octyl)biphenylcarbonyloxy]-(+)- 1,2,3,4-tetrahydronaphthalene-2-carboxylic acid and (R)-1-trifluoromethylheptanol (exemplified compound [104+]). The structure of this compound is shown below.

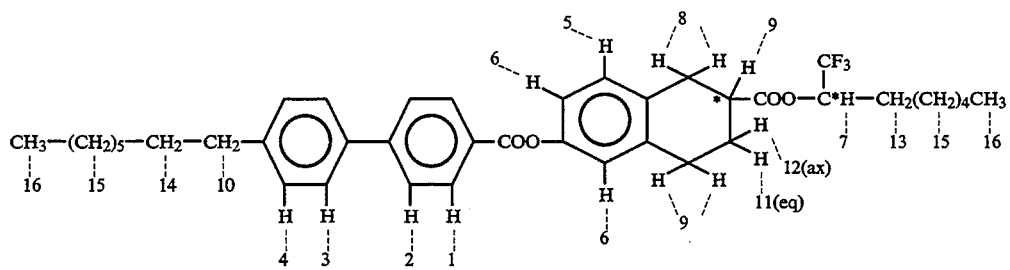

The phase transition temperatures of the above compound are set forth in Table 17.

EXAMPLE 4

Synthesis of an ester compound of 6-[4'-(4"-octyl)biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-tri-

TABLE 16

| | | Phase Series | | | | |
|---|---|---|---|---|---|---|
| Compound No. | Crystal Phase | SmCA* | SmC* | SmX | SmA | Isotropic Liquid Phase |
| Ex. 1 | 98+ | • | 55 • 101 | — | — | • 129 • |
| Ex. 2 | 98− | • | 48 • 92 | • 99 | — | • 129 • |
| Comp. Ex. 1 | 98r | • | 21 • 96 | • 99 | — | • 132 • |

EXAMPLE 3

Synthesis of an ester compound of 6-[4'-(4"-octyl)biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-trifluoromethylheptanol The procedures of Example 1 were repeated except for using octylbiphenyl-4-carboxylic acid (FK-1124-8, available from Teikoku Kagaku K.K.) in place of the decyloxybiphenyl-4-carboxylic acid used in the tenth step, to obtain a colorless semisolid.

The M/e value of FD-mass spectrum on the semisolid was 650.

fluoromethylheptanol

The procedures of Example 3 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The M/e value of FD-mass spectrum on the semisolid was 650.

The $^1$H-NMR spectrum of this compound was measured.

Figure 4:
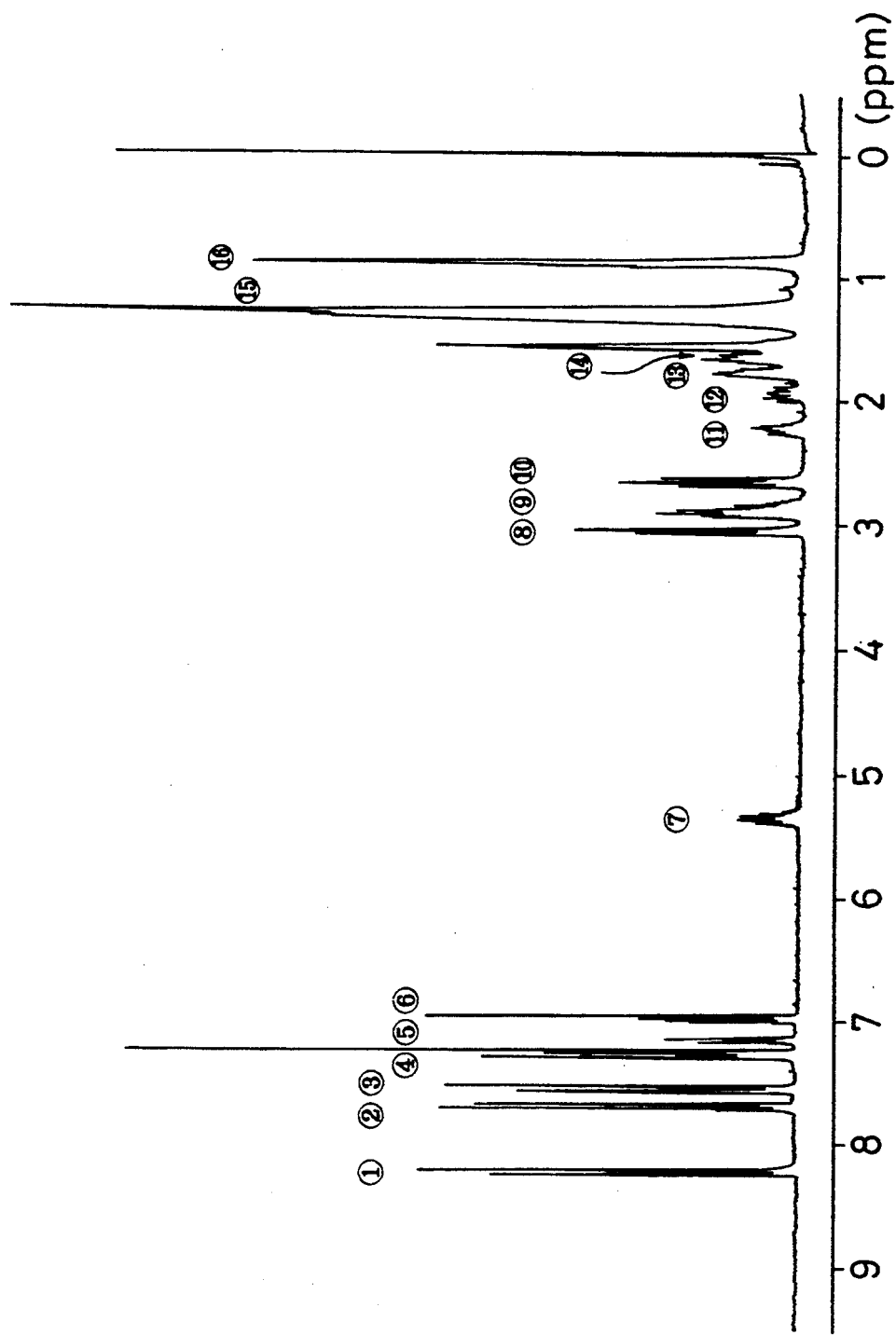

FIG. 4 shows the $^1$H-NMR spectrum of the compound.

From the results of the analysis, the compound was identified to be an ester compound of 6-[4'-(4"-octyl)biphenylcarbonyloxy]-(−)-1,2,3,4-tetrahydronaphthalene-2-carboxylic acid and (R)-1-trifluoromethylheptanol (exemplified compound [104−]). The structure of this compound is shown below.

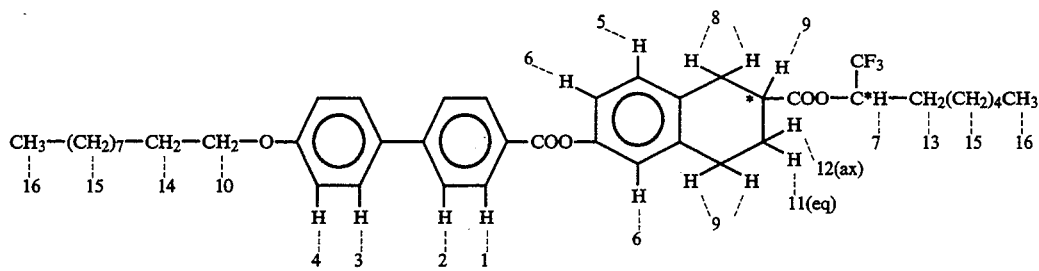

The phase transition temperatures of the above compound are set forth in Table 17.

Comparative Example 2

Synthesis of an ester compound of 6-[4'-(4"-octyl)biphenylcarbonyloxy]-1,2,3,4-tetrahydronaphthalene-2carboxylic acid (starting material: 1,2,3,4-tetrahydronaphthalene-2-carboxylic acid) and (R)-1-trifluoromethylheptanol The procedures of Example 3 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4"-octyl)biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethylheptanol (comparative compound [104r]) . The structure of this compound is shown below.

EXAMPLE 5

Synthesis of an ester compound of 6-[4'-(4"-decyloxy)-biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-methylheptanol The procedures of Example 1 were repeated except for using (R)-1-methylheptanol in place of the (R)-1-trifluoromethylheptanol used in the seventh step, to obtain a colorless semisolid.

The M/e value of FD-mass spectrum on the semisolid was 640.

The $^1$H-NMR spectrum of this compound was measured.

Figure 5:
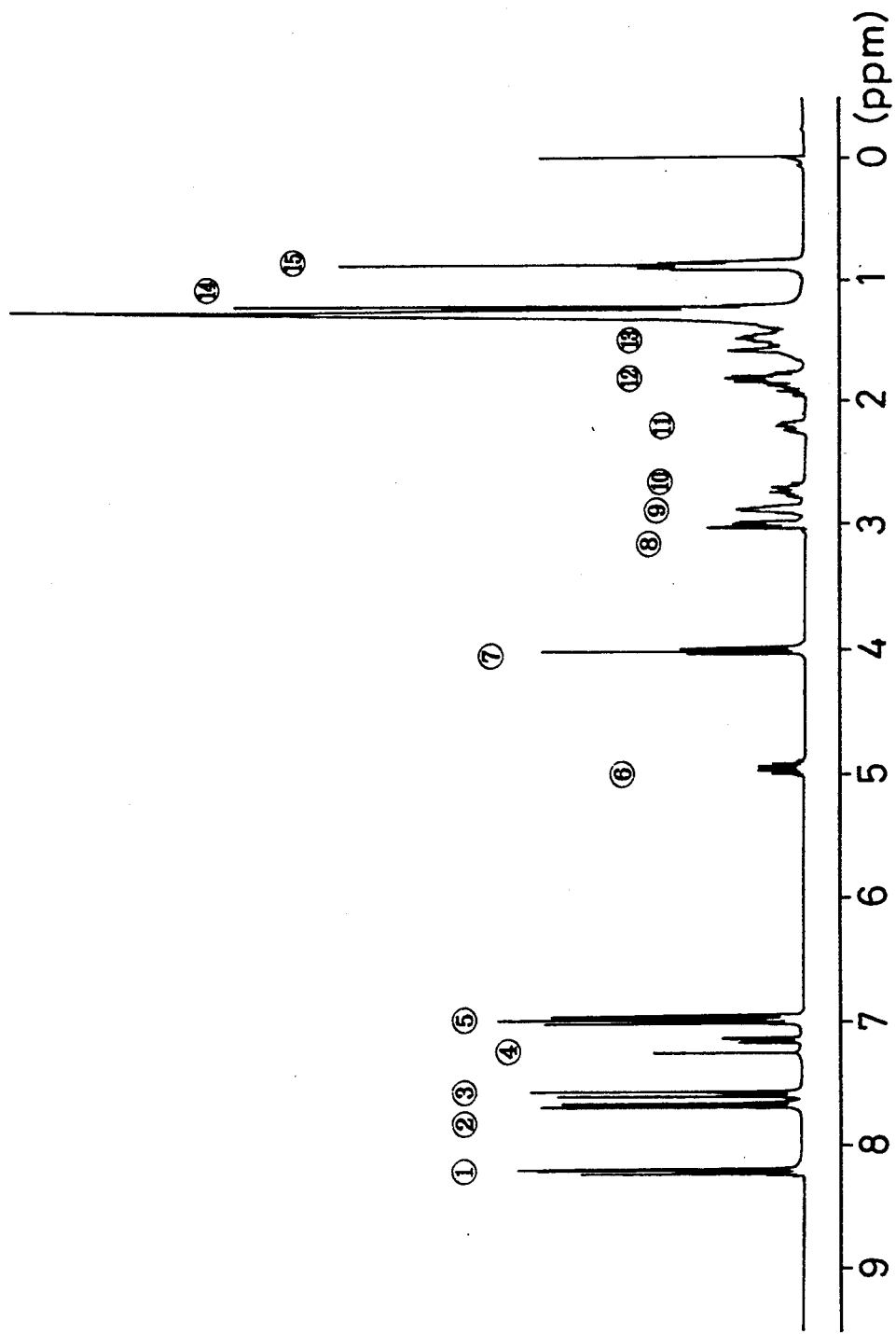

FIG. 5 shows the $^1$H-NMR spectrum of the compound.

From the results of the analysis, the compound was identified to be an ester compound of 6-[4'-(4"-decyloxy)biphenylcarbonyloxy]-(+)-1,2,3,4-tetrahydronaphthalene-2-carboxylic acid and (R)-1-methylheptanol (exemplified compound [202+]) . The structure of this compound is shown below.

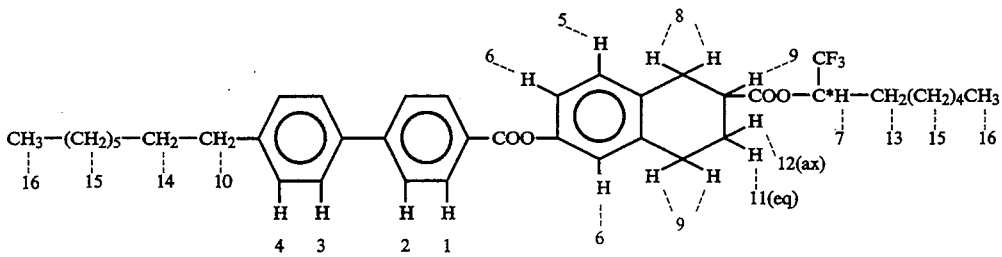

The phase transition temperatures of the above compound are set forth in Table 17.

TABLE 17

| | | Phase Series | | | | |
|---|---|---|---|---|---|---|
| Compound No. | Crystal Phase | SmCA* | SmC* | SmX | SmA | Isotropic Liquid Phase |
| Ex. 3 104+ | ● | 44 ● 60 | — | — | ● 105 | ● |
| Ex. 4 104− | ● | 41 ● 55 | — | — | ● 105 | ● |
| Comp. Ex. 2 104r | ● | 30 ● 56 | — | — | ● 107 | ● |

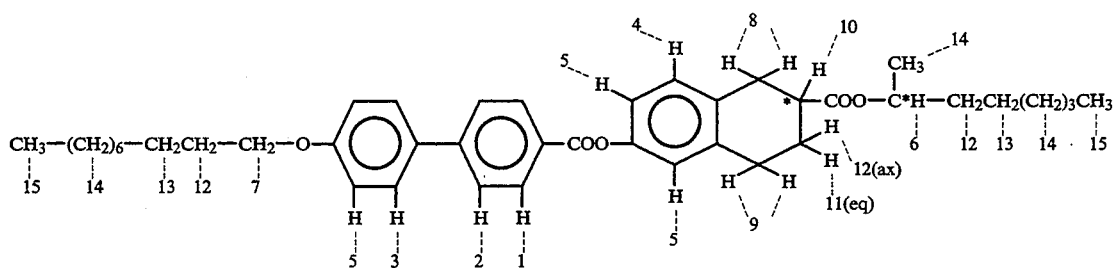

The phase transition temperatures of the above compound are set forth in Table 18.

EXAMPLE 6

Synthesis of an ester compound of 6-[4'-(4''-decyloxy)-biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-methylheptanol The procedures of Example 5 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The M/e value of FD-mass spectrum on the semisolid was 640.

The $^1$H-NMR spectrum of this compound was measured.

Figure 6:
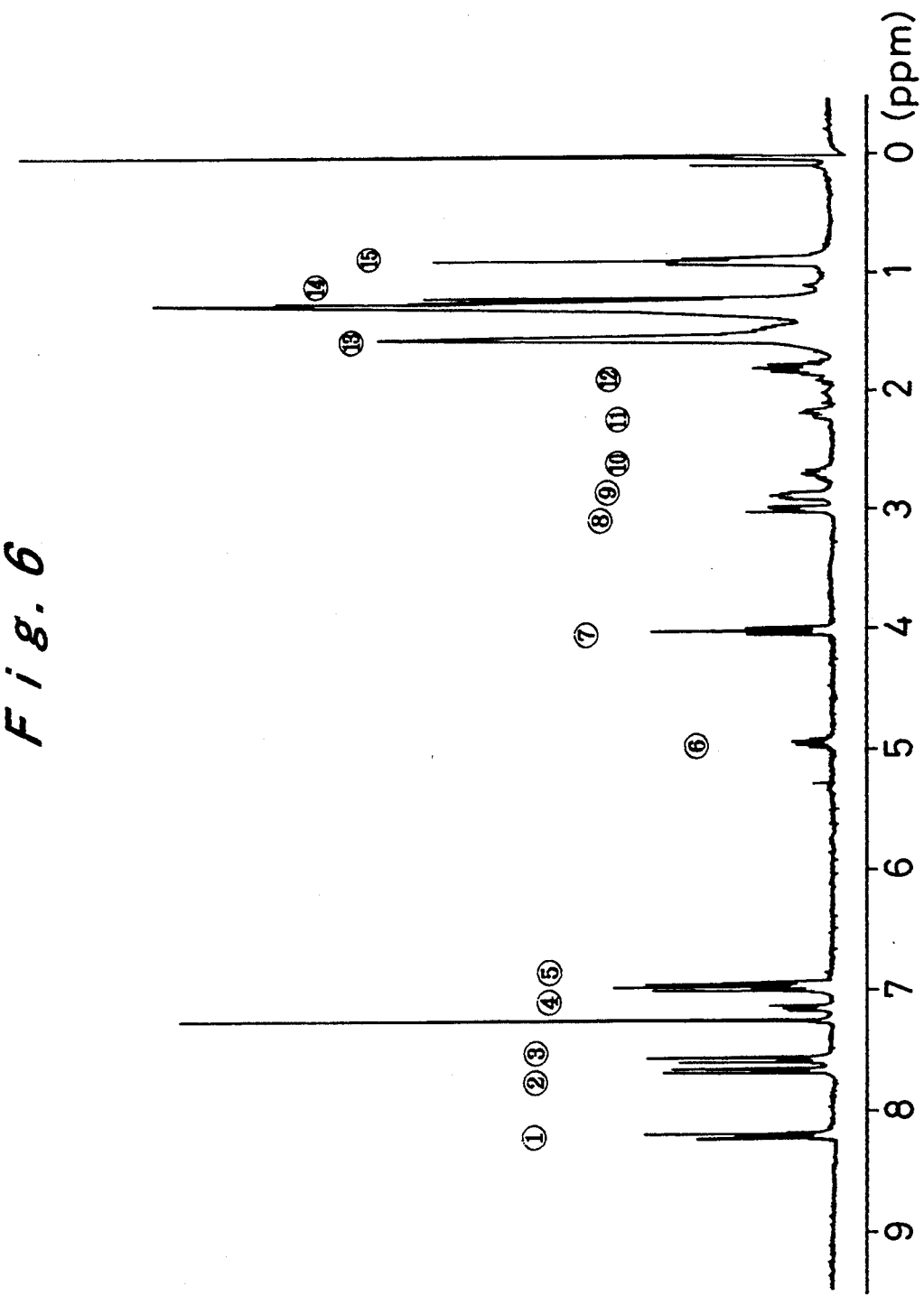

FIG. 6 shows the $^1$H-NMR spectrum of the compound.

From the results of the analysis, the compound was identified to be an ester compound of 6-[4'-(4''-decyloxy) biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-methylheptanol (exemplified compound [202−]), which was the aimed compound. The structure of this compound is shown below.

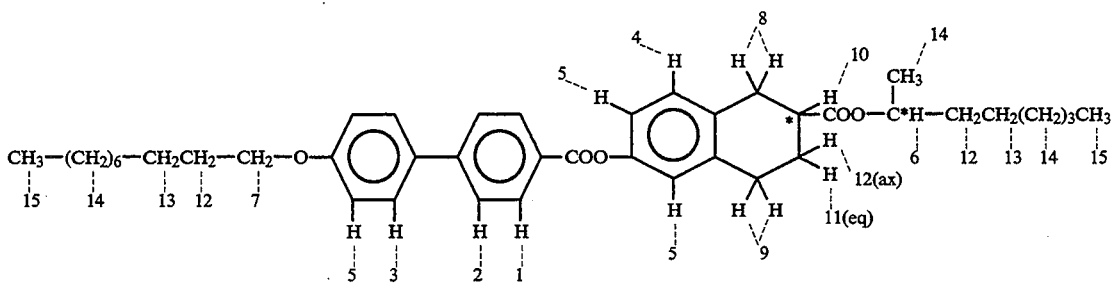

The phase transition temperatures of the above compound are set forth in Table 18.

Comparative Example 3

Synthesis of an ester compound of 6-[4'-(4''-decyloxy)-biphenylcarbonyloxy]-1,2,3,4-tetrahydronaphthalene-2-carboxylic acid (starting material: 1,2,3,4-tetrahydronaphthalene-2-carboxylic acid) and (R)-1-methylheptanol The procedures of Example 5 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4''-decyloxy)biphenylcarbonyloxy]-1,2,3,4-tetrahydronaphthalene-2-carboxylic acid (starting material: 1,2,3,4-tetrahydronaphthalene-2-carboxylic acid) and (R)-1-methylheptanol (comparative compound [202r]). The structure of this compound is shown below.

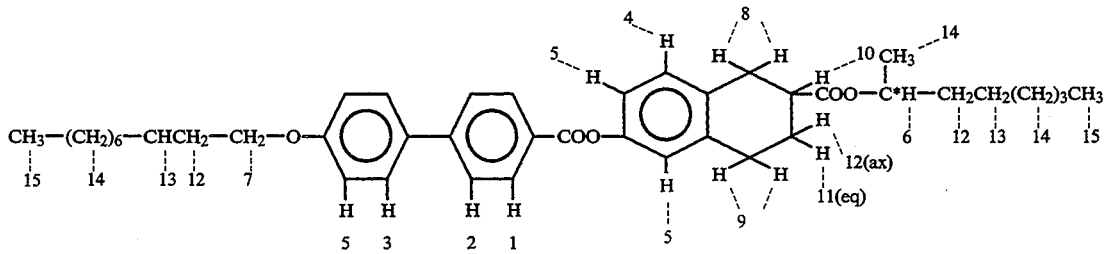

The phase transition temperatures of the above compound are set forth in Table 18.

TABLE 18

| | | Phase Series | | | | | |
|---|---|---|---|---|---|---|---|
| Compound No. | Crystal Phase | SmCA* | SmC* | SmX | SmA | Isotropic Liquid Phase |
| Ex. 5  202+ | • | • 44 • 69 | • 108 | — | • 131 | • |

TABLE 18-continued

| Compound No. | Crystal Phase | SmCA* | SmC* | SmX | SmA | Isotropic Liquid Phase |
|---|---|---|---|---|---|---|
| Ex. 6  202− | ● | 48 ● 92 | — | — | ● 128 | ● |
| Comp. Ex. 3  202r | ● | 35 ● 85 | ● 106 | ● 109 | ● 131 | ● |

EXAMPLE 7

Synthesis of an ester compound of 6-[4'-(4''-tetradecyl)-biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-trifluoromethylheptanol The procedures of Example 1 were repeated except for using tetradecylbiphenyl-4-carboxylic acid in place of the decyloxybiphenyl-4-carboxylic acid used in the tenth step, to obtain a colorless semisolid.

The M/e value of FD-mass spectrum on the semisolid was 734.

The ¹H-NMR spectrum of this compound was measured.

Figure 7:
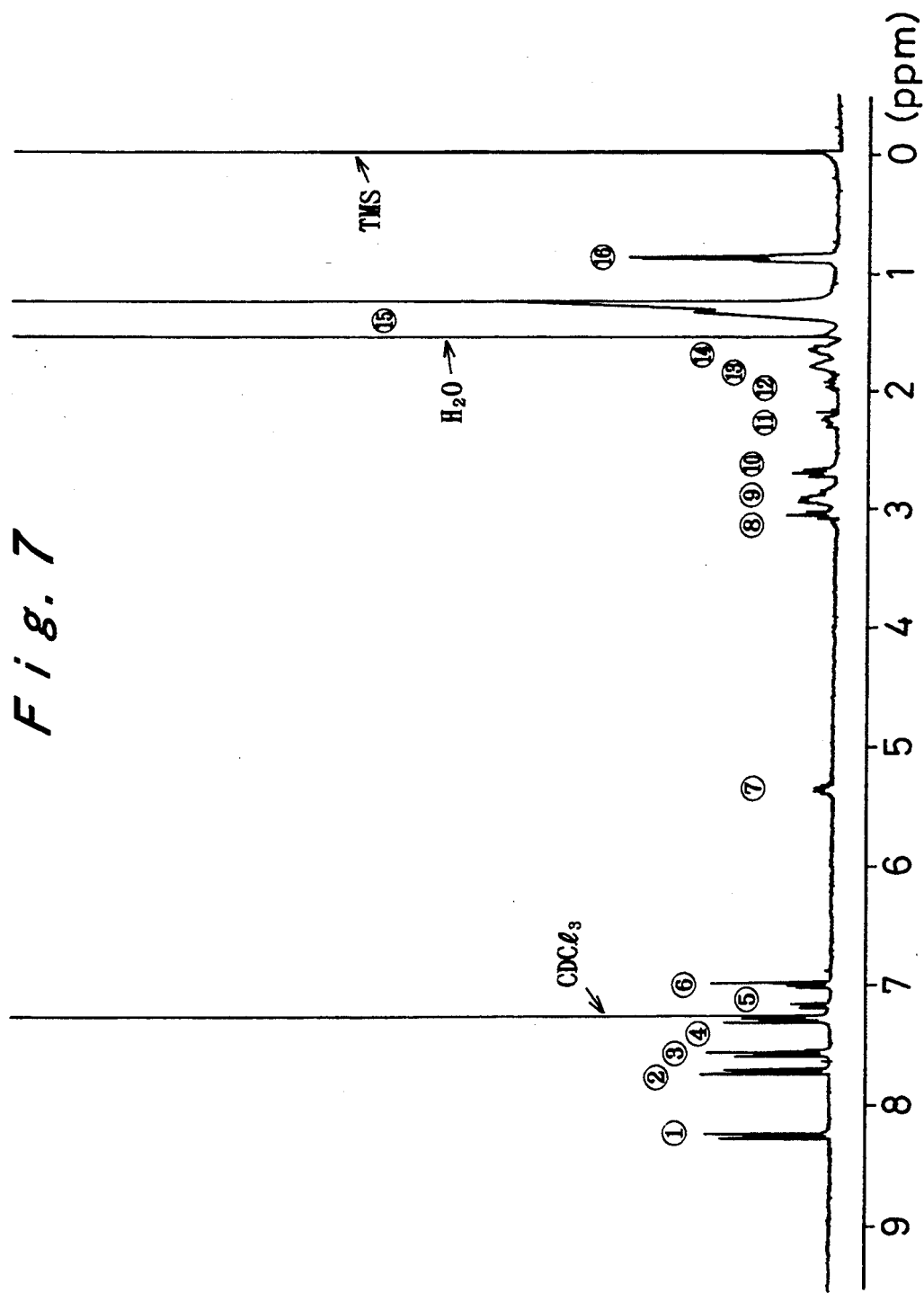

FIG. 7 shows the ¹H-NMR spectrum of the compound.

From the results of the analysis, the compound was identified to be an ester compound of 6-[4'-(4''-tetradecyl)biphenylcarbonyloxy]-(+)-1,2,3,4-tetrahydronaphthalene-2-carboxylic acid and (R)-1-trifluoromethylheptanol (exemplified compound [109+]). The structure of this compound is shown below.

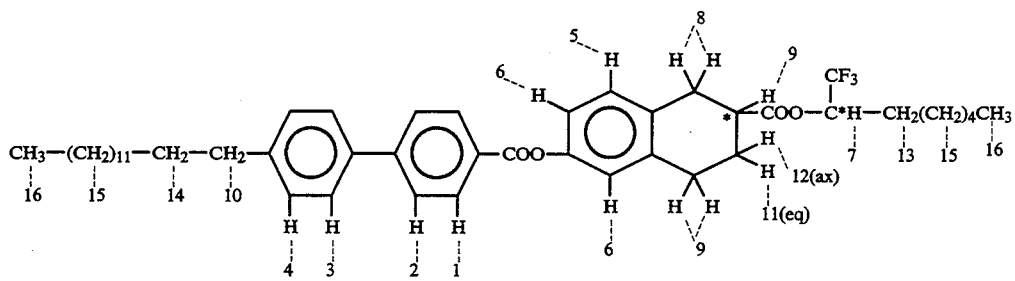

The phase transition temperatures of the above compound are set forth in Table 19.

Comparative Example 4

Synthesis of an ester compound of 6-[4'-(4''-tetradecyl)-biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethylheptanol The procedures of Example 7 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4''-tetradecyl)biphenylcarbonyloxy]-1,2,3,4-tetrahydronaphthalene-2-carboxylic acid (starting material: 1,2,3,4-tetrahydronaphthalene-2-carboxylic acid) and

EXAMPLE 8

Synthesis of an ester compound of 6-[4'-(4''-tetradecyl)-biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-trifluoromethylheptanol The procedures of Example 7 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The M/e value of FD-mass spectrum on the semisolid was 734.

The ¹H-NMR spectrum of this compound was measured.

Figure 8:
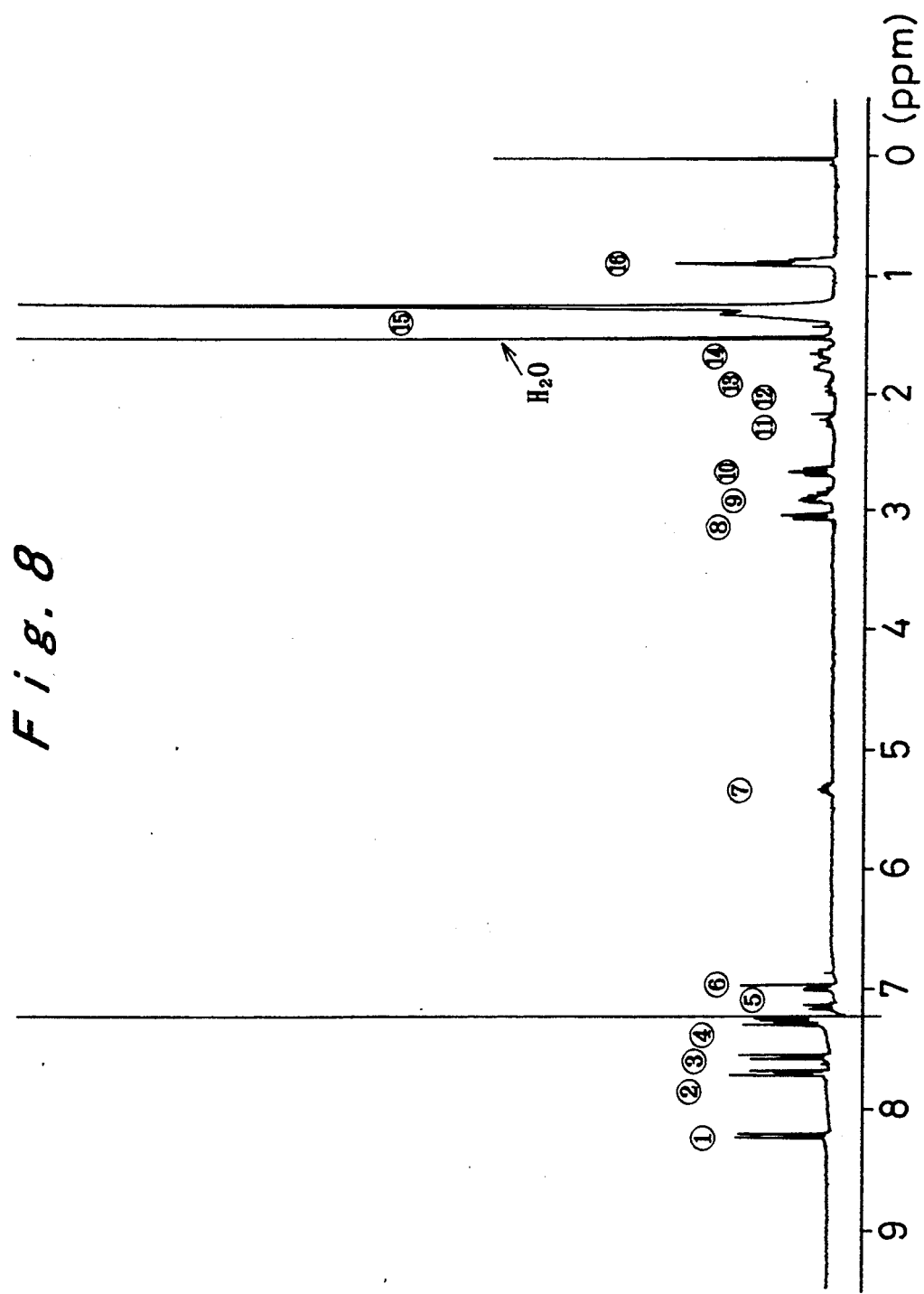

FIG. 8 shows the ¹H-NMR spectrum of the compound.

From the results of the analysis, the compound was identified to be an ester compound of 6-[4'-(4''-tetradecyl)biphenylcarbonyloxy]-(−)-1,2,3,4-tetrahydronaphthalene-2-carboxylic acid and (R)-1-trifluoromethylheptanol (exemplified compound [109−]). The structure of this compound is shown below.

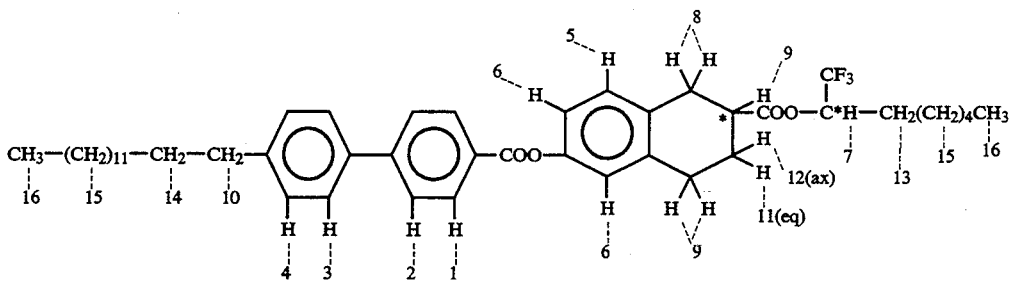

(R)-1-trifluoromethylheptanol (comparative compound [109r]). The structure of this compound is shown below.

fluoromethylpentanol (exemplified compound [164+]). The structure of this compound is shown below.

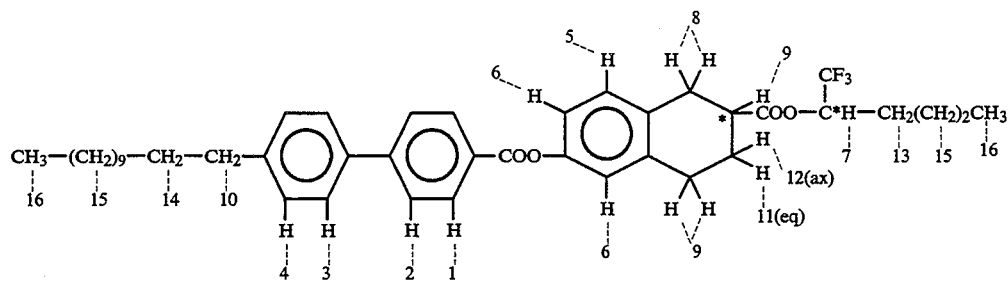

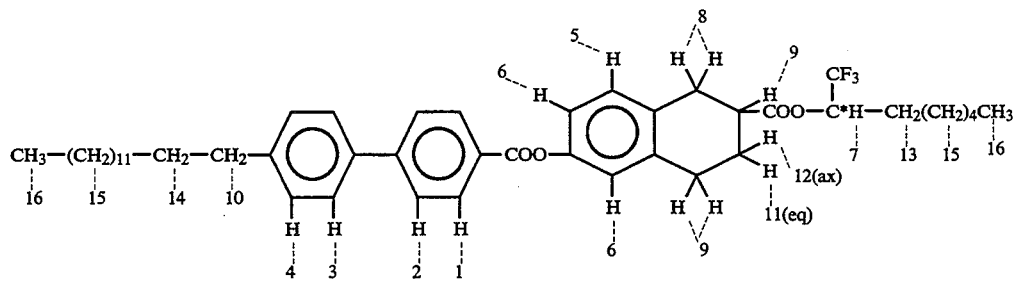

The phase transition temperatures of the above compound are set forth in Table 19.

The phase transition temperatures of the above compound are set forth in Table 20.

TABLE 19

| | | Phase Series | | | | | |
|---|---|---|---|---|---|---|---|
| Compound No. | Crystal Phase | | SmCA* | SmC* | SmX | SmA | Isotropic Liquid Phase |
| Ex. 7  109+ | • | | 45 • 66 | • 69 | — | • 86 | • |
| Ex. 8  109− | • | . | 44 • 59 | • 69 | — | • 87 | • |
| Comp. Ex. 4  109r | • | | 28 • 59 | — | • γ71 | • 89 | • |

Remark:
It is considered that the phase indicated by a sympol left of γ is SmC*γ.

EXAMPLE 9

Synthesis of an ester compound of 6-[4'-(4''-dodecyl)biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-trifluoromethylpentanol The procedures of Example 1 were repeated except for using dodecylbiphenyl-4-carboxylic acid in place of the decyloxybiphenyl-4-carboxylic acid used in the tenth step and using (R)-1-trifluoromethylpentanol in place of the (R)-1-trifluoromethylheptanol used in the seventh step, to obtain a colorless semisolid.

The M/e value of FD-mass spectrum on the semisolid was 678.

The $^1$H-NMR spectrum of this compound was measured.

Figure 9:
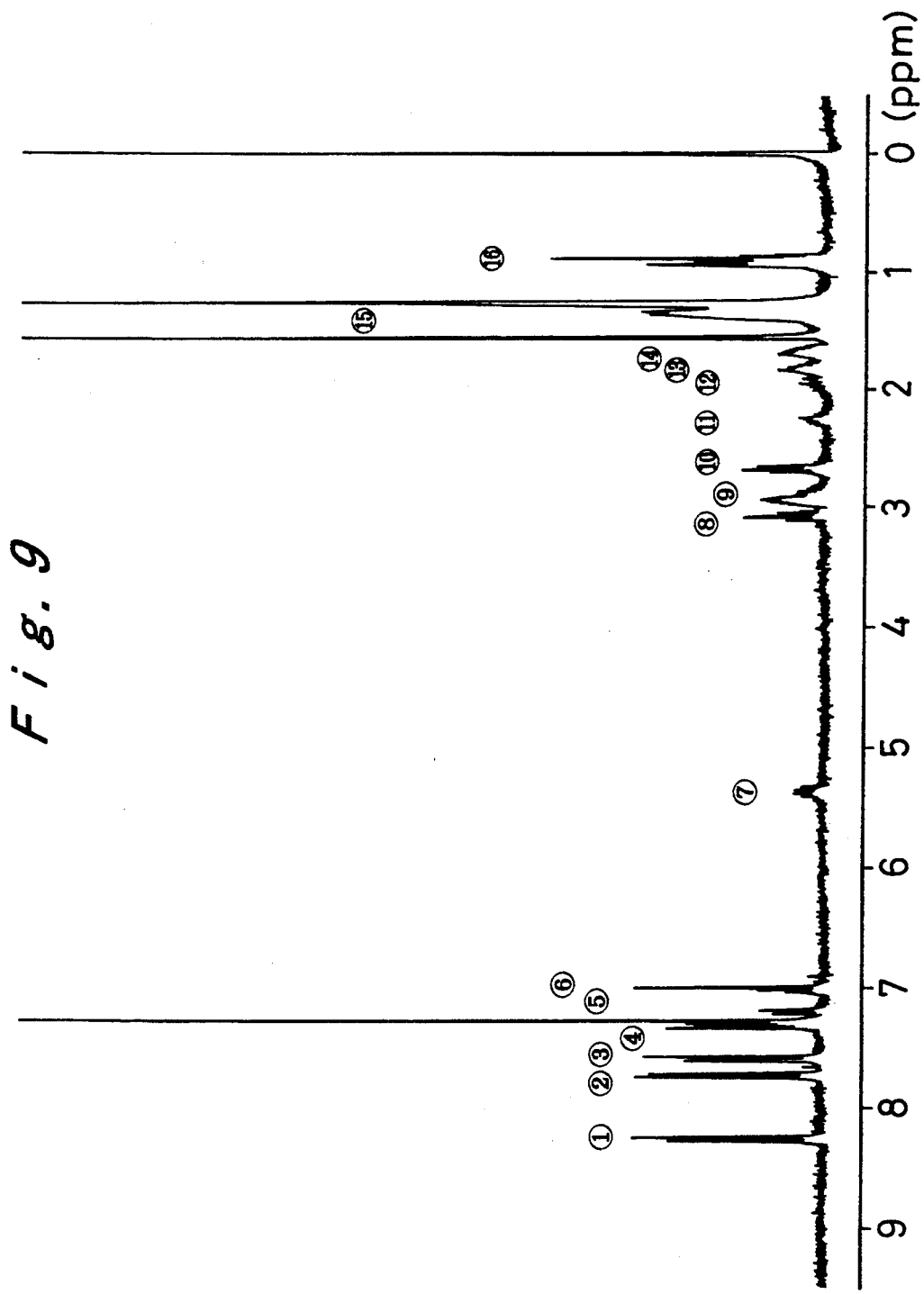

FIG. 9 shows the $^1$H-NMR spectrum of the compound.

From the results of the analysis, the compound was identified to be an ester compound of 6-[4'-(4''-dodecyl)biphenylcarbonyloxy]-(+)-1,2,3,4-tetrahydronaphthalene-2-carboxylic acid and (R)-1-tri-

EXAMPLE 10

Synthesis of an ester compound of 6-[4'-(4''-dodecyl)biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-trifluoromethylpentanol The procedures of Example 9 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The M/e value of FD-mass spectrum on the semisolid was 678.

The $^1$H-NMR spectrum of this compound was measured.

Figure 10:
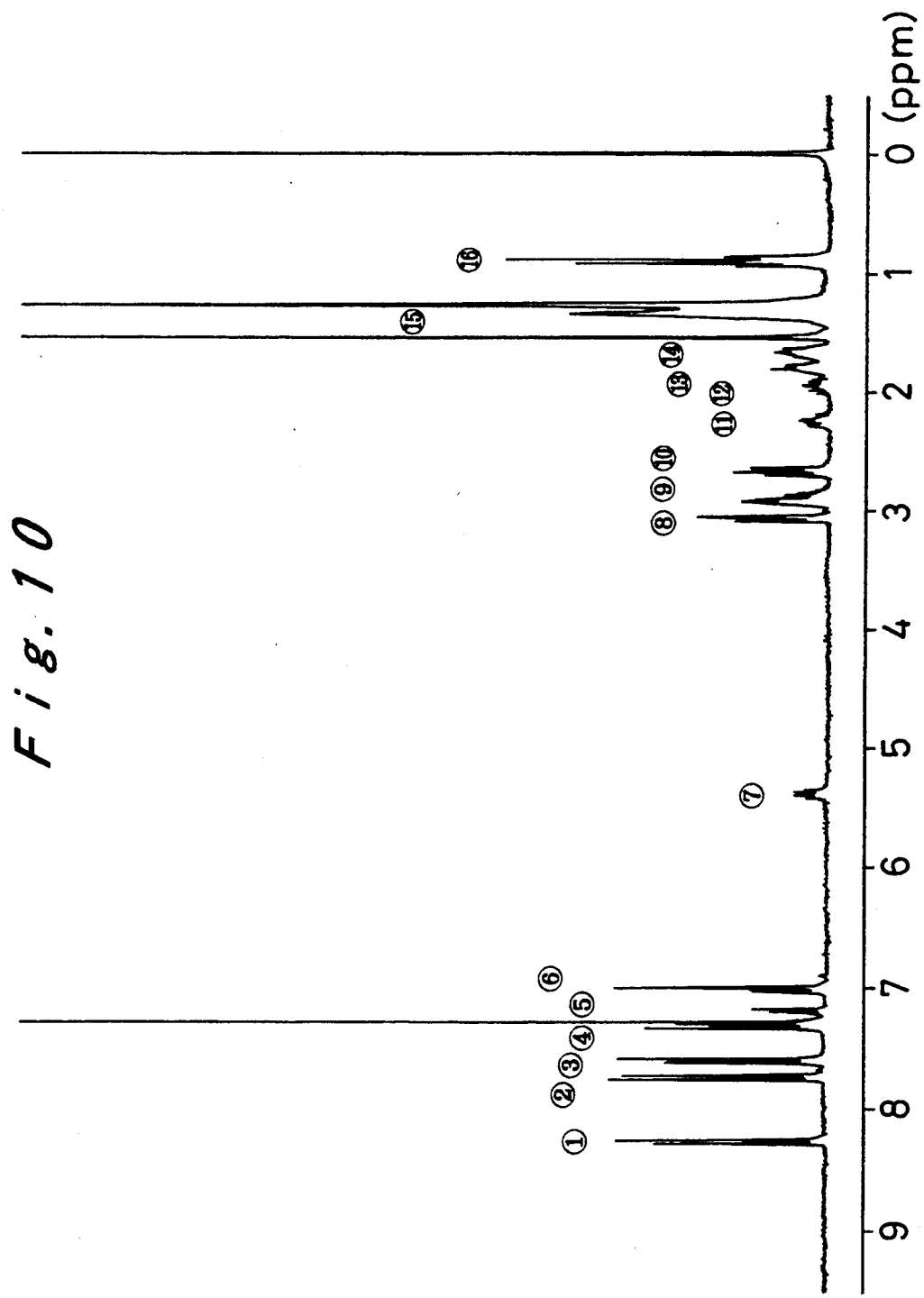

FIG. 10 shows the $^1$H-NMR spectrum of the compound.

From the results of the analysis, the compound was identified to be an ester compound of 6-[4'-(4''-dodecyl)biphenylcarbonyloxy]-(−)-1,2,3,4-tetrahydronaphthalene-2-carboxylic acid and (R)-1-trifluoromethylpentanol (exemplified compound [164−]). The structure of this compound is shown below.

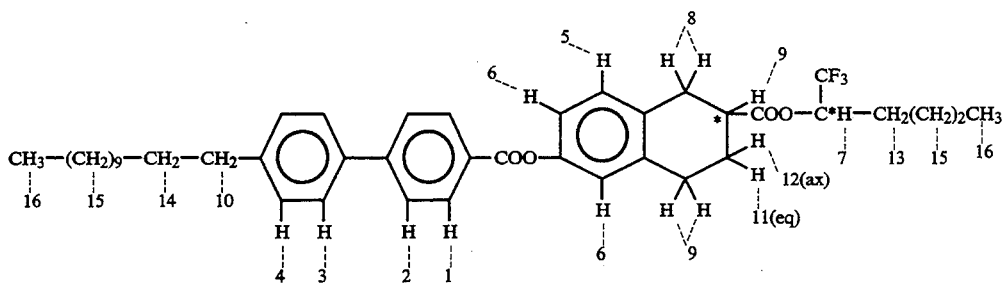

The phase transition temperatures of the above compound are set forth in Table 20.

Comparative Example 5

Synthesis of an ester compound of 6-[4'-(4''-dodecyl)biphenylcarbonyloxy]-1,2,3,4-tetrahydronaphthalene-carboxylic acid (starting material: 1,2,3,4-tetrahydronaphthalene-2-carboxylic acid) and (R)-1-trifluoromethylpentanol The procedures of Example 9 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4''-dodecyl )biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethylpentanol (comparative compound [164r]). The structure of this compound is shown below.

EXAMPLE 11

Synthesis of an ester compound of 6-[4'-(4''-decyloxy)-biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-trifluoromethyl-5-methoxypentanol .

The procedures of Example 1 were repeated except for using (R)-1-trifluoromethyl-5-methoxypentanol in place of the (R)-1-trifluoromethylheptanol used in the seventh step, to obtain a colorless semisolid.

The M/e value of FD-mass spectrum on the semisolid was 696.

The ¹H-NMR spectrum of this compound was measured.

Figure 11:
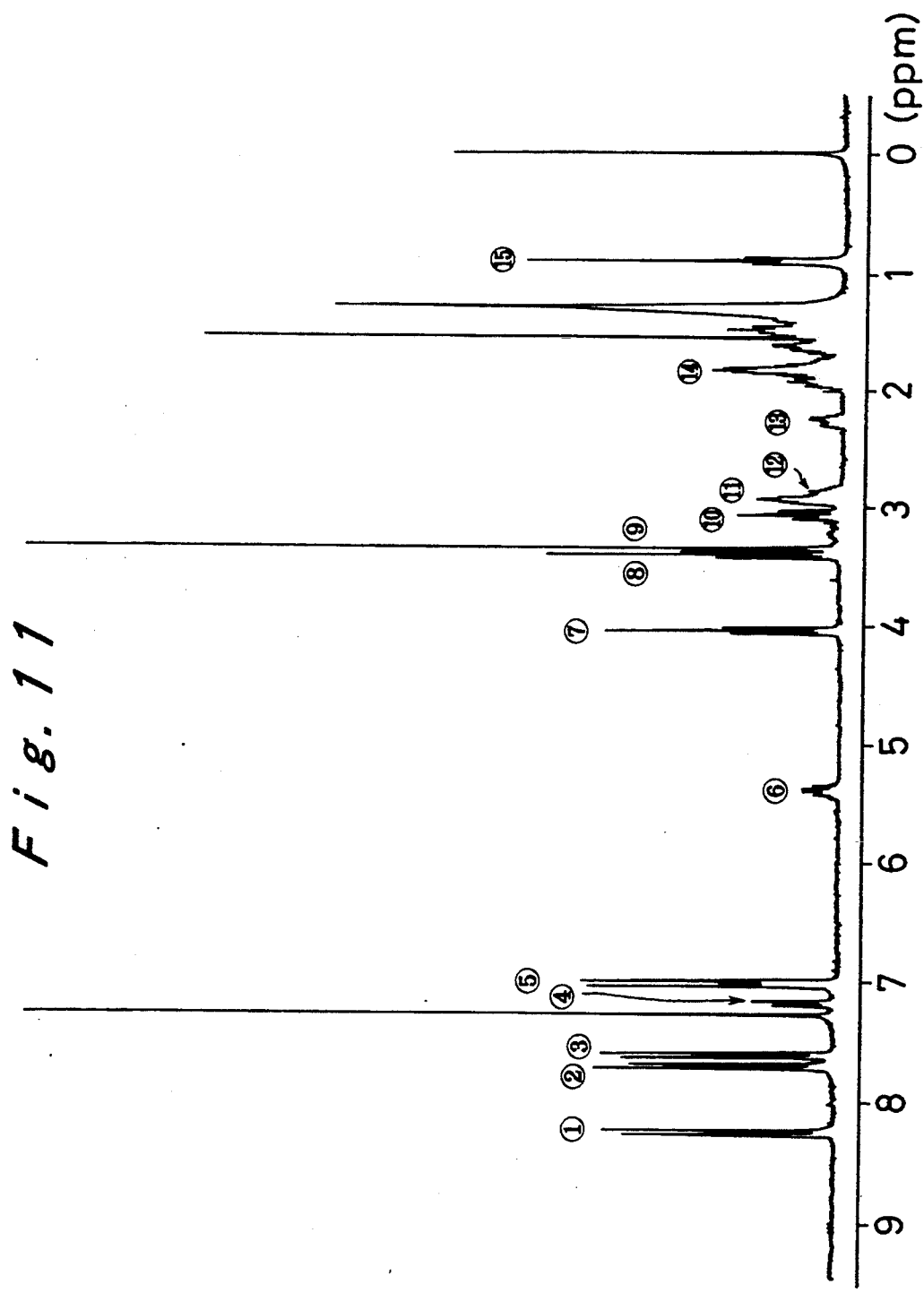

FIG. 11 shows the ¹H-NMR spectrum of the compound.

From the results of the analysis, the compound was identified to be an ester compound of 6-[4'-(4''-decyloxy)biphenylcarbonyloxy]-(+)-1,2,3,4-tetrahydronaphthalene-2-carboxylic acid and (R)-1-trifluoromethyl-5-methoxypentanol (exemplified compound [186+]). The structure of this compound is shown below.

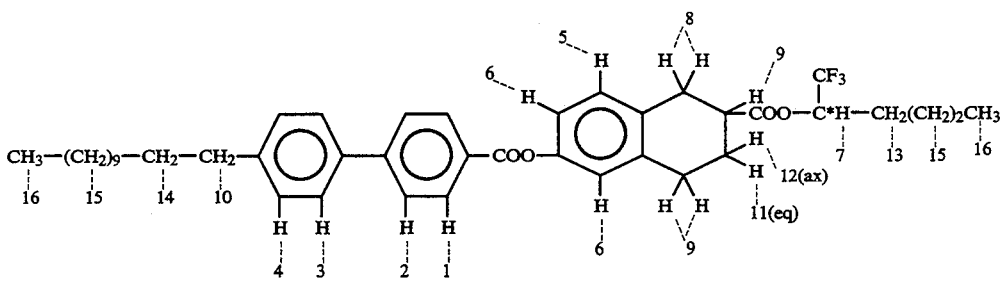

The phase transition temperatures of the above compound are set forth in Table 20.

TABLE 20

| | | Phase Series | | | | | |
|---|---|---|---|---|---|---|---|
| Compound No. | Crystal Phase | SmCA* | SmC* | SmX | SmA | Isotropic Liquid Phase |
| Ex. 9  164+ | • | 30 • 71 | • 86 | — | • 107 | • |
| Ex. 10 164− | • | 54 — | • 86 | — | • 106 | • |
| Comp. Ex. 5  164r | • | 47 • | • 84 | — | • 106 | • |

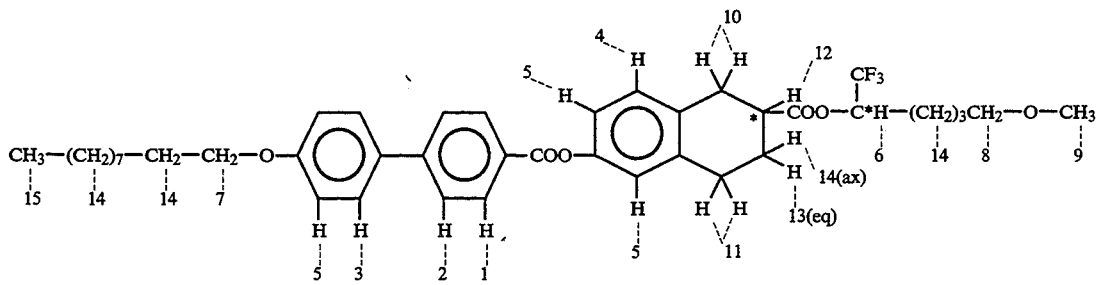

The phase transition temperatures of the above compound are set forth in Table 21.

EXAMPLE 12

Synthesis of an ester compound of 6-[4'-(4''-decyloxy)-biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-trifluoromethyl-5-methoxypentanol.

The procedures of Example 11 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The M/e value of FD-mass spectrum on the semisolid was 696.

Figure 12:
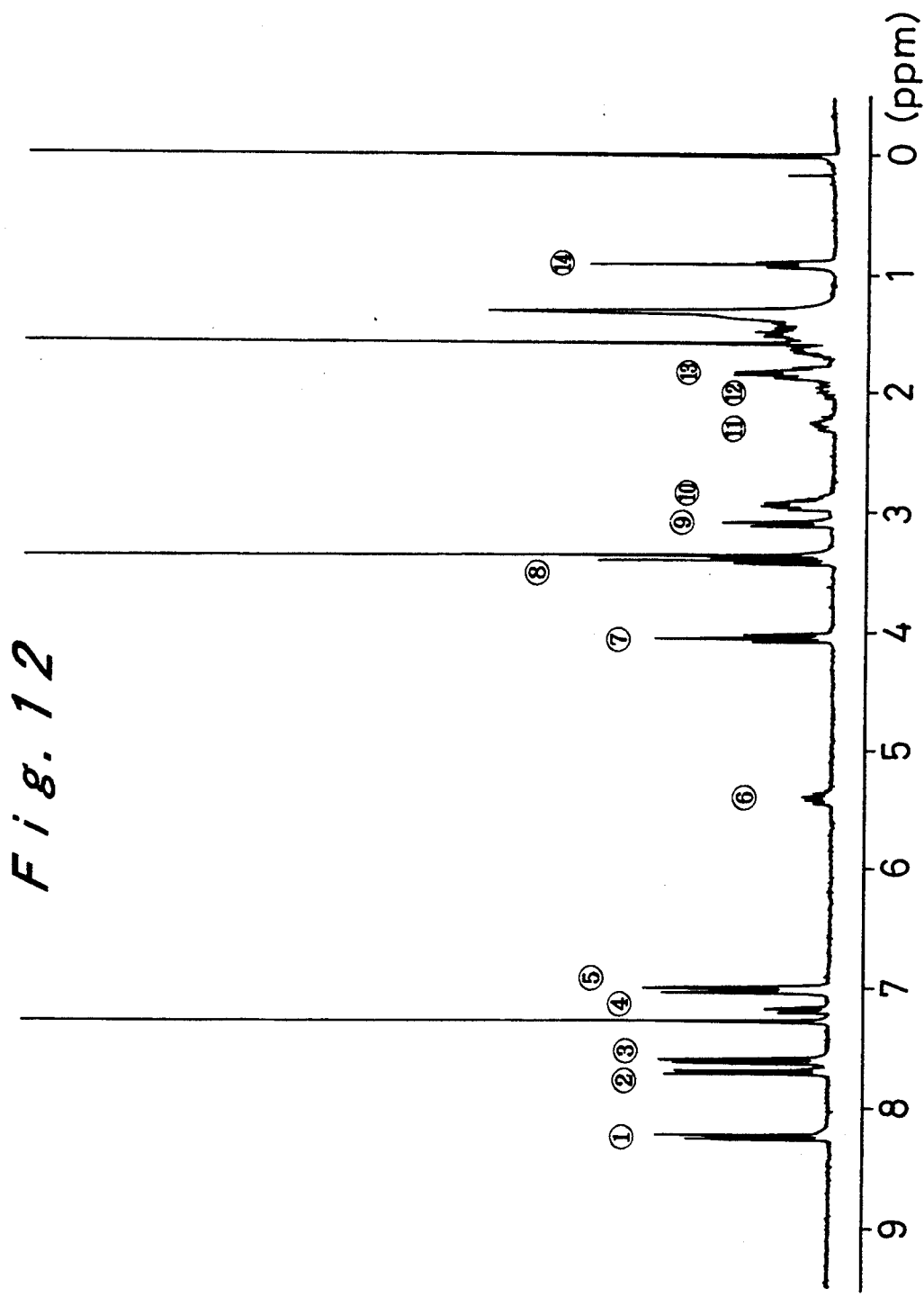

The $^1$H-NMR spectrum of this compound was measured. FIG. 12 shows the $^1$H-NMR spectrum of the compound.

From the results of the analysis, the compound was identified to be an ester compound of 6-[4'-(4''-decyloxy)biphenylcarbonyloxy]-(−)-1,2,3,4-tetrahydronaphthalene-2-carboxylic acid and (R)-1-trifluoromethyl-5-methoxypentanol (exemplified compound [186−]). The structure of this compound is shown below.

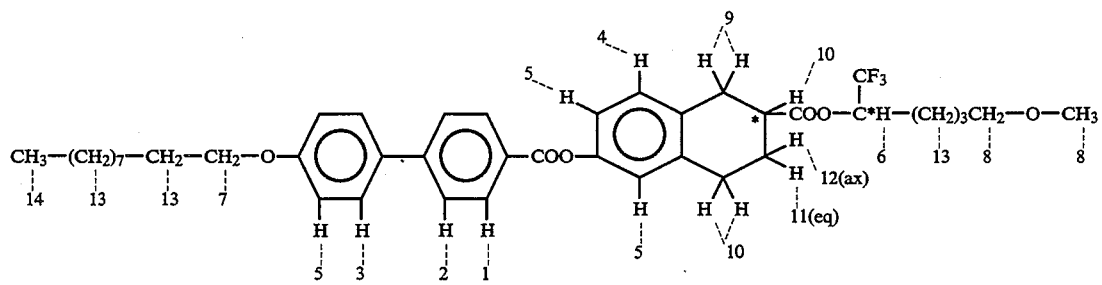

The phase transition temperatures of the above compound are set forth in Table 21.

Comparative Example 6

Synthesis of an ester compound of 6-[4'-(4''-decyloxy)-biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethyl-5-methoxypentanol.

The procedures of Example 11 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4''-decyloxy)biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethyl-5-methoxypentanol (comparative compound [186r]). The structure of this compound is shown below.

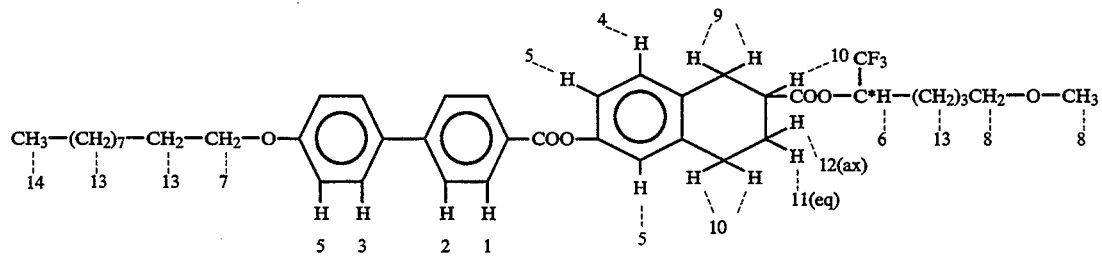

The phase transition temperatures of the above compound are set forth in Table 21.

TABLE 21

| | | Phase Series | | | | |
|---|---|---|---|---|---|---|
| Compound No. | Crystal Phase | SmCA* | SmC* | SmX | SmA | Isotropic Liquid Phase |
| Ex. 11  186+ | • | 65 (• 61 | • 65) | — | • 108 | • |

TABLE 21-continued

| Compound No. | Crystal Phase | Phase Series SmCA* | SmC* | SmX | SmA | Isotropic Liquid Phase |
|---|---|---|---|---|---|---|
| | | | | | | |
| Ex. 12  186− | • | 54 (• 33) | • 94 | — | • 123 | • |
| Comp. Ex. 6  186r | • | 62 (• ) | • 91 | — | • 121 | • |

EXAMPLE 13

Synthesis of an ester compound of 6-[4'-(4''-decyloxy)-biphenylcarbonyloxy]-(+)-1,2,3,4-tetrahydronaphthalene-2-carboxylic acid (starting material: (+)-1,2,3,4-tetrahydronaphthalene-2-carboxylic acid) and (R)-1-trifluoromethyl-2-ethoxycarbonylethanol The procedures of Example 1 were repeated except for using (R)-1-trifluoromethyl-2-ethoxycarbonylethanol in place of the (R)-1-trifluoromethylheptanol used in the seventh step, to obtain a colorless semisolid.

The $^1$H-NMR spectrum of this compound was measured.

Figure 13:
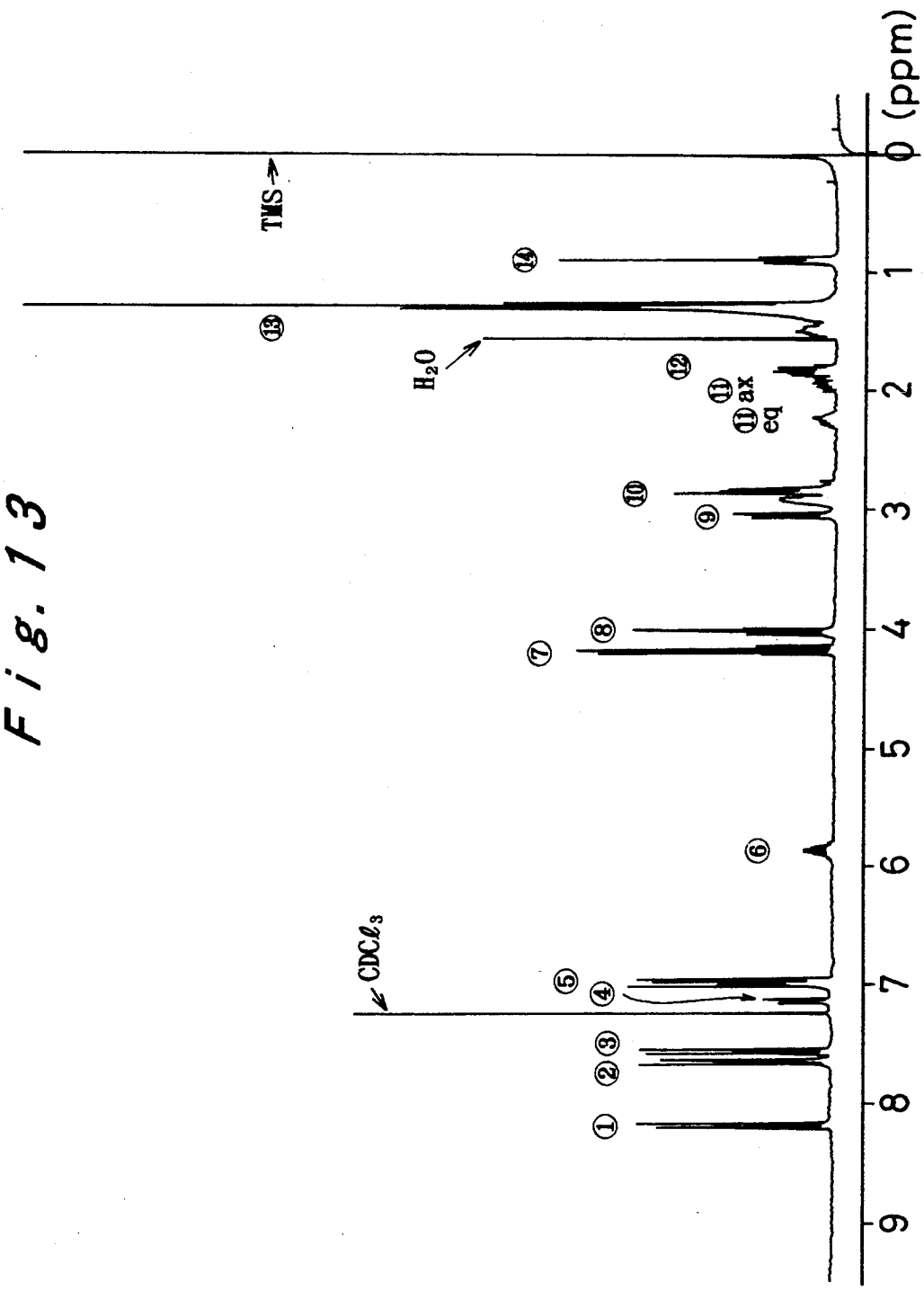

FIG. 13 shows the $^1$H-NMR spectrum of the compound.

From the results of the analysis, the compound was identified to be an ester compound of 6-[4'-(4''-decyloxy)biphenylcarbonyloxy]-(−)-1,2,3,4-tetrahydronaphthalene-2-carboxylic acid and (R)-1-trifluoromethyl-2-ethoxycarbonylethanol (exemplified compound [170−]). The structure of this compound is shown below.

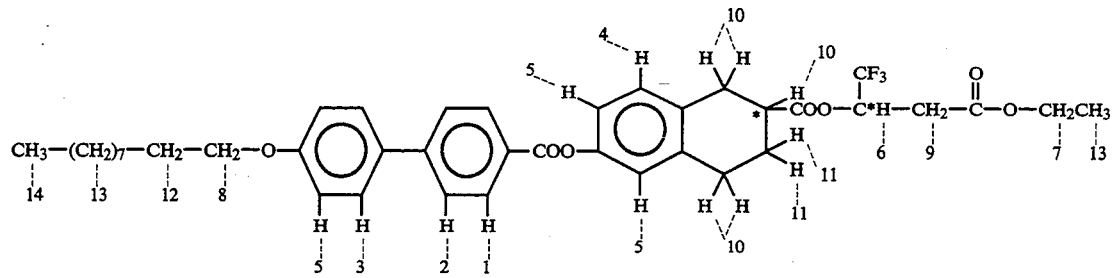

The M/e value of FD-mass spectrum on the semisolid was 696.

From the results of the analysis, the compound was identified to be an ester compound of 6-[4'-(4''-decyloxy)biphenylcarbonyloxy]-(+)-1,2,3,4-tetrahydronaphthalene-2-carboxylic acid and (R)-1-trifluoromethyl-2-ethoxycarbonylethanol (exemplified compound [170+]) .

EXAMPLE 14

Synthesis of an ester compound of 6-[4'-(4''-decyloxy)-biphenylcarbonyloxy]-(−)-1,2,3,4-tetrahydronaphthalene-2-carboxylic acid (starting material: (−)-1,2,3,4-tetrahydronaphthalene-2-carboxylic acid) and (R)-1-trifluoromethyl-2-ethoxycarbonylethanol The procedures of Example 13 were repeated except for using (−)-1,2,3,4-tetrahydronaphthalene-2-carboxylic acid in place of the (+)-1,2,3,4-tetrahydronaphthalene-2-carboxylic acid, to obtain a colorless semisolid.

The phase transition temperatures of the above compound are set forth in Table 22.

Comparative Example 7

Synthesis of an ester compound of 6-[4'-(4''-decyloxy)biphenylcarbonyloxy]-1,2,3,4-tetrahydronaphthalene-2-carboxylic acid (starting material: 1,2,3,4-tetrahydronaphthalene-2-carboxylic acid) and (R)-1-trifluoromethyl-1-ethoxycarbonylethanol The procedures of Example 13 were repeated except for using 1,2,3,4-tetrahydronaphthalene-2-carboxylic acid in place of the (+)-1,2,3,4-tetrahydronaphthalene-2-carboxylic acid, to obtain an ester compound of 6-[4'-(4''-decyloxy)biphenylcarbonyloxy]-1,2,3,4-tetrahydronaphthalene-2-carboxylic acid (starting material: 1,2,3,4-tetrahydronaphthalene-2-carboxylic acid) and (R) -1-trifluoromethyl-2-ethoxycarbonylethanol (comparative compound [170r]). The structure of this compound is shown below.

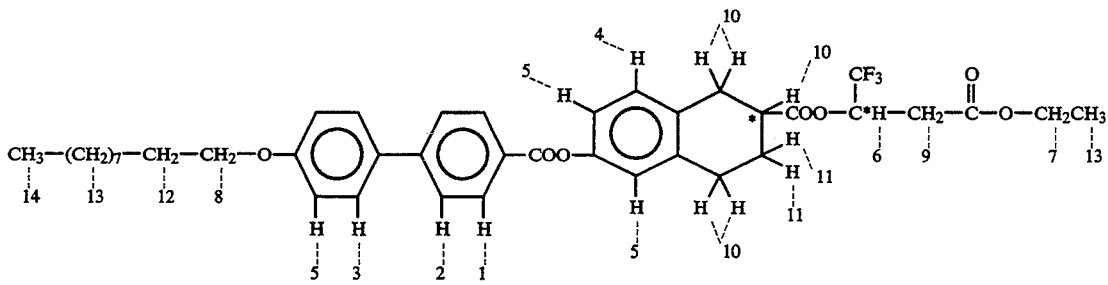

The M/e value of FD-mass spectrum on the semisolid was 696.

The phase transition temperatures of the above compound are set forth in Table 22.

TABLE 22

| Compound No. | Crystal Phase | | SmCA* | | SmC* | | SmX | SmA | | Isotropic Liquid Phase |
|---|---|---|---|---|---|---|---|---|---|---|
| Ex. 14  170— | • | 64 — | • | 99 | — | • | 129 | • |
| Comp. Ex. 7  170r | • | 50 — | • | 104 | — | • | 129 | • |

EXAMPLE 15

The compound obtained in Example 1 was filled in a cell shown in FIG. 16 to manufacture a liquid crystal element in the following manner.

The liquid crystal compound [98+] obtained in Example 1 was made isotropic liquid and poured into a cell in which two orientation control films (thickness: 300 angstrom) were formed on the inner surfaces of two ITO (Indium Tin Oxide) transparent electrodes 55, as shown in FIG. 5, said orientation films being made of polyimide (PIQ-5400, available from Hitachi Kasei Kogyo K.K.) and rubbed in such a manner that they have orientation almost parallel to each other and in the same direction. Then, the liquid crystal compound filled in the cell was slowly cooled at a rate of not higher than 1° C./min.

The cell was nipped by a polarizer and an analyzer, transmission axes of said polarizer and analyzer meeting at right angles, and the angle of the cell against the polarizer was adjusted so that the amount of the transmitted light was minimized when the voltage applied to the cell was 0 V.

When the applied voltage was changed in a moment from 0 V to 30 V at 60° C., the response time of the element from the dark state to the bright state was 390 $\mu$sec, and it was confirmed that the switching between those states was conducted at a high speed correspondingly to the change of the applied voltage.

Comparative Example 8

The procedures of Example 15 were repeated except for replacing the liquid crystal compound [98+] with the comparative compound [98r], to manufacture a liquid crystal element.

When the applied voltage was changed in a moment from 0 V to 30 V at 30° C., the response time of the element from the dark state to the bright state was 3,200 $\mu$sec.

EXAMPLE 16

The procedures of Example 15 were repeated except for replacing the liquid crystal compound [98+] with the liquid crystal compound [104—], to manufacture a liquid crystal element.

When the applied voltage was changed in a moment from 0 V to 30 V at 40° C., the response time of the element from the dark state to the bright state was 46 $\mu$sec, and it was confirmed that the switching between those states was conducted at a high speed correspondingly to the change of the applied voltage.

Comparative Example 9

The procedures of Example 15 were repeated except for replacing the liquid crystal compound [98+] with the comparative compound [104r], to manufacture a liquid crystal element.

When the applied voltage was changed in a moment from 0 V to 30 V at 40° C., the response time of the element from the dark state to the bright state was 53 $\mu$sec.

EXAMPLE 17

The procedures of Example 15 were repeated except for replacing the liquid crystal compound [98+] with the liquid crystal compound [202+], to manufacture a liquid crystal element.

When the applied voltage was changed in a moment from 0 V to 30 V at 50° C., the response time of the element from the dark state to the bright state was 230 $\mu$sec, and it was confirmed that the switching between those states was conducted at a high speed correspondingly to the change of the applied voltage.

Comparative Example 10

The procedures of Example 15 were repeated except for replacing the liquid crystal compound [98+] with the comparative compound [202r], to manufacture a liquid crystal element.

When the applied voltage was changed in a moment from 0 V to 30 V at 50° C., the response time of the element from the dark state to the bright state was 730 $\mu$sec.

EXAMPLE 18

The procedures of Example 15 were repeated except for replacing the liquid crystal compound [98+] with the liquid crystal compound [109—], to manufacture a liquid crystal element.

When the applied voltage was changed in a moment from 0 V to 30 V at 50° C., the response time of the element from the dark state to the bright state was 31 $\mu$sec, and it was confirmed that the switching between those states was conducted at a high speed correspondingly to the change of the applied voltage.

Comparative Example 11

The procedures of Example 15 were repeated except for replacing the liquid crystal compound [98+] with the comparative compound [109r], to manufacture a liquid crystal element.

When the applied voltage was changed in a moment from 0 V to 30 V at 50° C., the response time of the element from the dark state to the bright state was 140 $\mu$sec.

EXAMPLE 19

The exemplified compound (98—) represented by the following formula [98—] and the exemplified compound (104—) represented by the following formula [104—] were mixed in a weight ratio between those compounds of 50:50. Using the resulting mixture, a liquid crystal element of the present invention was manufactured.

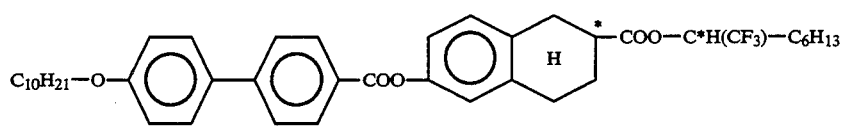

[98-]

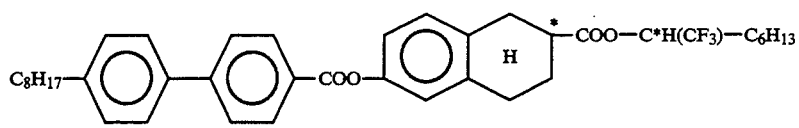

[104-]

The phase transition temperatures of the above compounds and the mixture are set forth in Table 23.

The phase transition temperatures of the above compounds and the mixture are set forth in Table 24.

TABLE 23

| Compound No. | Phase Series | | | | | |
|---|---|---|---|---|---|---|
| | Crystal Phase | SmCA* | SmC* | SmX | SmA | Isotropic Liquid Phase |
| 98— | • | 48 • 92 | • 99 | — | • 129 | • |
| 104— | • | 41 • 55 | • | — | • 105 | • |
| [98—] + [104—] wt ratio = 50:50 | • | <25 • 75 | • | — | • 117 | • |

TABLE 24

| Compound No. | Phase Series | | | | | |
|---|---|---|---|---|---|---|
| | Crystal Phase | SmCA* | SmC* | SmX | SmA | Isotropic Liquid Phase |
| 109— | • | 44 • 59 | • 69 | — | • 87 | • |
| 186— | • | 54 (• 33) | • 94 | — 500 | 123 | • |
| [109—] + [186—] wt ratio = 50:50 | • | <25 • 64 | • 80 | — | • 106 | • |

In the above table, [98—] denotes the exemplified compound (98—), and [104—] denotes the exemplified compound (104—).

In the above table, [109—] denotes the exemplified compound (109—), and [186—] denotes the exemplified compound (186—).

EXAMPLE 20

The exemplified compound (109—) represented by the following formula [109—] and the exemplified compound (186—) represented by the following formula [186—] were mixed in a weight ratio between those compounds of 50:50. Using the resulting mixture, a liquid crystal element of the present invention was manufactured.

EXAMPLE 21

The exemplified compound (104—) represented by the following formula [104—] and the exemplified compound (202—) represented by the following formula [202—] were mixed in a weight ratio between those compounds of 50:50. Using the resulting mixture, a liquid crystal element of the present invention was manufactured.

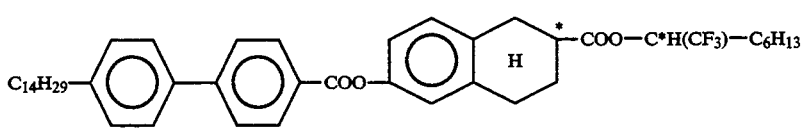

[109-]

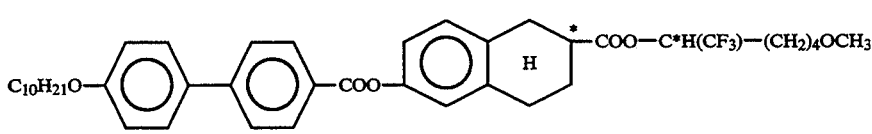

[186-]

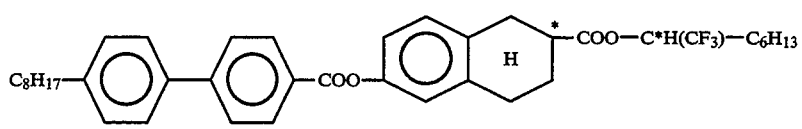

[104-]

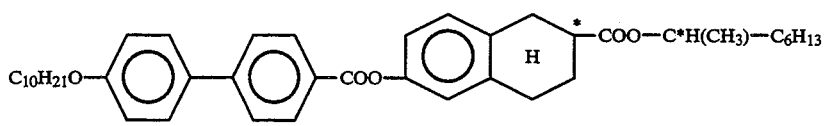

[202-]

The phase transition temperatures of the above compounds and the mixture are set forth in Table 25.

The phase transition temperatures of the above compounds and the mixture are set forth in Table 26.

TABLE 25

| Compound No. | Crystal Phase | Phase Series SmCA* | SmC* | SmX | SmA | Isotropic Liquid Phase |
|---|---|---|---|---|---|---|
| 104— | • | 41 • 55 | — | — | • 105 | • |
| 202— | • | 48 • 92 | — | — | • 128 | • |
| [104—] + [202—] wt ratio = 50:50 | • | <25 • 69 | — | — | • 119 | • |

TABLE 26

| Compound No. | Crystal Phase | Phase Series SmCA* | SmC* | SmX | SmA | Isotropic Liquid Phase |
|---|---|---|---|---|---|---|
| 186— | • | 54 (• 33) | — | 94 | — • 123 | • |
| 164— | • | 54 — | • 86 | — | • 106 | • |
| [186—] + [164—] wt ratio = 50:50 | • | <25 • 64 | • 87 | — | • 113 | • |

In the above table, [104—] denotes the exemplified compound (104—), and [202—] denotes the exemplified compound (202—).

In the above table, [186—] denotes the exemplified compound (186—), and [164—] denotes the exemplified compound (164—).

EXAMPLE 22

The exemplified compound (186—) represented by the following formula [186—] and the exemplified compound (164—) represented by the following formula [164—] were mixed in a weight ratio between those compounds of 50:50. Using the resulting mixture, a liquid crystal element of the present invention was manufactured.

EXAMPLE 23

The exemplified compound (170—) represented by the following formula [170—] and the exemplified compound (109—) represented by the following formula [109—] were mixed in a weight ratio between those compounds of 50:50. Using the resulting mixture, a liquid crystal element of the present invention was manufactured.

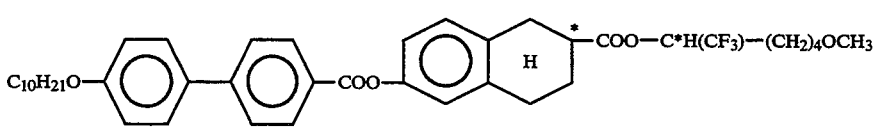

[186-]

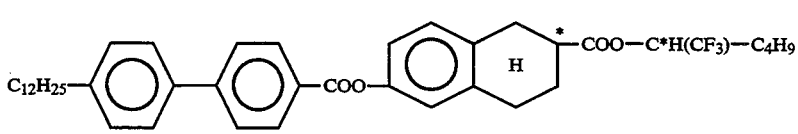

[164-]

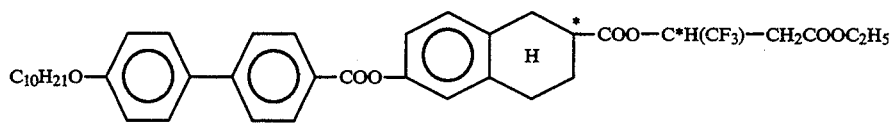 [170-]

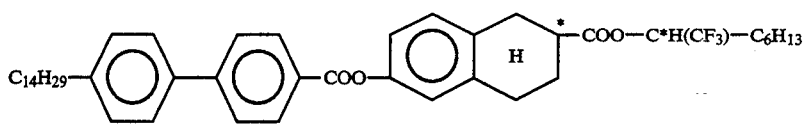 [109-]

The phase transition temperatures of the above compounds and the mixture are set forth in Table 27.

TABLE 27

| Compound No. | Crystal Phase | | SmCA* | | SmC* | | SmX | | SmA | | Isotropic Liquid Phase |
|---|---|---|---|---|---|---|---|---|---|---|---|
| 170— | • | | 64 — | • | 99 | — | • | | 129 | • | |
| 109— | • | | 44 • 59 | • | 69 | — | • | | 87 | • | |
| [170—] + [109—] wt ratio = 50:50 | • | | — | • | 82 | — | • | | 107 | • | |

In the above table, [170—] denotes the exemplified compound (170—), and [109—] denotes the exemplified compound (109—).

What is claimed is:

1. A liquid crystal material represented by the following formula [I]:

$$R-X-A^1-Y^1-A^2-(Y^2-A^3)_n-Z-R^*$$  [I]

wherein R is an alkyl or polyfluoroalkyl group of 3 to 20 carbon atoms in which a part of —CH$_2$— groups or —CF$_2$— groups can be substituted with —O— group, said —CH$_2$— groups or —CF$_2$— groups being not directly bonded to X and not adjacent to each other, X is a group selected from the group consisting of —COO—, —O—CO—, —CO— and —O—, or a single bond, n is 0 or 1, at least one group of A$^1$, A$^2$ and A$^3$ existing in the formula [I] is an optically active group selected from the group consisting of

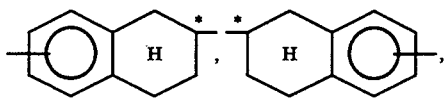

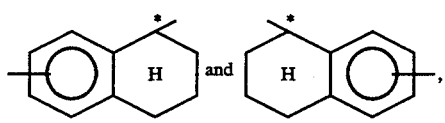

wherein a symbol of * denotes as chiral center of the optical active structure in the tetraline ring, the residual groups of A$^1$, A$^2$ and A$^3$ are each independently a group selected from the group consisting of

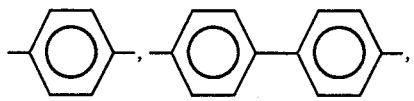

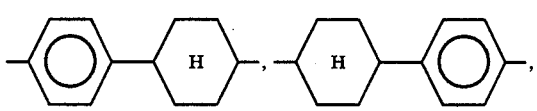

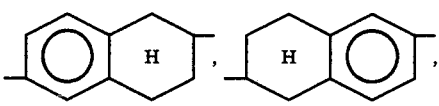

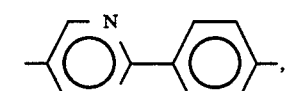

and

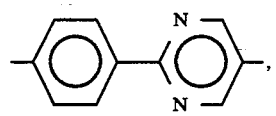

Y$^1$ and Y$^2$ are each independently a group selected from the group consisting of —COO—, —O—CO—, —CH$_2$CH$_2$—, —CH$_2$O—, —O—CH$_2$—, —CO—CH$_2$— and —CH$_2$—CO—, Z is a group selected from the group consisting of —O—, —CO—, —COO— and —O—CO—, or a single bond, and R* is an optically active group of 4 to 20 carbon atoms having at least one asymmetric carbon atom in which a hydrogen atom bonded to a carbon atom of said optically active group can being substituted with a halogen atom.

2. The liquid crystal material as claimed in claim 1, wherein Y$^1$ and Y$^2$ are each independently —O—CO— or —COO—.

3. The liquid crystal material as claimed in claim 1, wherein Z is —O— or —COO—.

4. The liquid crystal material as claimed in claim 1, wherein R* is a group selected from the group consisting of —C*H(CF₃)—C₆H₁₃, —C*H(CF₃)—C₅H₁₁, —C*H(CF₃)—C₄H₉, —C*H(CH₃)—C₈H₁₇, —C*H(CH₃)—C₇H₁₅, —C*H(CH₃)—C₆H₁₃, —C*H(CH₃)—C₅H₁₁, —C*H(C₂H₅)—C₅H₁₁, —C*H(C₂H₅)—C₆H₁₃, —CH₂—C*H (CH₃)—C₂H₅, —(CH₂)₃—C*H (CH₃)—C₂H₅, —C*H(CF₃)—CH₂—COO—C₂H₅, —C*H(CF₃)—(CH₂)₂OCH₃, —C*H (CF₃)—(CH₂)₃OC₂H₅, —C*H(CF₃)—(CH₂)₄OCH₃ and —C*H(CF₃)—(CH₂)₅OC₂H₅.

5. The liquid crystal material as claimed in claim 1, wherein the liquid crystal material is represented by the following formula;

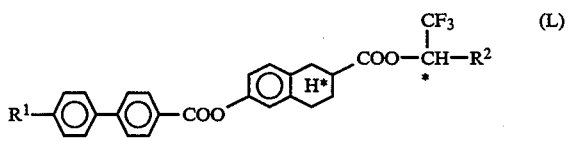
(L)

wherein R¹ is an alkyl or alkoxy group having 8–14 carbon atoms and R² is an alkyl group in which one of —CH₂— group can be substituted with —O— group or —COO— group, and an angle of rotation caused by an optical active structure having the chiral center which is one of the carbon atoms in the tetralin ring of said material is (−).

6. The liquid crystal material as claimed in claim 1, wherein the liquid crystal material is represented by the following formula;

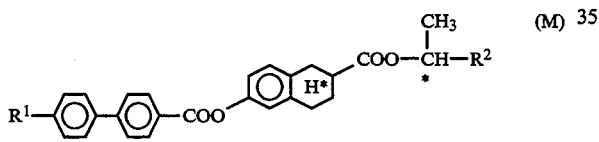
(M)

wherein R¹ is an alkyl or alkoxy group having 8–14 carbon atoms and R² is an alkyl group in which one of —CH₂— group may be substituted with —O— group or —COO— group, and an angle of rotation caused by a optical active structure having the chiral center which is one of the carbon atoms in the tetralin ring of said material is (+).

7. The liquid crystal material as claimed in claim 1, which is obtained from a compound, in which an angle of rotation caused by an optical active structure having the chiral center which is one of the carbon atoms in the tetralin ring of said material is (−), selected from the group consisting of 1,2,3,4-tetrahydro-6-alkoxynaphthalene-2-carboxylic acid, 1,2,3,4-tetrahydro-6-hydroxynaphthalene-2-carboxylic acid and 1,2,3,4-tetrahydro-6-benzyloxynaphthalene-2-carboxylic acid, and a monoalchohol having 4–20 carbon atoms.

8. The liquid crystal material as claimed in claim 7, wherein said monoalchohol having 4–20 carbon atoms is 1-trifluoromethylalchohol [RCH(CF₃)OH:R=-C2–C18].

9. The liquid crystal material as claimed in claim 1, which is obtained from a compound, in which an angle of rotation caused by an optical active structure having the chiral center which is one of the carbon atoms in the tetralin ring of said material is (+), selected from the group consisting of 1,2,3,4-tetrahydro-6-alkoxynaphthalene-2-carboxylic acid, 1,2,3,4-tetrahydro-6-hydroxynaphthalene-2-carboxylic acid and 1,2,3,4-tetrahydro-6-benzyloxynaphthalene-2-carboxylic acid, and a monoalchohol having 4–20 carbon atoms.

10. The liquid crystal material as claimed in claim 9, wherein said monoalchohol having 4–20 carbon atoms is 1-methylalchohol [RCH(CH₃)OH:R=C2–C18].

11. A liquid crystal composition comprising a tetralin compound represented by the following formula [I]:

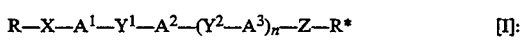

wherein R is an alkyl or polyfluoroalkyl group of 3 to 20 carbon atoms in which a part of —CH₂— groups or —CF₂— groups can be substituted with —O— group, said —CH₂— groups or —CF₂— groups being not directly bonded to X and not adjacent to each other, X is a group selected from the group consisting of —COO—, —O—CO—, —CO— and —O—, or a single bond, n is 0 or 1, at least one group of A¹, A² and A³ existing in the formula [I] is an optically active group selected from the group consisting of

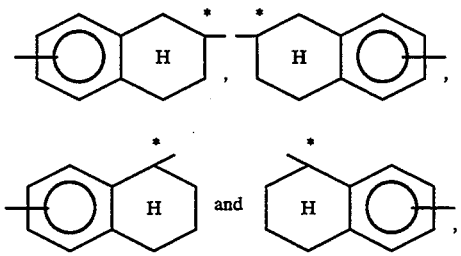

wherein a symbol of * denotes as chiral center of the optical active structure in the tetraline ring, the residual groups of A¹, A² and A³ are each independently a group selected from the group consisting of

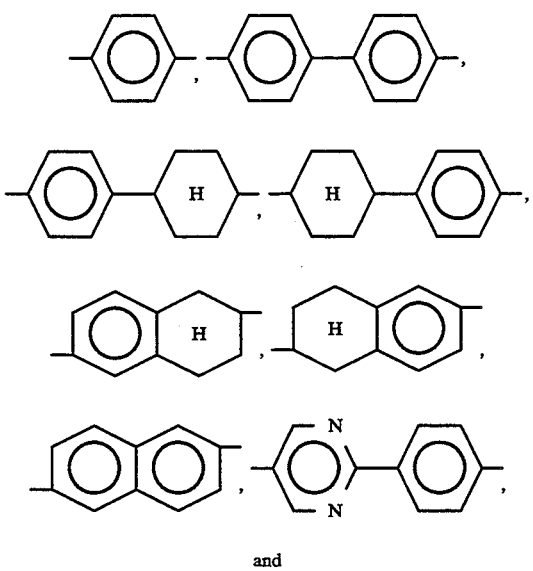

and

-continued

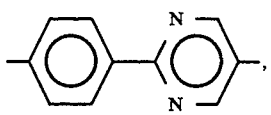

$Y^1$ and $Y^2$ are each independently a group selected from the group consisting of —COO—, —O—CO—, —CH$_2$CH$_2$, —CH$_2$O—, —O—CH$_2$—, —CO—CH$_2$— and —CH$_2$—CO—, Z is a group selected from the group consisting of —O—, —CO—, —COO— and —O—CO—, or a single bond, and R* is an optically active group of 4 to 20 carbon atoms having at least one asymmetric carbon atom in which a hydrogen atom bonded to a carbon atom of said optically active group can being substituted with a halogen atom.

12. A liquid crystal element comprising:
a cell which includes two substrates facing each other and having a gap therebetween, and
a liquid crystal material filled in the gap,
wherein the liquid crystal material comprises a tetralin compound represented by the following formula [I]:

R—X—A$^1$—Y$^1$—A$^2$—(Y$^2$—A$^3$)$_n$—Z—R*  [I]

wherein R is an alkyl or polyfluoroalkyl group of 3 to 20 carbon atoms in which a part of —CH$_2$— groups or —CF$_2$— groups can be substituted with —O— group, said —CH$_2$— groups or —CF$_2$— groups being not directly bonded to X and not adjacent to each other, X is a group selected from the group consisting of —COO—, —O—CO—, —CO— and —O—, or a single bond, n is 0 or 1, at least one group of A$^1$, A$^2$ and A$^3$ existing in the formula [I] is an optically active group selected from the group consisting of

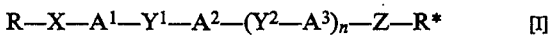

wherein a symbol of * denotes as chiral center of the optical active structure in the tetraline ring, the residual groups of A$^1$, A$^2$ and A$^3$ are each independently a group selected from the group consisting of

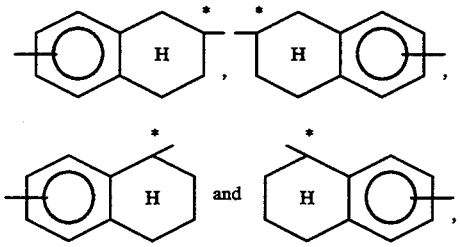

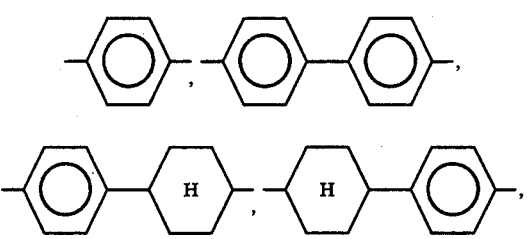

-continued

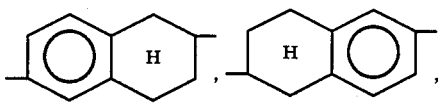

and

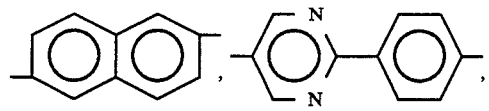

$Y^1$ and $Y^2$ are each independently a group selected from the group consisting of —COO—, —O—CO—, —CH$_2$CH$_2$—, —CH$_2$O—, —O—CH$_2$—, —CO—CH$_2$— and —CH$_2$—CO—, Z is a group selected from the group consisting of —O—, —CO—, —COO— and —O—CO—, or a single bond, and R* is an optically active group of 4 to 20 carbon atoms having at least one asymmetric carbon atom in which a hydrogen atom bonded to a carbon atom of said optically active group may being substituted with a halogen atom.

13. A carboxylic acid ester compound, which is represented by the following formula;

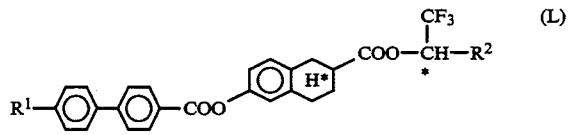

wherein R$^1$ is an alkyl or alkoxy group having 8-14 carbon atoms and R$^2$ is an alkyl group in which one of —CH$_2$— group can be substituted with —O— group or —COO— group, and an angle of rotation caused by an optical active structure having the chiral center which is one of the carbon atoms in the tetralin ring of said material is (—).

14. A carboxylic acid ester compound, which is represented by the following formula;

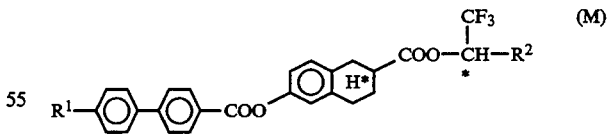

wherein R$^1$ is an alkyl or alkoxy group having 8-14 carbon atoms and R$^2$ is an alkyl group in which one of —CH$_2$— group can be substituted with —O— group or —COO— group, and an angle of rotation caused by an optical active structure having the chiral center which is one of the carbon atoms in the tetralin ring of said material is (+).

15. The liquid crystal material as claimed in claim 1, wherein R* is a group represented by the following formula [II]:

$$-Q^1-C^*H(Q^2)-Q^3 \quad \text{[II]}$$

wherein $Q^1$ is $-(CH_2)_q-$ in which q is an integer of from 0 to 6, and when q is 2 or more one $-CH_2-$ group may replaced with $-O-$ group; $Q^2$ and $Q^3$ are each independently an alkyl group of 1 to 10 carbon atoms, a fluoroalkyl group of 1 to 10 carbon atoms or a halogen atom, and are different from each other; and when $Q^2$ and/or $Q^3$ are alkyl or fluoroalkyl of 2 or more carbon atoms, one or more of $CH_2$ groups of $CF_2$ groups can be replaced with a group selected from the group consisting of $-O-$, $-S-$, $-CO-$, $-CHX^1-$ in which $X^1$ is a halogen atom, $-CHCN-$, $-O-CO-$, $-O-COO-$, $-COO-$ and $-CH=CH-$ with the proviso that when more than one $CH_2$ group or $CF_2$ group is replaced, the replacement groups can be the same or different with the further proviso that two hetero atoms are not directly bonded to each other.

16. The liquid crystal material as set forth in claim 15 wherein $Y^1$ and $Y^2$ are each independently $O-CO-$ or $-COO-$; and wherein Z is $-O-$ or $-COO-$.

17. The liquid crystal material as set forth in claim 1 wherein $Y^1$ and $Y^2$ are each independently $O-CO-$ or $-COO-$; and wherein Z is $-O-$ or $-COO-$.

18. The liquid material as claimed in claim 17 wherein R* is a group selected from the group consisting of $-C^*H(CF_3)-C_6H_{13}$, $-C^*H(CF_3)-C_5H_{11}$, $-C^*H(CF_3)-C_4H_9$, $-C^*H(CH_3)-C_8H_{17}$, $-C^*H(CH_3)-C_7H_{15}$, $-C^*H(CH_3)-C_6H_{13}$, $-C^*H(CH_3)-C_5H_{11}$, $-C^*H(C_2H_5)-C_5H_{11}$, $-C^*H(C_2H_5)-C_6H_{13}$, $-CH_2$ $C^*H(CH_3)-C_2H_5$, $-(CH_2)_3-C^*H(CH_3)-C_2H_5$, $-C^*H(CF_3)-CH_2-COO-C_2H_5$, $-C^*H(CF_3)-(CH_2)_2OCH_3$, $-C^*H(CF_3-(CH_2)_3OC_2H_5$, $-C^*H(CF_3)-(CH_2)_4OCH_3$ and $-C^*H(CF_3)-(CH_2)_5OC_2H_5$.

* * * * *